United States Patent [19]

DiNinno et al.

[11] Patent Number: 5,240,920
[45] Date of Patent: Aug. 31, 1993

[54] 2-(SUBSTITUTED-DIBENZOFURANYL AND DIBENZOTHIENYL) CARBAPENEM ANTIBACTERIAL AGENTS

[75] Inventors: Frank P. DiNinno, Old Bridge; Thomas N. Salzmann, North Plainfield; Mark L. Greenlee, Rahway, all of N.J.

[73] Assignee: Merck & Co., Inc., Rahway, N.J.

[21] Appl. No.: 878,136

[22] Filed: May 4, 1992

Related U.S. Application Data

[63] Continuation of Ser. No. 596,152, Oct. 11, 1990, abandoned.

[51] Int. Cl.$^5$ .................... A61K 31/40; C07D 487/04
[52] U.S. Cl. ..................... 514/210; 540/302
[58] Field of Search .......... 540/302; 514/210

[56] References Cited

U.S. PATENT DOCUMENTS

| | | | |
|---|---|---|---|
| 5,132,420 | 6/1992 | DiNinno et al. | 540/302 |
| 5,151,512 | 9/1992 | DiNinno et al. | 540/302 |
| 5,153,186 | 10/1992 | DiNinno | 514/210 |
| 5,157,033 | 10/1992 | DiNinno | 514/210 |

Primary Examiner—Thurman K. Page
Assistant Examiner—Jyothsna Venkat
Attorney, Agent, or Firm—Gabriel Lopez; Joseph F. DiPrima

[57] ABSTRACT

Carbapenems having the formula:

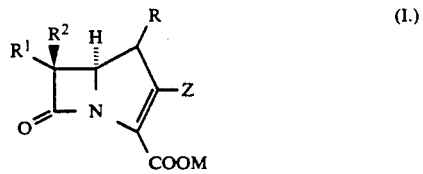

(I.)

where Z is;

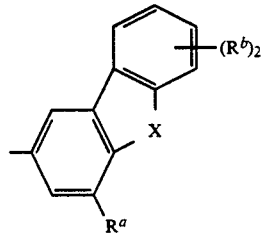

(A.)

or

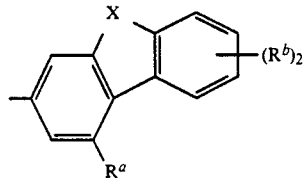

(B.)

where X is O or $S(O)_{0-2}$;

are useful antibacterial agents, especially with respect to activity against methicillin resistant *Staphylococcus aureus* (MRSA).

24 Claims, No Drawings

2-(SUBSTITUTED-DIBENZOFURANYL AND DIBENZOTHIENYL) CARBAPENEM ANTIBACTERIAL AGENTS

This is a continuation of U.S. application Ser. No. 07/596,152, filed Oct. 11, 1990, now abandoned.

BACKGROUND OF THE INVENTION

The present invention relates to antibacterial agents of the carbapenem class, in which the 2-position side chain is characterized by a dibenzofuranyl or dibenzothienyl moiety, substituted by various cationic and neutral substituents as described in more detail further below.

Thienamycin was an early carbapenem antibacterial agent having a broad spectrum; it has the following formula:

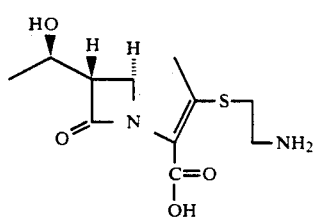

Later, N-formimidoyl thienamycin was discovered; it has the formula:

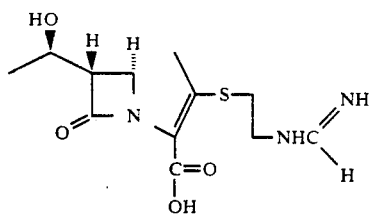

The 2-(substituted-dibenzofuranyl and dibenzothienyl) carbapenems of the present invention are not characterized by a broad antibacterial spectrum such as that of thienamycin or N-formimidoyl thienamycin; but rather, their spectrum of activity is largely limited to gram positive microorganisms, especially methicillin resistant *Staphylococcus aureus* (MRSA) and *Staphylococcus epidermidis* (MRSE); and methicillin resistant coagulase negative Staphylococci (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance by the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

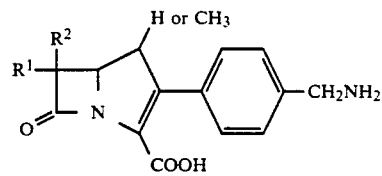

However, there is no description or suggestion of a dibenzofuranyl or dibenzothienyl 2-substituent such as characterizes the compounds of the present invention; nor is there any suggestion of the surprisingly better anti-MRSA/MRCNS activity of the compounds of the present invention.

EP-A-0 277 743 describes a particular class of compounds of the formula:

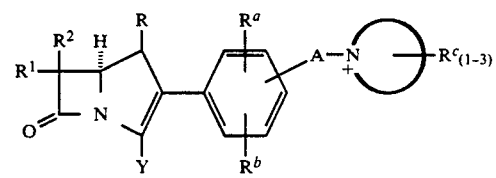

but this limited teaching in no way suggests the totally different compounds of the present invention, nor their surprisingly better anti-MRSA/MRCNS activity.

SUMMARY OF THE INVENTION

The present invention provides novel carbapenem compounds of the formula:

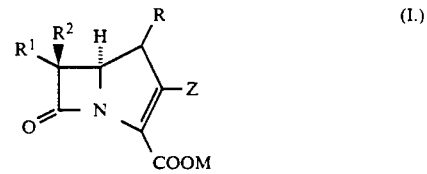

where Z is:

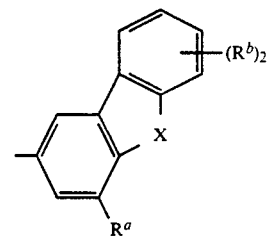

or

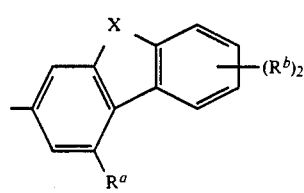

wherein:
X is O or $S(O)_{0-2}$;
R is H or $CH_3$;
$R^1$ and $R^2$ are independently H, $CH_3-$, $CH_3CH_2-$, $(CH_3)_2CH-$, $HOCH_2-$, $CH_3CH(OH)-$, $(CH_3)_2C(OH)-$, $FCH_2CH(OH)-$, $F_2CHCH(OH)-$, $F_3CCH(OH)-$, $CH_3CH(F)-$, $CH_3CF_2-$, or $(CH_3)_2C(F)-$;

$R^a$ and $R^b$ are independently selected from the group consisting of hydrogen and the radicals set out below provided that one but not more than one of $R^a$ or $R^b$ is selected from Type I substituents and in total not more than three $R^a$ and $R^b$ radicals are other than hydrogen:

I.
a)

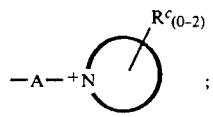

where

A is $(CH_2)_m-Q-(CH_2)_n$, where m is 0 to 6 and n is 1 to 6 and Q is a covalent bond, O, S, SO, $SO_2$, NH, $-SO_2NH-$, $-NHSO_2-$, $-CONH-$, $-NH-CO-$, $-SO_2N(C_1-C_4alkyl)-$, $-N(C_1-C_4alkyl)SO_2-$, $-CON(C_1-C_4alkyl)-$, $-N(C_1-C_4alkyl)CO-$, $-CH=CH-$, $-CO-$, $-OC(O)-$, $-C(O)O-$ or $N(C_1-C_4alkyl)$ and $(CH_2)_m$ is attached to the dibenzofuranyl or dibenzothienyl moiety;

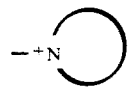

is a 5- or 6-membered monocyclic heterocycle or an 8-, 9- or 10-membered bicyclic heterocycle, the heterocycle containing a first nitrogen in an aromatic 5- or 6-membered first ring, with attachment of the heterocycle to A by way of said first nitrogen and said first nitrogen is quaternary by virtue of the attachment in addition to the ring bonds thereto, with the first ring containing 0 or 1 of either O or S, with the first ring containing 0 to 3 additional nitrogen atoms, with the first ring optionally fused to a 3- or 4-membered moiety to form the optional second ring, with the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

$R^c$ is $R^a$ as defined under II below, hydrogen, or $-NR^yR^z$ (where $R^y$ and $R^z$ are defined in II below), but independently selected from $R^a$ and from each other if more than one $R^c$ is present, and is attached to a carbon ring atom or a nitrogen heteroatom the valency of which is not satisfied by the ring bonds;

b)

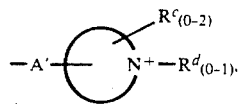

where

is a 5- or 6-membered monocyclic heterocycle or an 8-, 9- or 10-membered bicyclic heterocycle, the heterocycle containing a first nitrogen in an aromatic 5- or 6-membered first ring, with said first nitrogen either quaternary by virtue of a substituent $R^d$ in addition to the ring bonds thereto or neutral in the absence of a substituent $R^d$, with attachment of the heterocycle to A' by way of a carbon atom of a ring, with the first ring containing 0 or 1 of either O or S, with the first ring containing 0 to 2 additional nitrogen atoms, with the first ring optionally fused to a 3- or 4-membered moiety to form the optional second ring, with the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

$R^c$ is defined above;

$R^d$ is hydrogen, $NH_2$, $O^-$ or $C_1-C_4alkyl$ (where the alkyl group is optionally mono-substituted with $R^q$ as defined under IIc below) with the proviso that $R^d$ is present and is not H when either 1) m and n in A' below are both zero and Q is $-OC=O$, S, SO, $SO_2$, $-NHSO_2$, $-N(C_1-C_4 alkyl)SO_2$, or $-CO$, or 2) m+n in A' below is equal to or less than 2 and Q is $CH=CH$ and

is pyridinium, quinolinium, or, isoquinolinium;

A' is $(CH_2)_m-Q-(CH_2)_n$, where m is 0 to 6 and n is 0 to 6, Q is as given above, except that when m and n are both 0 then Q is not a covalent bond, and $(CH_2)_m$ is attached to the dibenzofuranyl or dibenzothienyl moiety;

c) $-A_p-N^+R^y(R^w)_{(0-1)}(R^z)$ where $R^y$ and $R^z$ are as defined under II below, $R^y$ and $R^z$ may further be together a $C_2-C_4$ alkylidene radical to form a ring (optionally mono-substituted with $R^q$ as defined below) interrupted by $N(O)R^e$ or $N^+(R^e)_2$ (where $R^e$ is hydrogen, $C_1-C_4$ alkyl, or $C_1-C_4$ alkyl mono-substituted with $R^q$ as defined below), $R^w$ is hydrogen, $C_{1-4}$ alkyl, $O^-$, $NH_2$, or absent in which case the nitrogen is neutral, $R^w$, $R^y$ and $R^z$ may further together form a $C_5-C_{10}$ tertiary alkylidene radical which with $N^+$ forms a bicyclic ring, where the tertiary alkylidene radical is optionally mono-substituted with $R^q$ as defined below and where the tertiary carbon of the tertiary alkylidene radical is optionally replaced with nitrogen, $N^+R^e$ (where $R^e$ is defined above), or $N^+-O^-$, P is 0 or 1, and A is as defined above;

d)

where

is a 5- or 6-membered monocyclic heterocycle or an 8-, 9- or 10-membered bicyclic heterocycle, the heterocycle containing a first nitrogen in a first ring, with the first ring saturated or unsaturated and non-aromatic, with the first nitrogen either quaternary by virtue of one or two substituents $R^d$ in addition to the ring bonds thereto or neutral by virtue of 0 or 1 substituent $R^d$ in addition to the ring bonds thereto, with attachment of the heterocycle to A' by way of a carbon atom or non-quaternary nitrogen atom of a ring, with the first ring containing in addition to carbon and the first nitrogen 0 to 1 of a member selected from the group consisting of the non-quaternary nitrogen of attachment, O, S, S(O), S(O)$_2$ and NR$^e$ where R$^e$ is defined above, with the first ring optionally fused to a 2-, 3- or 4-membered moiety to form the optional second ring, with the moiety optionally containing in addition to carbon the non-quaternary nitrogen of attachment, and with the moiety saturated or unsaturated and the second ring non-aromatic;

$R^d$ is as defined above except without the proviso and where more than one $R^d$ is present on a nitrogen, at least one $R^d$ is hydrogen or $C_1$–$C_4$ alkyl;

A' is defined above;

p is defined above; and $R^q$ is defined below;

II.
a) a trifluoromethyl group: —CF$_3$;
b) a halogen atom: —Br, —Cl, —F, or —I;
c) $C_1$–$C_4$ alkoxy radical: —OC$_{1-4}$ alkyl, wherein the alkyl is optionally mono-substituted by $R^q$, where $R^q$ is a member selected from the group consisting of —OH, —OCH$_3$, —CN, —C(O)NH$_2$, —OC(O)NH$_2$, CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$, —COOM$^a$ (where M$^a$ is hydrogen, alkali metal, methyl or phenyl), tetrazolyl (where the point of attachment is the carbon atom of the tetrazole ring and one of the nitrogen atoms is mono-substituted by M$^a$ as defined above), and —SO$_3$M$^b$ (where M$^b$ is hydrogen or an alkali metal);

d) a hydroxy group: —OH;
e) a carbonyloxy radical: —O(O)CR$^s$, where
$R^s$ is $C_{1-4}$ alkyl, phenyl, or heteroaryl, each of which is optionally mono-substituted by $R^q$ as defined above, and where heteroaryl is a monocyclic aromatic hydrocarbon group having 5 or 6 ring atoms, in which a carbon atom is the point of attachment, one carbon atom has been replaced by a nitrogen atom, one additional carbon atom is optionally replaced by a heteroatom selected from O and S, and from 1 to 3 additional carbon atoms are optionally replaced by a nitrogen heteroatom;

f) a carbamoyloxy radical: —O(O)CN(R$^y$)R$^z$, where

R$^y$ and R$^z$ are independently H, $C_{1-4}$ alkyl, together a 3- or 5-membered alkylidene radical to form a ring, or together a 2- to 4-membered alkylidene radical, interrupted by —O—, —S—, —S(O)— or —S(O)$_2$—, to form a ring, and where R$^y$ or R$^z$ or both are defined as alkyl, including where joined together to form a ring, the alkyl is optionally mono-substituted by R$^q$, as defined above;

g) a sulfur radical: —S(O)$_n$—R$^s$ where n=0–2, and R$^s$ is as defined above;

h) a sulfamoyl group: —SO$_2$N(R$^y$)R$^z$ where R$^y$ and R$^z$ are as defined above;

i) azido: N$_3$ j) a formylamino group: —N(R$^t$)—C(O)H, where R$^t$ is H or $C_{1-4}$ alkyl, and the alkyl thereof is optionally mono-substituted by R$^q$ as defined above;

k) ($C_1$–$C_4$ alkyl)carbonylamino radical: —N(R$^t$)—C(O)$C_{1-4}$ alkyl, where R$^t$ is as defined above, and the alkyl group is also optionally mono-substituted by R$^q$ as defined above;

l) a ($C_1$–$C_4$ alkoxy) carbonylamino radical: —N(R$^t$)—C(O)O$C_{1-4}$ alkyl, where R$^t$ is as defined above, and the alkyl group is also optionally mono-substituted by R$^q$ as defined above;

m) a ureido group: —N(R$^t$)—C(O)N(R$^y$)R$^z$ where R$^t$, R$^y$ and R$^z$ are as defined above;

n) a sulfonamido group: —N(R$^t$)SO$_2$R$^s$, where R$^s$ and R$^t$ are as defined above;

o) a cyano group: —CN;

p) a formyl or acetalized formyl radical: —C(O)H or —C(OCH$_3$)$_2$;

q) ($C_1$–$C_4$ alkyl)carbonyl radical wherein the carbonyl is acetalized: —C(OCH$_3$)$_2$$C_{1-4}$ alkyl, where the alkyl is optionally mono-substituted by R$^q$ as defined above;

r) carbonyl radical: —C(O)—R$^s$, where R$^s$ is as defined above;

s) a hydroximinomethyl radical in which the oxygen or carbon atom is optionally substituted by a $C_1$–$C_4$ alkyl group: —(C=NOR$^z$)R$^y$ where R$^y$ and R$^z$ are as defined above, except they may not be joined together to form a ring;

t) a ($C_1$–$C_4$ alkoxy)carbonyl radical: —C(O)O$C_{1-4}$ alkyl, where the alkyl is optionally mono-substituted by R$^q$ as defined above;

u) a carbamoyl radical: —C(O)N(R$^y$)R$^z$ where R$^y$ and R$^z$ are as defined above;

v) an N-hydroxycarbamoyl or N($C_1$–$C_4$ alkoxy)-carbamoyl radical in which the nitrogen atom may be additionally substituted by a $C_1$–$C_4$ alkyl group: —C(O)—N(OR$^y$)R$^z$ where R$^y$ and R$^z$ are as defined above, except that they may not be joined together to form a ring;

w) a thiocarbamoyl group: —C(S)N(R$^y$)R$^z$ where R$^y$ and R$^z$ are as defined above;

x) carboxyl: —COOM$^b$, where M$^b$ is as defined above;

y) thiocyanate: —SCN;

z) trifluoromethylthio: —SCF$_3$;

aa) tetrazolyl, where the point of attachment is the carbon atom of the tetrazole ring and one of the nitrogen atoms is mono-substituted by hydrogen, an alkali metal or a $C_1$–$C_4$ alkyl optionally substituted by $R^q$ as defined above;

ab) an anionic function selected from the group consisting of: phosphono $[P=O(OM^b)_2]$; alkylphosphono $\{P=O(OM^b)\text{-}[O(C_1\text{-}C_4 \text{ alkyl})]\}$; alkylphosphinyl $[P=O(OM^b)\text{-}(C_1\text{-}C_4\text{alkyl})]$; phosphoramido $[P=O(OM^b)N(R^y)R^z$ and $P=O(OM^b)NHR^s]$; sulfino $(SO_2M^b)$; sulfo $(SO_3M^b)$; acylsulfonamides selected from the structures $CONM^bSO_2R^s$, $CONM^bSO_2N(R^y)R^z$, $SO_2NM^bCON(R^y)R^z$; and $SO_2NM^bCN$, where $R^s$, $M^b$, $R^y$, and $R^z$ are as defined above;

ac) $C_5$–$C_7$ cycloalkyl group in which one of the carbon atoms in the ring is replaced by a heteroatom selected from O, S, NH or $N(C_1\text{-}C_4 \text{ alkyl})$ and in which one additional carbon atom may be replaced by NH or $N(C_1\text{-}C_4 \text{alkyl})$, and in which at least one carbon atom adjacent to each nitrogen heteroatom has both of its attached hydrogen atoms replaced by one oxygen thus forming a carbonyl moiety and there are one or two carbonyl moieties present in the ring;

ad) $C_2$–$C_4$ alkenyl radical, optionally mono-substituted by one of the substituents a) to ac) above, or pyridyl, phenyl, quinoline, or isoquinoline each of which is optionally substituted by $R^q$ as defined above;

ae) $C_2$–$C_4$ alkynyl radical, optionally mono-substituted by one of the substituents a) to ac) above;

af) $C_1$–$C_4$ alkyl radical;

ag) $C_1$–$C_4$ alkyl mono-substituted by one of the substituents a)–ac) above;

ah) a 2-oxazolidinonyl moiety in which the point of attachment is the nitrogen atom of the oxazolidinone ring, the ring oxygen atom is optionally replaced by a heteroatom selected from S and $NR^t$ (where $R^t$ is as defined above) and one of the saturated carbon atoms of the oxazolidinone ring is optionally mono-substituted by one of the substituents a) to ag) above;

M is selected from:
i) hydrogen;
ii) a pharmaceutically acceptable esterifying group or removable carboxyl protecting group;
iii) an alkali metal or other pharmaceutically acceptable cation; or
iv) a negative charge which is balanced by a positively charged group.

DETAILED DESCRIPTION OF THE INVENTION

The compounds of the present invention have as the basis for the 2-position substituent a dibenzofuranyl or dibenzothienyl moiety. Different isomeric structures result depending upon point of attachment, and thus for convenience Formula I bears the 2-position substituent Z, which is then defined (without substituents) as:

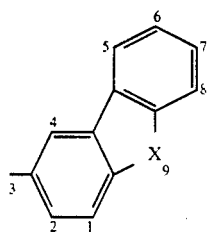

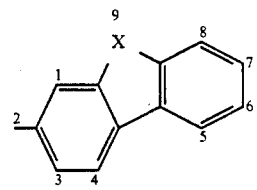

where (A.) and (B.) represent the two isomeric forms, and where X can be oxygen (O), in which case a dibenzofuran nucleus results, or X can be sulfur, in which case a dibenzothiophene nucleus results. Where X is sulfur, the sulfur atom can also be oxygenated with one or two atoms of oxygen. These three possibilities are conveniently summarized in the definition of X as $S(O)_{0-2}$. These two types of nuclei, oxygen- and sulfur-containing, have been found to possess roughly comparable antibacterial, especially anti-MRSA activity, when substituted by the same substituent, even though significant individual substituent/activity variation may exist, and thus both types of nuclei are considered to be part of the same invention, as further described herein. It has also been found that oxygenation of the sulfur atom produces significant changes in biological activity from that of the unoxygenated sulfur species. For example, certain S compounds experience an in vivo efficacy deficit compared to in vitro antibacterial values. The identical $S(O)_1$ compound does not show this deficit, probably as result of reduced plasma protein binding. The $S(O)_1$ compounds are also, usually, more water soluble. Consequently, the oxygenated sulfur forms of the dibenzothienyl nucleus are also considered a preferred aspect of the present invention.

In the first ring it has been found that the 2- and 4- and 1- and 3-positions of the (A.) and (B.) isomers, respectively, are relatively inaccessible synthetically, thus leaving only the 1- and 4-positions, respectively, for substitution, i.e., the $R^a$ substituent. In the second ring, by contrast, it is within the scope of the present invention to permit substitution at the 5-, 6-, 7-, and 8-positions, although at most two such at a time. These substituents are designated $(R^b)_2$. Overall, it is theorized that the fused ring system represented by the dibenzofuran and dibenzothiophene nuclei enforces coplanarity of the two phenyl rings involved in the system, thus contributing significantly to the biological activities of the compounds. Nevertheless, a wide range of substitution is possible and often particular substituents significantly enhance overall biological activity.

The Type II $R^a$ and $R^b$ substituents are distinguishable from Type I substituents chemically and with respect to the biological properties which they confer. In related compounds, it has been found that the Type II substituted compounds afford greater water solubility and reduced potential for CNS side effects. Substituents which tend to confer improved water solubility on the overall compound have been found useful, since they are contemplated to thereby improve the transport of the compound involved. Although a substantial number and range of Type II substituents have been described herein, all of these are contemplated to be a part of the present invention based on the biological performance of substituents related in terms of their medicinal chemistry.

Since it is possible to combine, in the compounds of the present invention, the required Type I substituents with the optional Type II substituents, there can be obtained a combination of desired attributes in the final overall molecule not attainable with a single substituent, i.e., improved anti-MRSA/MRCNS activity together with enhanced water solubility.

Type I substituents employed in the compounds of the present invention may have quaternary nitrogen groups, and these include both cyclic and acyclic types, as is described under Type I. As already pointed out above, it is required that one, but no more than one, of the substituents $R^a$ and $R^b$ must be a member selected from the group consisting of the definitions under Type I. It is optional that one, or at most two, of the remaining substituents may be a member selected from the group consisting of definitions under Type II. For example, $R^b$ at position 7- may be Type I and $R^a$ at position 1- may be of Type II, while the remaining substituents are hydrogen.

Although a substantial number and range of such neutral and anionic substituents have been described herein, all of these are contemplated to be a part of the present invention based on the biological performance of substituents related in terms of their medicinal chemistry.

It has been found beneficial to employ an electron withdrawing group at the 1- or 4-position ($R^a$), although other types of substituents may also be employed. Substituents which tend to confer improved water solubility on the overall compound have been found useful, since they are contemplated to thereby improve the transport of the compound involved. A significant number of substituents of this type have been set forth. As a general matter, however, it is conjectured that the improved anti-MRSA activity results from conformation of the overall molecule uniquely conferred by the dibenzofuran and dibenzothiophene nuclei themselves. The Type I substituent provides still greater anti-MRSA/MRCNS activity to the molecule.

With reference to the above definitions, "alkyl" means a straight or branched chain aliphatic hydrocarbon radical.

The term "quaternary nitrogen" as used herein refers to a tetravalent cationic nitrogen atom including the cationic nitrogen atom in a tetra-alkylammonium group (e.g., tetramethylammonium, N-methylpyridinium), the cationic nitrogen atom in a protonated ammonium species (e.g., trimethylhydroammonium, N-hydropyridinium), the cationic nitrogen atom in an amine N-oxide (e.g., N-methylmorpholine-N-oxide, pyridine-N-oxide), and the cationic nitrogen atom in an N-amino-ammonium group (e.g., N-aminopyridinium).

The term "heteroatom" means N, S, or O, selected on an independent basis.

The term "heteroaryl" has been defined herein, in relation to the $R^s$ group, to have a specific and limited meaning, being only monocyclic. While the Type I. a) and b) substituents also clearly include heteroaryl groups, being both monocyclic and bicyclic, the term "heteroaryl" has not been used in association with the definitions of those substituents above. It is required that the monocyclic heteroaryl have at least one nitrogen atom, and optionally at most only one additional oxygen or sulfur heteroatom may be present. Heteroaryls of this type are pyrrole and pyridine (1 N); and oxazole, thiazole or oxazine (1 N+1 O or 1 S). While additional nitrogen atoms may be present together with the first nitrogen and oxygen or sulfur, giving, e.g., a thiadiazole (2N's+1S), the preferred heteroaryls are those where only nitrogen heteroatoms are present when there is more than one. Typical of these are pyrazole, imidazole, pyrimidine and pyrazine (2 N's); triazine (3 N's); and tetrazole (4 N's).

The heteroaryl group of $R^s$ is always optionally mono-substituted by $R^q$, defined above, and substitution can be on one of the carbon atoms or one of the heteroatoms, although in the latter case certain substituent choices may not be appropriate.

The term "tetrazolyl" as used herein refers to only the tetrazole radical wherein the point of attachment is the carbon atom of the tetrazole ring.

In preferred compounds of Formula I, $R^2$ is hydrogen. More preferably, $R^1$ is (R)—CH$_3$CH(OH)— or (R)—CH$_3$CH(F)— and $R^2$ is hydrogen. In the most preferred case, $R^1$ is (R)—CH$_3$CH(OH)— and $R^2$ is hydrogen.

Representative $R^a$ and $R^b$ groups are H, —CH$_3$, —CH$_2$CH$_3$, —(CH$_2$)$_3$CH$_3$, —OCH$_3$, —SCH$_3$, tetrazolyl, —COOH, —CH$_2$CONH$_2$, —CH$_2$CH$_2$SO$_3$H, —CONH$_2$, —SO$_2$NH$_2$, —SO$_3$H, —CON(CH$_3$)$_2$, —CN, —CH$_2$CN, —CH$_2$SCH$_3$, —CH$_2$SO$_3$H, —CH$_2$SO$_3$H, —CH$_2$SOCH$_3$, —SO$_2$CH$_3$, —SOCH$_3$, —CH$_2$OCH$_3$, —N$_3$, —OCONH$_2$, —OH, —CHO, —CH$_2$P(O)(OCH$_3$)OH, —CF$_3$, —CH$_2$OC(O)NH$_2$, —CH$_2$SO$_2$NH$_2$, —SCH$_2$CH$_2$CN, Br, Cl, F, —SCF$_3$, —CH$_2$SCF$_3$, —SCH$_2$CF$_3$, —COCH$_3$, —CH=NOH, —CONHOH, —C(S)NH$_2$, —OCOCH$_3$, —NHCOCH$_3$, —NHCO$_2$CH$_3$, —NHCONH$_2$, —NHSO$_2$CH$_3$, —SCN, —CH=CHCHO, —SCH$_2$CH$_2$OH, —CH$_2$OH, —CH=NOCH$_2$CO$_2$H, —CO$_2$CH$_2$CH$_2$OH, and —SO$_2$NHCH$_2$CONH$_2$.

While R=H is usually preferred, there are instances in which R=CH$_3$ may provide improved chemical stability, water solubility, or pharmacokinetic behavior. The substituent R=CH$_3$ may be of either configuration, i.e., the α- or β-stereoisomer. Of the two possible isomeric forms, designated (A.) and (B.), for both the dibenzofuran nucleus and dibenzothiophene nucleus, the isomeric form (A.) is clearly preferred in most cases, since it has been found that for nearly any given substituent, the (A.) isomer will possess greater antibacterial, especially anti-MRSA activity, than the (B.) isomer as the 2-sidechain of the overall carbapenem compound.

For the various subclasses of compounds of the present invention dictated by the definitions of X and isomeric forms as discussed above, it has been further found that generally there is a preference, within the framework of resultant overall antibacterial, especially anti-MRSA activity, for $R^a$ to be a Type II substituent and for $R^b$ to be a Type I substituent, although for the dibenzothiopheneoxides no such preference has been found.

Additionally, in preferred compounds of configuration (A), at least one $R^a$ or $R^b$ in the 1-, 7-, or 8-position of the dibenzofuran or dibenzothienyl compound is other than hydrogen. In the most preferred compounds, in total, up to two $R^a$ and/or $R^b$ substituents in either the 1-, 7-, or 8-positions are other than hydrogen.

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above may also include non-toxic acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, pamoate, pectinate, persulfate, 3-phenylpropionate, picrate, pivalate, propionate, succinate, tartrate, thiocyanate, tosylate, and undecanoate.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a fluoride salt, treatment with a transition metal catalyst and a nucleophile, and catalytic hydrogenation. Examples of such ester protecting groups include benzhydryl, p-nitrobenzyl, 2-naphthylmethyl, allyl, 2-chloroallyl, benzyl, 2,2,2-trichloroethyl, t-butyldimethylsilyl, t-butyldiphenylsilyl, 2-(trimethylsilyl)ethyl, phenacyl, p-methoxybenzyl, acetonyl, o-nitrobenzyl, p-methoxyphenyl, 4-pyridylmethyl, and t-butyl.

The compounds of the present invention are in general valuable antibacterial agents active against various Gram-positive and to a lesser extent, for the most part, Gram-negative bacteria and accordingly find utility in human and veterinary medicine. Representative pathogens which are sensitive to the antibacterial agents of the present invention include various species or strains of the following: Staphylococcus, Enterococcus, Escherichia coli, Klebsiella, Enterobacter, Bacillus, Salmonella, Serratia, Proteus, and Bacterium. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the anti-bacterial art. In general, a daily dosage consists of from about 5 to about 600 mg of active ingredient per kg of body weight of the subject in one or more treatments per day. A preferred daily dosage for adult humans lies in the range of from about 10 to 240 mg of active ingredient per kg of body weight. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10-60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5-50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections, and particularly urinary tract infections, a dose of 250 mg t.i.d. or q.i.d. is recommended. For moderate infections against highly susceptible gram positive and gram negative organisms, a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5-25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occurring carbapenems are susceptible to attack by a-renal enzyme known as dehydropeptidase (DHP). This attack or degradation may reduce the efficacy of the carbapenem antibacterial agent. The compounds of the present invention, on the other hand, are significantly less subject to such attack, and therefore may not require use of a DHP inhibitor. However, such use is optional and contemplated to be a part of the present invention. Inhibitors of DHP and their use with carbapenem antibacterial agents are disclosed in the prior art [see European Patent Applications No. 79102616.4 filed Jul. 24, 1979 (Patent No. 0 010 573); 79102615.6, filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of Formula I compound:DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

These combination compositions and their use are further embodiments of the present invention.

METHODS OF PREPARATION

The manufacture of compounds of Formula I may be carried out in a three-stage synthesis scheme followed by deprotection. The objective of the first synthesis stage is to produce a base dibenzofuranyl or dibenzothienyl compound which may be converted to the two-position substituent of the carbapenem of Formula I. The objective of the second synthesis stage is to attach the base dibenzo compound to the carbapenem. Finally, the objective of the third synthesis stage is to substitute the dibenzo compound with the desired $R^a$ and $R^b$. This third synthesis stage may either be performed after the first synthesis stage or after the second synthesis stage according to the nature of the desired $R^a$ and $R^b$.

The first synthesis stage can be achieved by many processes well-known in the art. The synthesis, substitution, and elaboration of dibenzofurans and dibenzothiophenes has been well reviewed in the literature:

M. V. Sargent and P. O. Stransky, Adv. Heterocycl. Chem. 35, 1-81 (1984); W. E. Parham, Heterocycl. Comp. 2, 123 (1951); R. Livingstone in Rodd's Chemistry of Carbon Compounds, 2nd Ed., Vol IV Part A, Heterocyclic Compounds, 194-202 (1973); F. M. Dean and M. V. Sargent in Comprehensive Heterocyclic Chemistry, Vol. 4, Part 3, 599 (1979); D. M. X. Donnelly and M. J. Meegan. ibid., 657 (1979); J. Ashby and C. C. Cook, Adv. Heterocycl. Chem. 16, 181-288 (1974); D. K. Fukushima, Heterocycl, Comp. 2, 164 (1951); R. Livingstone in Rodd's Chemistry of Carbon Compounds, 2nd Ed., Vol. IV Part A, Heterocyclic Compounds, 300-305 (1973); S. Rajappa in Comprehensive Heterocyclic Chemistry, Vol. 4, Part 3, 741 (1979); E. Campaigne, ibid., 863 (1979).

SCHEME 1

Scheme I shows the synthesis of the pyridyl-thioester intermediate I-A. The steps for preparing intermediate I-A are well known in the art and are analogous to the procedures described, for example, in U.S. Pat. Nos. 4,260,627 and 4,543,257; L. D. Cama et al. Tetrahedron 39, 2531 (1983); R. N. Guthikonda et al. J. Med. Chem. 30, 871 (1987).

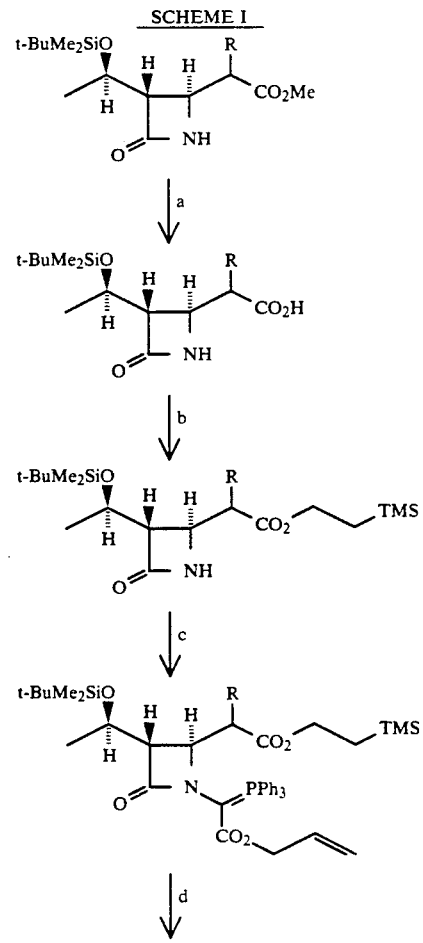

SCHEME I

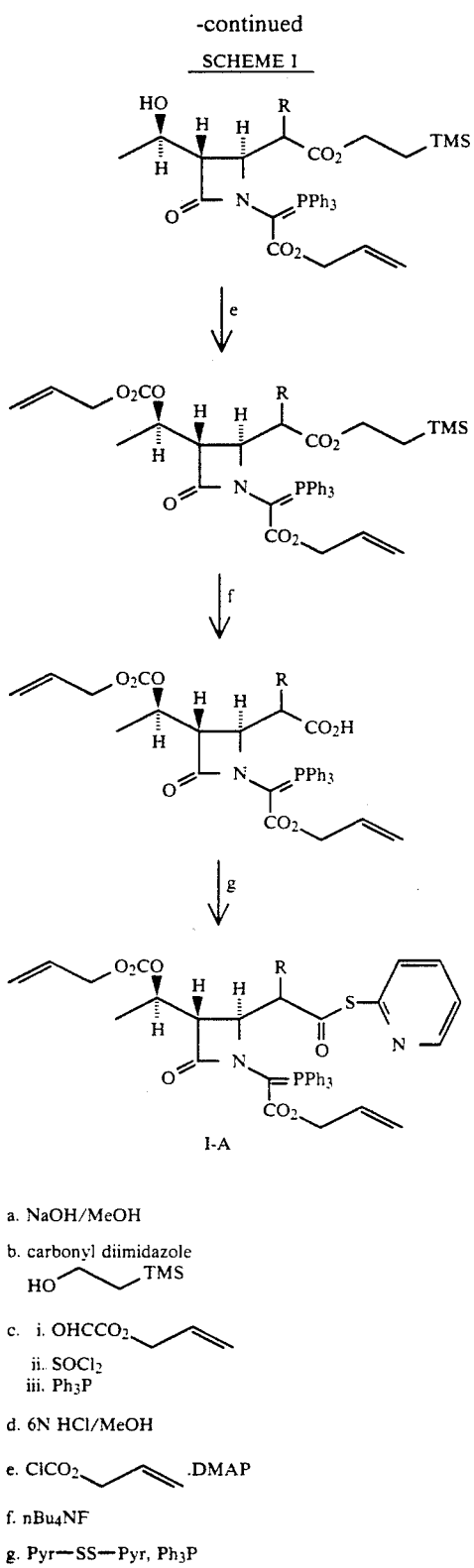

a. NaOH/MeOH b. carbonyl diimidazole
HO⌒TMS c. i. OHCCO₂⌒⌒
 ii. SOCl₂
 iii. Ph₃P d. 6N HCl/MeOH e. ClCO₂⌒⌒ DMAP f. nBu₄NF g. Pyr—SS—Pyr, Ph₃P Schemes II and III demonstrate two alternative second stage syntheses. The third synthesis varies according to the selected $R^a$ and $R^b$.

SCHEME II

Scheme II illustrates the coupling of I-A with the desired aromatic side-chain via a Grignard reaction followed by formation of the carbapenem ring system by an intramolecular Witting reaction. Thus, reaction of I-A with a dibenzofuranyl- or dibenzothienyl-bromomagnesium reagent III in tetrahydrofuran (THF) at from $-70°$ C. to about $20°$ C. gives an aryl ketone IV. The Grignard reagent III is prepared by conventional means from the corresponding aryl bromide II. Thus, reaction of II with magnesium metal in THF at from about $20°$ C. to $60°$ C. provides III. Alternatively, II may be reacted with t-butyllithium, n-butyllithium and the like in THF at from $-78°$ to $-50°$ C. followed by the addition of magnesium bromide to produce III. The substituted-dibenzofuranyl and -dibenzothienyl bromides II are prepared in the first synthesis stage by standard literature methods as described above. Cyclization of phosphorane IV is accomplished by heating at reflux in p-xylene ($138°$ C.) in the presence of hydroquinone as a radical scavenger for about 1 hour to provide the carbapenem ester V.

In the case of the dibenzothiophene nucleus (X=S), oxidation to the S-oxide (X=SO) is best accomplished after cyclization to the carbapenem V. The dibenzothienyl-dioxide compounds (X=SO₂) may be obtained by further oxidation of the corresponding S-oxide compound or, alternatively, by using a dibenzothienyl-dioxide starting material (II; X=SO₂) in the Grignard coupling reaction.

It is often advantageous for the $R^a$ and/or $R^b$ substituent of the side-chain precursor II to be introduced initially in a protected or precursory form. This is due to the incompatibility of certain substituents $R^a$ or $R^b$ with the highly basic and nucleophilic conditions of the Grignard reaction and/or the high temperature employed in the internal Witting cyclization. Depending on the specific substituent, elaboration to the desired $R^a$ and/or $R^b$ may be best accomplished at the phosphorane intermediate IV or after cyclization to the protected carbapenem V. For example, a t-butyldimethylsilyloxymethyl group may be employed as a precursor substituent on compound II. Removal of the t-butyldimethylsilyl protecting group would then best be carried out on intermediate IV, giving the corresponding hydroxymethyl substituent. This may be accomplished by exposure of compound IV to sulfuric acid in methanol at $0°$ C., conditions which would be incompatible with the acid sensitive carbapenem intermediate V. Further elaboration of the hydroxymethyl substituent to a desired $R^a$ or $R^b$ may then be accomplished on intermediate IV, or after cyclization to carbapenem V. After final elaboration of $R^a$ or $R^b$, removal of the protecting groups from V provides the final compound of Formula I. Such final elaboration and deprotection is described in further detail below.

SCHEME II

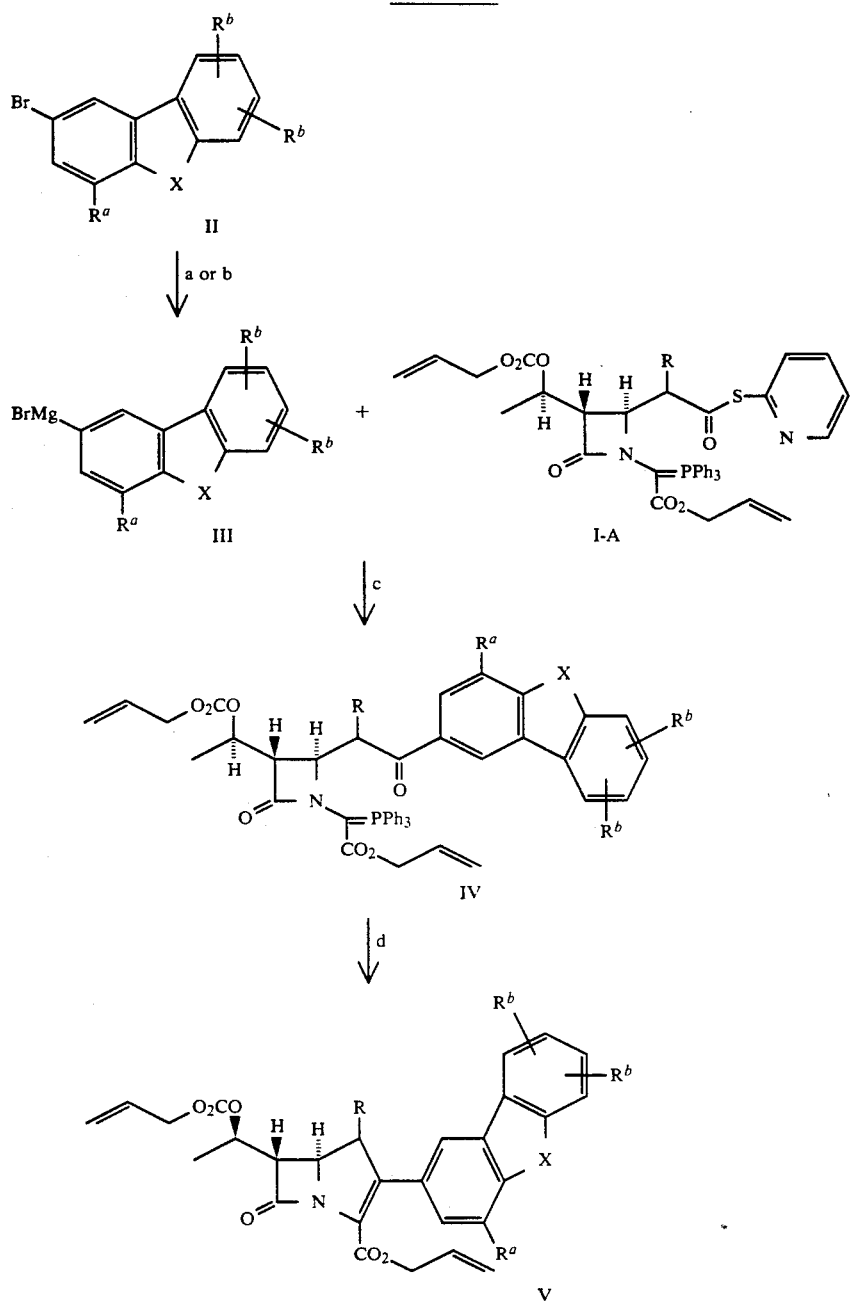

a. Mg, THF
b. i. t-BuLi, THF
   ii. MgBr$_2$ c. THF, −70° C. ⟶ −20° C.
d. p-xylene, 138° C.

SCHEME III

Scheme III shows an alternative second stage synthesis, i.e. attachment of the base dibenzofuranyl or dibenzothienyl compound such as II to the 2-position of the carbapenem. This synthesis involves a palladium catalysed cross-coupling reaction between a carbapenem triflate and a suitably substituted arylstannane, a process which is described in U.S. patent application Ser. No. 485,096 filed Feb. 26, 1990, hereby incorporated by reference. In order to apply this synthesis, it is first necessary to modify the bromodibenzofuran or bromodibenzothiophene II to the corresponding stannane VIII. This is accomplished by reacting II with t-butyllithium in THF at from −78° to −50° C. followed by the addition of trimethyltin chloride. Alternatively, compound II may be reacted with hexamethylditin in the presence of a palladium(0) catalyst such as tetrakis(triphenylphosphine)-palladium in an inert solvent such as toluene at from 25° C. to 110° C. for from 0.25–24 hours to provide the stannane VIII.

The other starting material for Scheme III is the 2-oxocarbapenam VI. The steps for preparing the 2-oxocarbapenam intermediate VI are well known in the art and are explained in ample detail by D. G. Melillo et al., *Tetrahedron Letters*, 21, 2783 (1980), T. Salzmannn et al., *J. Am. Chem. Soc.*, 102, 6161 (1980), and L. M. Fuentes, I. Shinkai, and T. N. Salzmann, *J. Am. Chem. Soc.*, 108, 4675 (1986). The syntheses are also disclosed in U.S. Pat. No. 4,269,772, U.S. Pat. No. 4,350,631, U.S. Pat. No. 4,383,946 and U.S. Pat. No. 4,414,155 all assigned to Merck & Co., Inc. and hereby incorporated by reference.

Referring to Scheme III, the 2-oxocarbapenam VI is reacted with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in a polar aprotic solvent, such as tetrahydrofuran. An organic nitrogen base, such as triethylamine and the like, is then added to the reaction solution followed immediately by a silylating agent, such as trimethylsilyl trifluoromethanesulfonate to provide intermediate VII. An aprotic polar coordinating solvent, such as DMF, 1-methyl-2-pyrrolidinone and the like, is added. This is followed by the addition of a palladium compound, such as tris(dibenzylideneacetone)dipalladium chloroform, palladium acetate and the like, optionally a suitably substituted phenylphosphine, such as tris(4-methoxyphenyl)phosphine, tris(2,4,6-trimethoxyphenyl)phosphine and the like, and the stannane VIII. A metal halide, such as lithium chloride, zinc chloride and the like, is added and the reaction solution is quickly warmed to a suitable temperature, such as 0° to 50° C., and allowed to stir for a suitable amount of time such as from a few minutes to 48 hours. The carbapenem IX is obtained by conventional isolation/purification methodology known in the art.

Generally speaking, the milder conditions of the synthesis shown in Scheme III allow for a wider range of functional groups $R^a/R^b$ to be present than the synthesis illustrated in Scheme II. The synthesis is also applicable to the oxidized forms of the dibenzothiophene nucleus (i.e., X=SO, SO$_2$). However, in certain cases it is advantageous for the $R^a$ and/or $R^b$ substituent of the stannane VIII to be introduced in a protected or precursory form. Final elaboration of $R^a$ and/or $R^b$ from a precursor substituent, e.g. hydroxymethyl, may be accomplished on carbapenem intermediate IX. Removal of protecting groups then provides the final compound of Formula I. Such final elaboration and deprotection is described in further detail below.

SCHEME III

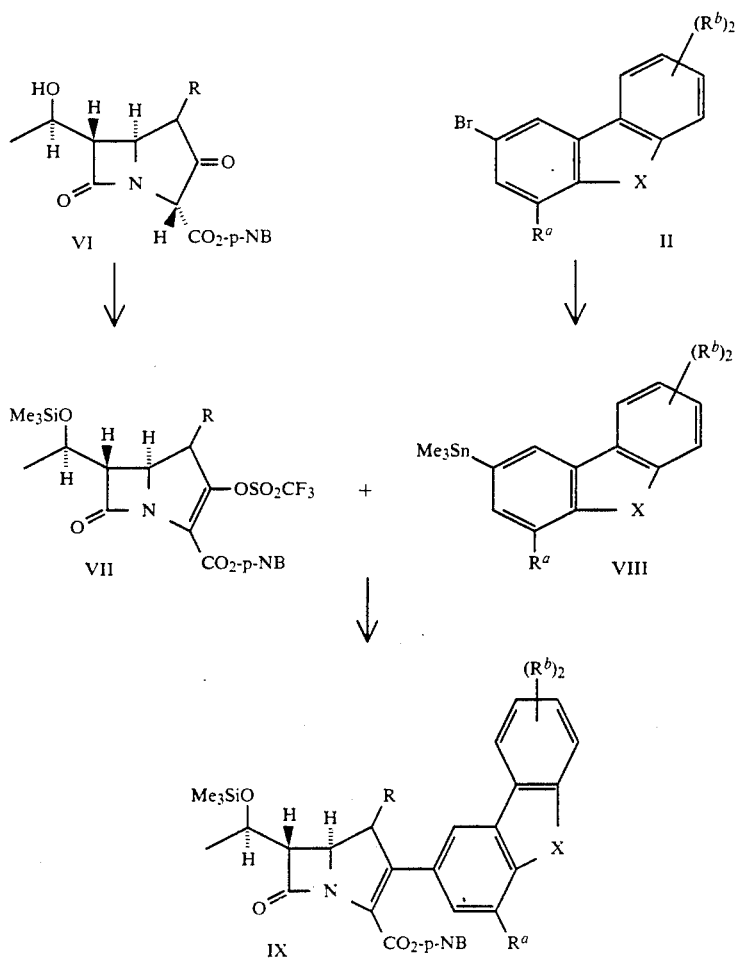

SCHEME III

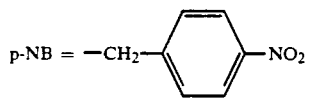

The above reaction Schemes illustrate a particular isomeric attachment of the dibenzofuran or dibenzothiophene nucleus to the carbapenem (defined previously as A). The alternative isomeric attachment (defined previously as B) may be obtained by changing the position of the bromine atom in the side-chain precursor II.

The general synthesis description depicted above in the Schemes shows a protected 1-hydroxyethyl substitution on the 6-position of the carbapenem. After final deprotection, a 1-hydroxyethyl substituent is obtained, which is preferred in most cases. However, it has been been found that with certain 2-side-chain selections, the ultimate balance of favorable properties in the overall molecule may be enhanced by selection of the 6-(1-fluoroethyl) moiety instead. Preparation of 6-(fluoroalkyl) compounds within the scope of the present invention is carried out in a straightforward manner using techniques well known in the art of preparing carbapenem antibacterial compounds. See, e.g., J. G. deVries et al., *Heterocycles*, 23 (8), 1915 (1985); BE 900 718 A (Sandoz) and Japanese Patent Pub. No. 6-0163-882-A (Sanruku Ocean).

Preferred Type I. a) substituents include:

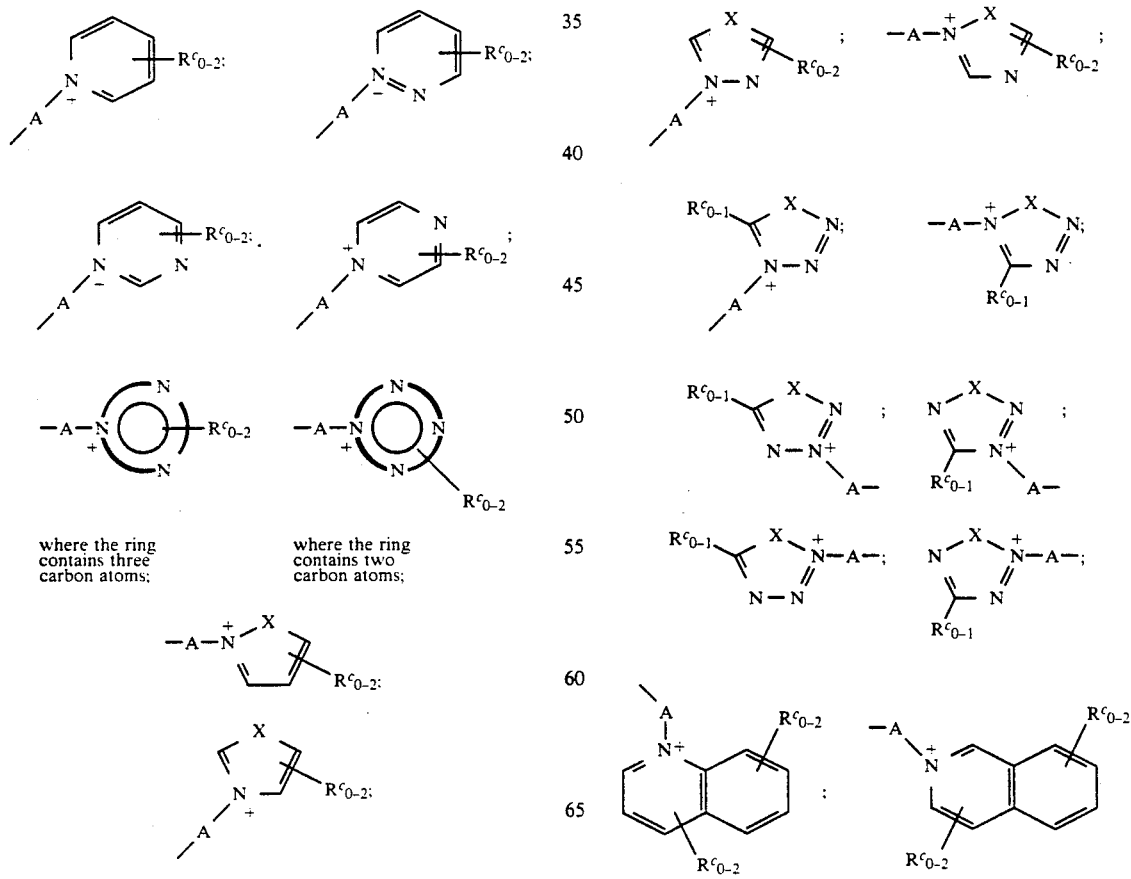

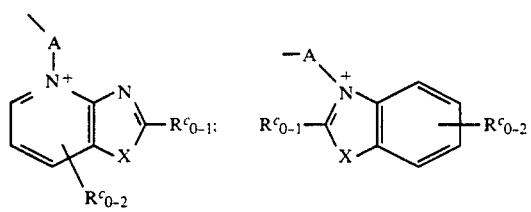

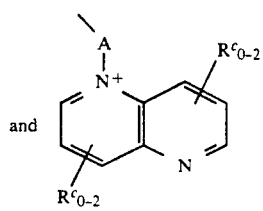

where X=O, S, or NR$^c$. For structures of Type I. a), where R$^c$ is shown to have an indefinite position, it may be attached to any carbon of the ring.

Preferred type I.b) substituents include:

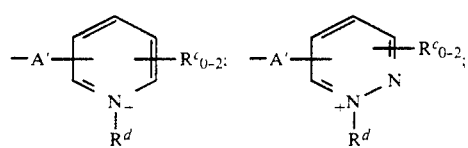

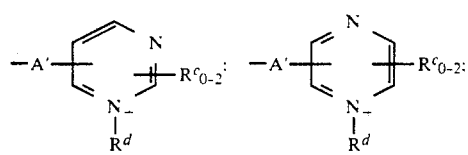

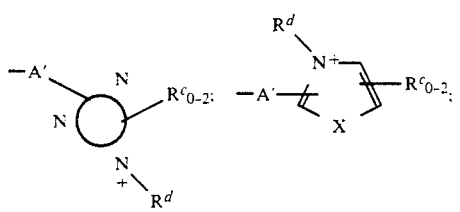

where the ring contains three carbon atoms

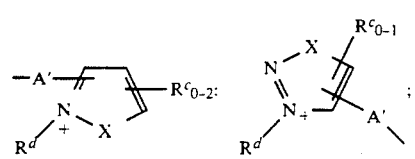

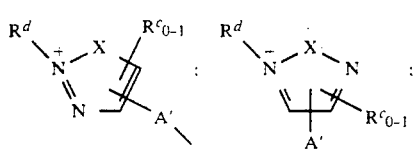

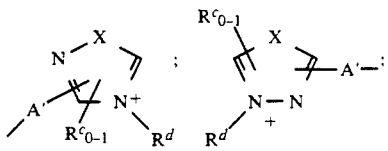

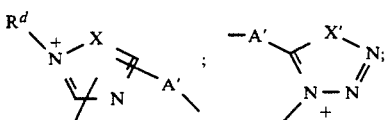

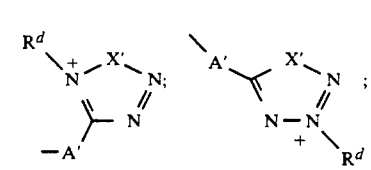

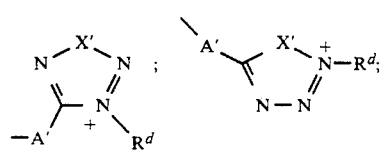

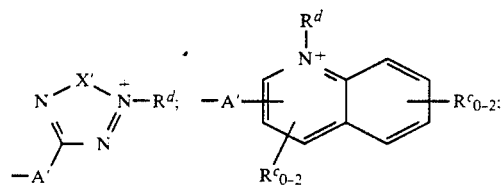

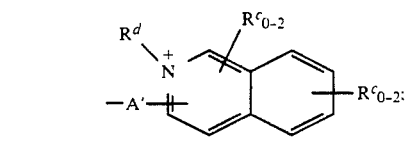

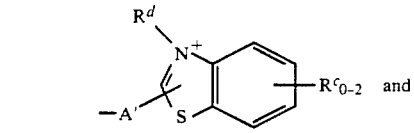

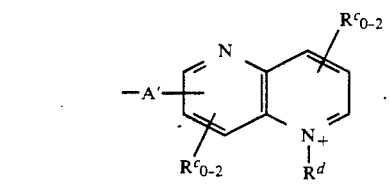

where X=O, S, or NR$^c$ and X'=O or S. For structures of type I. b), where R$^c$ and/or A' are shown to have indefinite positions, they may be independently attached to any carbon atom of the ring.

Preferred type I. c) substituents include:

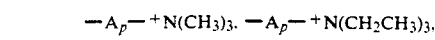

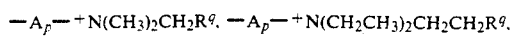

-continued

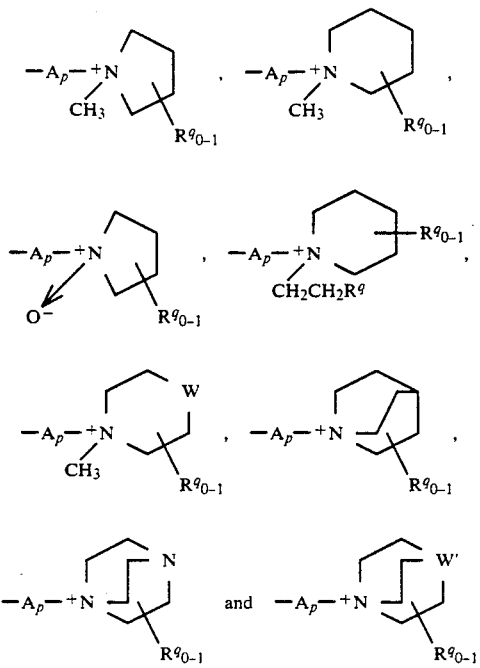

where W is O, S, $NR^e$, $N(O)R^e$, SO, $SO_2$ or $N^+(R^e)_2$ and W" is $N^+R^e$ or NO. For structures of Type I.c), where $R^q$ is shown to have an indefinite position, it may be attached to any carbon atom of the ring.

Preferred type I. d) substituents include:

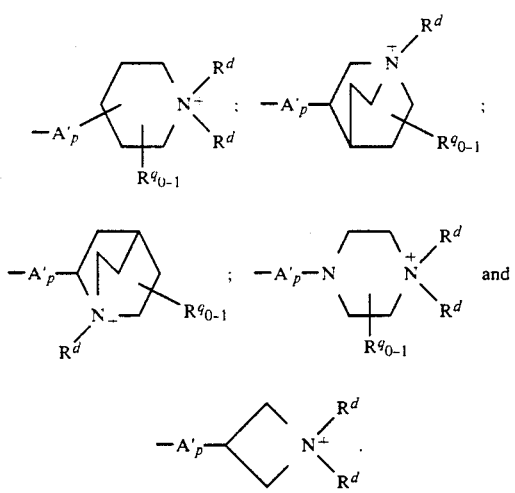

For structures of Type I.d), where $R^q$ and/or $A'_p$ is shown to have an indefinite position, it may be attached to any carbon atom of the ring.

The $R^c$ substituents herein are intended to represent suitable further substituents on the Type I. a) or b) substituents for the dibenzo ring. As seen above, these Type I. a) or b) substituents are monocyclic or bicyclic aromatic groups containing heteroatoms. Given this class of primary substituent, further suitable substituents may be readily discovered in the carbapenem art. For example, suitable substituents for Type I. a) or b) substituents are generally taught in U.S. Pat. No. 4,729,993 assigned to Merck and Co. or in U.S. Pat. No. 4,746,736 assigned to Bristol-Myers Co. These patents are hereby incorporated by reference.

Broadly, $R^c$ may be the same or different and may be selected on an independent basis from the group as defined above. While a single such substitution is preferred, there is occasion to use up to two such substituents on an $R^a$ or $R^b$, e.g., where it is desired to enhance the effect of a particular substituent group by employing multiple substituents. The particular choice of $R^c$ will depend upon the situation. For instance, a specific $R^c$ may lend particular stability to a nitrogen cation. At other times it may be desired to employ a substituent known to enhance antibacterial activity of the overall molecule against a particular bacterium, for example, while also employing a substituent known to improve some other property such as water solubility or the duration of action of the overall molecule.

The scope of $R^c$ herein includes two specific types of further substituent attached to the Type I. a) or b) substituent. A first type of $R^c$ are those attached to a ring carbon and a second type of $R^c$ are those attached to a neutral ring nitrogen. Persons skilled in the art will readily recognize that a wide range of organic substituents are suitably used as $R^c$. Persons skilled in the art will also recognize that some substituents including the $—NR^yR^z$ substituents, useful for one purpose of $R^c$, i.e. carbon substitution, are not equally useful in the other, i.e. nitrogen substitution.

Preferred $R^c$ attached to ring carbon atoms are $—NH_2$, $—SCH_3$, $—SOCH_3$, $—CH_2OH$, $—(CH_2)_2OH$, $—OCH_3$, $—COOM^b$, $—CH_2COOM^b$, $—CH_2CH_2COOM^b$, $—CH_2SOCH_3$, $—CH_2SCH_3$, $—SO_3M^b$, $—CH_2SO_3M^b$, $—CH_2CH_2SO_3M^b$, $—Br$, $—Cl$, $—F$, $—I$, $—CH_3$, $CH_2CH_3$, $CH_2CONH_2$ and $CH_2CON(C_1-C_4alkyl)$ where $M^b$ is defined above. Preferred $R^c$ attached to neutral ring nitrogen atoms are $—CH_2OH$, $—(CH_2)_2OH$, $—CH_2COOM^b$, $—CH_2CH_2COOM^b$, $—CH_2SOCH_3$, $—CH_2SCH_3$, $—CH_2SO_3M^b$, $—CH_2CH_2SO_3M^b$, $—CH_3$, $CH_2CH_3$, $CH_2CONH_2$ and $CH_2CON(C_1-C_4alkyl)$ where $M^b$ is defined above.

It is preferred that each Type I. a) or b) substituent have no more than two $R^c$ substituents which are other than hydrogen. Thus, the formula shown above for Type I. a) substituents has up to two $R^c$ substituents with the remainder of course being hydrogen. Further, the formula for the Type I. b) substituent also allows up to two $R^c$. In accordance with these formulae, the previously listed more specific structures should be interpreted to have no more than two $R^c$ for each monocyclic or bicyclic group. Similarly for Type I. c) or d) substituents it is preferred that any monocyclic or bicyclic group have no more than a single $R^q$ substituent.

The scope of $R^d$ includes a single type of further substituent attached a Type I. b) or d) substituent. The $R^d$ substituents are attached to a cationic nitrogen which may or may not be aromatic. Preferred $R^d$ attached to cationic nitrogen atoms are hydrogen, $—CH_3$, $CH_2CH_3$, $—CH_2CH_2CH_3$, $—CH_2COOM^b$, $—CH_2SO_3M^b$, $—NH_2$ and $O^{(-)}$, where $M^b$ is defined above.

The formulas depicting Type Ib, Ic, and Id substituents show positively charged states for those substituents. It is understood that certain of those substituents, which are cationic by virtue of having a protonating hydrogen atom attached to the nitrogen, may also exist or be produced under certain conditions as a neutral substituent by virtue of the absence of such a hydrogen atom (i.e. in Type Ib, when there is no $R^d$; in type Ic, when there is no $R^w$; and in Type Id, when there is zero or one $R^d$, depending on the type of heterocycle). Whether such a Type Ib, Ic, or Id substituent will be predominately cationic or neutral in a given physical state will be governed by principles of acid-base chemistry, which are well known to those skilled in the art. For example, the particular ratio of neutral form to cationic form will depend upon the basicity of the amine and acidity of a solution. When such a substituent is in a protonated quaternized state, the compound exists as a zwitterion which is internally balanced as to charge or as an ammonium salt which is externally balanced. In illustration, if there is no $R^d$ on a Type Ib substituent, it is understood that such a substituent is neutral (there is no positive charge on the nitrogen). A compound containing such a substituent is typically produced in this form as a salt, wherein M is an alkali metal, and may exist in solution in its neutral form. However, depending upon conditions, a compound containing a neutral Type Ib substituent may be in equilibrium with, and may also be represented by a formula showing, the corresponding compound containing the quaternized protonated substituent where $R^d$ is present and is a hydrogen atom. Furthermore, the same compound may exist with the Type Ib substituent in a completely protonated quaternized form, for instance in an aqueous solution in the presence of a stoichiometric amount of a strong mineral acid. It is intended herein that both the protonated (cationic) and the unprotonated (neutral) forms of Type Ib, Ic and Id substituents of the type just described are within the scope of the present invention.

Suitable A spacer moieties include $-CH_2-$, $-CH_2CH_2-$, $-CH_2CH_2CH_2-$, $-CH_2CH_2CH_2CH_2-$, $-OCH_2CH_2-$, $-SOCH_2-$, $-SO_2CH_2-$, $-SCH_2CH_2-$, $-SOCH_2CH_2-$, $-SO_2CH_2CH_2-$, $-NHCH_2CH_2-$, $-N(CH_3)CH_2CH_2-$, $-CH_2N(CH_3)CH_2CH_2-$, $-CONHCH_2CH_2-$, $-SO_2NHCH_2CH_2-$, $-COCH_2-$, $-CH=CHCH_2-$ and $-CH_2OCH_2CH_2-$. Preferably, where Q is O, S, NH or $N(C_{1-4}alkyl)$, then n is 2-6.

Suitable A' are listed for A above. Further A' may suitably be $-O-$, $-S-$, $-NH-$, $-SO_2-$, $-SO_2NH-$, $-CONH-$, $-CH=CH-$, $-CH_2S-$, $-CH_2NH-$, $-CONHCH_2-$ or $-SO_2NHCH_2-$.

The Type I. cationic substituents are generally added to the dibenzofuran or dibenzothiophene ring following attachment of said aromatic ring to the carbapenem. Conveniently, the dibenzofuran or dibenzothiophene side-chain should be synthesized with a precursor substituent which may be elaborated into the desired cationic substituent. The identity of the precursor substituent will vary according to the particular $R^a$ and $R^b$ desired. For example, one such precursor substituent is $-A-OH$, such as hydroxymethyl.

The hydroxymethyl precursor substituent may be elaborated into cationic substituents of Type I.a) by converting the hydroxyl into an active leaving group such as an iodide (giving $-A-I$) followed by reaction with a desired nitrogen containing aromatic compound. More particularly, two alternative procedures may be utilized to produce a leaving group on the moiety $-A-$ and subsequently to replace such a leaving group with cationic substituents of the type just described.

For a first procedure, the hydroxyl group of $-A-OH$ may be converted to a methanesulfonate group by treating with methanesulfonyl chloride in the presence of triethylamine. A suitable solvent, e.g., dichloromethane, is employed and the reaction is carried out at reduced temperatures. In turn, the methanesulfonate intermediate may converted to the reactive iodide derivative by treatment with sodium iodide in a suitable solvent, e.g., acetone, at reduced or ambient temperatures. Alternatively, the hydroxyl group may be directly converted into the iodide group by common methods known to the art. For example, treatment of the hydroxyl group with methyl triphenoxyphosphonium iodide in a suitable solvent, such as dimethylformamide, at reduced or ambient temperatures, directly provides the desired iodide. Once the iodide has been formed, the introduction of the cationic substituent is accomplished simply by treating the iodide with the desired nitrogen containing compound, e.g. a heteroaromatic compound such as pyridine. The reaction will proceed in a suitable solvent, such as acetonitrile, at or about room temperature. This displacement reaction may also be facilitated by the addition of excess silver trifluoromethanesulfonate to the reaction mixture, in which case reduced temperatures are often desirable.

For a second procedure, the hydroxyl group of $-A-OH$ may be converted into the reactive trifluoromethanesulfonate (triflate) group. However, such an activating group cannot be isolated by conventional techniques but may be formed and used in situ. Thus, treatment of the hydroxyl group with trifluoromethanesulfonic (triflic) anhydride in the presence of a hindered, non-nucleophilic base such as 2,6-lutidine, 2,4,6-collidine, or 2,6-di-tert-butyl-4-methylpyridine in a suitable solvent, such as dichloromethane, at reduced temperatures provides for the generation of the triflate activating group. Introduction of the cationic group is then accomplished by reacting the above triflate in situ with the desired nitrogen containing compound at reduced temperature. In certain cases it is possible and desirable to use the reacting nitrogen containing compound as the base for the formation of the triflate activating group. In this case treatment of the hydroxyl group with triflic anhydride in the presence of at least two equivalents of the reacting nitrogen compound under the conditions described above provides the cationic substituent.

Where the cationic substitution has a substituent $R^c$, the most facile method of providing such a substituent is to employ as the reactant in the preparation methods described above a nitrogen containing compound which already has the desired substituent. Such substituted compounds are readily available starting materials or may be prepared in a straight-forward manner using known literature methods.

The Type I.b) cationic substituents are prepared by quaternization of an aromatic ring nitrogen of a neutral precursor substituent on the dibenzofuran or dibenzothiophene ring. Examples of neutral precursor substituents are $-CONHCH_2-$(2-pyridyl), $-CONHCH_2-$(4-pyridyl) or $-SO_2CH_2-$(4-pyridyl). Quaternization is accomplished by reacting the nitrogen compound in an inert organic solvent (e.g. $CH_2Cl_2$) at about 0° C. to room temperature with an alkylating agent $R^d$-Y where $R^d$ is given above and Y is a leaving group such as iodide, bromide, mesylate (methanesulfonate), tosylate (p-toluenesulfonate) or triflate. Alternatively, the aromatic ring nitrogen may be quaternized by reaction with an oxidizing agent such as 3-chloroperbenzoic acid (giving the N-oxide) or an aminating reagent such as o-(2,4,6-triisopropylbenzenesulfonyl)hydroxylamine (giving the N-amino derivative) in a suitable solvent (e.g. dichloromethane or $CH_3CN$) at about room temperature. In addition, the neutral precursor substituent may be rendered cationic through protonation of the basic aromatic ring nitrogen. This may be accomplished by treatment of the neutral precursor with a suitable inorganic or organic acid, e.g. hydrochloric acid, phosphoric acid, hydrobromic acid, acetic acid or benzoic acid. Protonation may further be accomplished by a carboxylic acid function elsewhere in the molecule, including the C-3 carboxyl on the carbapenem. The neutral precursor substituent may be already attached to the dibenzofuran or dibenzothiophene ring at the time of its connection to the carbapenem, or it may be elaborated from a simpler precursor after connection to the carbapenem. An example of a precursor substituent for elaboration is —A'—OH such as hydroxymethyl. In one suggested synthesis, the hydroxyl may be converted to a reactive leaving group such as iodo as described above. The iodide is then reacted in a nucleophilic displacement reaction with a nitrogen containing aromatic compound which has a nucleophilic substituent such as mercapto or amino. In this displacement reaction, it is the side-chain substituent that is the reacting nucleophile and not the aromatic ring nitrogen. Suitable substrates for this reaction include 2-(mercaptomethyl)pyridine, 2-aminopyridine, 2-(aminomethyl)pyridine or 4-(mercaptomethyl)pyridine. The reaction is carried-out in an inert organic solvent, e.g. methylene chloride, at from about 0° C. to room temperature in the presence of a non-nucleophilic base such as triethylamine or diisopropylethylamine. Quaternization or protonation of the aromatic ring nitrogen as described above then gives the Type I.b) cationic substituent. A second suggested synthesis of a Type I.b) cationic substituent starting from a precursor —A'—OH (e.g. hydroxymethyl) consists of oxidation of the alcohol functionality to an aldehyde followed by Wittig-type olefination with an appropriate nitrogen-containing aromatic substituted reagent, and finally quaternization. The oxidation may be conveniently accomplished by a Swern oxidation employing oxalyl chloride-dimethylsulfoxide followed by triethylamine. The reaction is conducted in methylene chloride as a solvent at from −70° C. to 0° C. The Wittig reaction is carried-out by reacting the aldehyde with the desired Wittig reagent in a polar solvent such as acetonitrile or dimethylsulfoxide at about room temperature. Suitable Wittig reagents include: pyridylmethylenetriphenylphosphorane, quinolylmethylenetriphenylphosphorane, and thiazolylmethylenetriphenylphosphorane. Quaternization or protonation as described above then completes the synthesis of the Type I.b) cationic substituent. Depending on the particular $R^a$ or $R^b$ of Type I.b) that is desired, many other synthesis schemes may be employed, as would be apparent to an organic chemist skilled in the art.

The Type I.c) cationic substituents may be prepared in an analogous manner to that described for I.a) substituents except that the nitrogen containing compound employed in the displacement reaction is an aliphatic amine (i.e. $NR^yR^zR^w$). However, in cases where the amino group is directly bonded to the dibenzofuran or dibenzothiophene nucleus (i.e. $-A_pN^+R^yR^zR^w$ where p=0) the amine is most conveniently attached to the aromatic ring prior to its incorporation into the carbapenem system. If such an amine is primary or secondary, it may require protection with a suitable amine protecting group during the steps employed to attach the dibenzofuran or dibenzothiophene ring to the carbapenem. Tertiary amines require no protection and may be quaternized or protonated as described for the Type I.b) cationic substituents.

The Type I.d) cationic substituents are prepared by quaternization or protonation of a non-aromatic ring nitrogen of an appropriate neutral precursor substituent on the dibenzofuran or dibenzothiophene ring. Quaternization or protonation is accomplished as described above for the Type I.b) substituents. As with the Type I.b) substituents, the neutral precursor may already be attached to the dibenzofuran or dibenzothiophene ring at the time of its connection to the carbapenam, or the neutral precursor may be elaborated from a simpler precursor substituent on the aromatic ring after its connection to the carbapenem. Examples of neutral precursor substituents are: —CONH(3-quinuclidinyl), —CONH[4-(N-methylpiperidinyl)], —SO₂CH₂CH₂[2-(N-methylpyrrolidinyl)], —SO₂[1-(4-methylpiperazinyl)], and —CH₂[1-(4-methylpiperazinyl)]. Elaboration of the neutral precursor substituent from a simpler substituent such as hydroxymethyl may be accomplished in an analogous manner to that described previously for the Type I.b) substituents by employing appropriate reagents to introduce the Type I.d) non-aromatic ring nitrogen moiety which is subsequently to be quaternized or protonated.

Among preferred $R^a$ and $R^b$ of Type II are $C_{1-4}$ alkyl mono-substituted with hydroxy, such as, hydroxymethyl; formyl; carboxy, such as —COOK; carbamoyl, such as —CONH₂; hydroximinomethyl, such as —CH=NOH; or cyano.

In regard to this preferred substitution, the hydroxymethyl may be obtained in any of positions 1, 5, 6, 7, or 8 of the dibenzofuran or dibenzothiophene ring by employing the appropriately substituted starting material II in Scheme II.

The preferred formyl substitution on the dibenzofuran or dibenzothiophene ring may be obtained from the hydroxymethyl substitution just described by a Swern oxidation in methylene chloride at from −70° C. to room temperature employing oxalyl chloride-dimethyl sulfoxide followed by triethylamine as the active agent. Alternatively, this oxidation may be conveniently accomplished using N-methylmorpholine-N-oxide and a catalylic amount of tetra-n-propylammonium peruthenate in methylene chloride. Obviously, the position of the resultant formyl substitution will depend upon the position of the starting hydroxymethyl substitution.

The preferred —CH=NOH substitution on the dibenzofuran or dibenzothiophene ring may be conveniently obtained from the formyl substitution just described. This is accomplished simply by exposing the formyl substituted compound to hydroxylamine in an appropriate solvent at room temperature.

The preferred cyano substitution on the aromatic ring may be obtained from the —CH=NOH substitution just described. The —CH=NOH substituted compound is dehydrated with triflic anhydride and triethylamine in a solvent at −70° C.

The preferred —COOK substitution on the dibenzofuran or dibenzothiophene ring may be obtained from a hydroxymethyl-substituted intermediate IV in Scheme II as follows. Compound IV is oxidized with Jones reagent to convert the hydroxymethyl substituent into a carboxylic acid group. The oxidation with Jones reagent may be incompatible with the carbapenem and thus is optimally performed before ring closure. Prior to ring closure, the carboxy is protected as its allyl ester to permit cyclization of the carbapenem. Protection is carried out by alkylating with allyl bromide and triethylamine. Deprotection following cyclization is carried out with palladium catalyzed deallylation in a solution containing potassium 2-ethylhexanoate, as described in McCombie and Jeffrey, *J. Org. Chem.*, 47, 2505 (1983). Deprotection in such a solution yields the desired potassium salt.

The preferred carbamoyl substitution may be obtained by oxidizing a hydroxymethyl-substituted intermediate IV with Jones reagent to the corresponding carboxylic acid as described above. This carboxy is converted to —CONH$_2$ by sequentially contacting with 1-ethyl-3-(3-dimethylaminopropyl)carbodiimide hydrochloride, 1-hydroxybenzotriazole, and ammonia in an organic solvent at room temperature. Substituted amides may of course be obtained by replacing ammonia with the corresponding substituted amine. In contrast to the carboxy substitution, this carbamoyl requires no protection from the conditions of carbapenem cyclization.

The preferred $R^a$ and $R^b$ of Type II just described may also be obtained by employing the synthesis shown in Scheme III. In this case, the synthetic transformations just described may be carried out on intermediate II or VIII (Scheme III) prior to attachment of the dibenzofuran or dibenzothiophene side-chain to the carbapenem or on intermediate IX after such attachment.

In the preparation methods described above, the carboxyl group at the 3-position and the hydroxyl group at the 8-position of the carbapenem remain blocked by protecting groups until the final product is prepared. Deblocking may be carried out in a conventional manner. For compounds prepared according to Scheme II, deprotection may be carried out in a palladium catalyzed reaction in a solution containing potassium 2-ethylhexanoate and 2-ethylhexanoic acid or, alternatively, another suitable nucelophile such as pyrrolidine. Alternatively, for those prepared via Scheme III, deprotection is conducted sequentially. Thus, compound IX is exposed initially to aqueous acidic conditions, acetic acid or dilute HCl or the like, in an organic solvent such as tetrahydrofuran at 0° C. to ambient temperature for from a few minutes to several hours. The resulting desilylated carbapenem may be isolated by conventional techniques, but is more conveniently taken into the final deprotection process. Thus, addition of an inorganic base such as NaHCO$_3$ or KHCO$_3$ and 10% Pd/C followed by hydrogenation provides for the removal of the p-nitrobenzyl protecting group and the formation of the final compound of Formula I.

The overall molecule must be electronically balanced. Since a quaternary nitrogen is present in the compounds of the present invention, a balancing anion must also, in that case, be present. This is usually accomplished by allowing COOM to be COO$^-$. However, where M is, e.g., a pharmaceutically acceptable ester, a counterion (anion) Z$^-$ must be provided, or alternatively, an anionic substituent might be utilized. A counterion must also be provided or additional anionic substituent utilized where there is more than one quaternary nitrogen. Further, it is within the scope of this invention to utilize an anionic substituent where the quaternary nitrogen is already balanced by COOM= COO$^-$. In that case, it will be understood that it is necessary to provide a counterion (cation) for the anionic substituent. However, it is well within the skill of a medicinal chemist, to whom there is available many suitable anionic and cationic counterions, to make such choices.

Listed in Table I are specific compounds of the instant invention where two of $R^a$ and $R^b$ are H, and the third is as shown.

Listed in Table II are specific compounds of the instant invention where only one of the $R^a$ or $R^b$ is H and the other two are as shown. The generic formula for the Table II is the same as for Table I.

Because of the variations at the 1-position of the β-lactam ring (H or CH$_3$) and of the value of X (O, SO and O, S, SO, SO$_2$) each line of Table I and II represents either 4 or 8 species.

TABLE I

[Structure: carbapenem core with dibenzofuran/dibenzothiophene side chain, bearing H, OH, H, H, H or CH$_3$ substituents, COOM, $R^a$, X, $(R^b)_2$ with positions 4, 5, 6, 7, 8, 1 labeled]

| M | $R^a$ or $R^b$ | X |
|---|---|---|
| (−) | 1-CH$_2$N$^+$-C$_6$H$_4$-NH$_2$ | O, SO |
| (−) | 5-CH$_2$N$^+$-C$_6$H$_4$-NH$_2$ | O, SO |
| (−) | 6-CH$_2$N$^+$-C$_6$H$_4$-NH$_2$ | O, SO |
| (−) | 7-CH$_2$N$^+$-C$_6$H$_4$-NH$_2$ | O, SO |
| (−) | 8-CH$_2$N$^+$-C$_6$H$_4$-NH$_2$ | O, SO |
| (−) | 1-CH$_2$N$^+$-C$_6$H$_4$-NH$_2$ | O, SO |
| (−) | 6-CH$_2$N$^+$-C$_6$H$_4$-NH$_2$ | O, SO |

TABLE I-continued

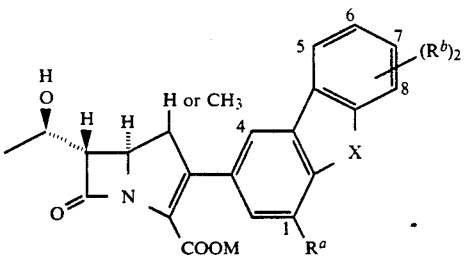

| M | $R^a$ or $R^b$ | X |
|---|---|---|
| (−) | 7-CH$_2$N$^+$(pyridinium)-NH$_2$ (4-amino) | O, SO |
| (−) | 8-CH$_2$N$^+$(pyridinium)-NH$_2$ | O, SO |
| (−) | 5-CH$_2$N$^+$(pyridinium)-NH$_2$ | O, SO |
| (−) | 1-CH$_2$N$^+$(imidazolium)—N—CH$_3$ | O, S, SO, SO$_2$ |
| (−) | 6-CH$_2$N$^+$(imidazolium)—N—CH$_3$ | O, S, SO, SO$_2$ |
| (−) | 7-CH$_2$N$^+$(imidazolium)—N—CH$_3$ | O, S, SO, SO$_2$ |
| (−) | 8-CH$_2$N$^+$(imidazolium)—N—CH$_3$ | O, S, SO, SO$_2$ |
| (−) | 5-CH$_2$N$^+$(imidazolium)—N—CH$_3$ | O, S, SO, SO$_2$ |
| (−) | 7-CH$_2$N$^+$(pyrazolium)—N—CH$_3$ | O, S, SO, SO$_2$ |
| (−) | 7-CH$_2$N$^+$(triazolium)—N—CH$_3$ | O, S, SO, SO$_2$ |
| (−) | 7-CH$_2$N$^+$(pyridinium)-NCH$_2$CONH$_2$ | O, S, SO, SO$_2$ |
| (−) | 7-CH$_2$N$^+$(pyrazolium)-N-CH$_3$ | O, S, SO, SO$_2$ |

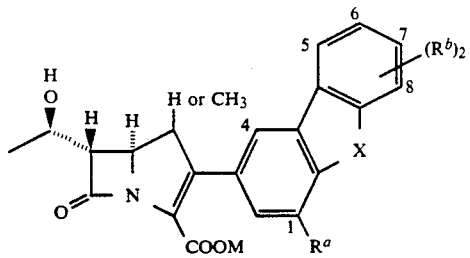

| M | $R^a$ or $R^b$ | X |
|---|---|---|
| (−) | 7-CH$_2$N$^+$(pyridinium)-NCH$_2$SOCH$_3$ | O, S, SO, SO$_2$ |
| K | 7-CH$_2$N$^+$(pyridinium)-NCH$_2$SO$_3^-$ | O, S, SO, SO$_2$ |
| K | 7-CH$_2$N$^+$(pyridinium)-NCH$_2$CO$_2^-$ | O, S, SO, SO$_2$ |
| K | 7-CH$_2$N$^+$(pyridinium)-CH$_2$CH$_2$SO$_3^-$ | O, S, SO, SO$_2$ |
| K | 8-CH$_2$N$^+$(pyridinium)-CO$_2^-$ | O, S, SO, SO$_2$ |
| (−) | 7-CH$_2$N$^+$(pyridinium)-NCH$_2$CH$_2$OH | O, S, SO, SO$_2$ |
| (−) | 7-CH$_2$N$^+$(pyridinium)-NH$_2$ | O, SO |
| (−) | 7-CH$_2$N$^+$(pyridinium)-CH$_2$S(O)CH$_3$, NH$_2$ | O, SO |
| (−) | 8-CH$_2$N$^+$(pyridinium)-CH$_2$OH | O, SO |
| (−) | 7-CH$_2$N$^+$(pyridinium)-CH$_2$OH, NH$_2$ | O, SO |
| (−) | 6-CH$_2$N$^+$H(CH$_3$)$_2$ | O, SO |
| (−) | 1-CO$_2$CH$_2$CH$_2$N$^+$H(CH$_3$)$_2$ | O, SO |

TABLE I-continued

[Structure: bicyclic β-lactam with hydroxyethyl group, COOM, and biphenyl-X substituent bearing R^a at position 1 and (R^b)_2 at positions 6,7,8]

| M | R^a or R^b | X |
|---|---|---|
| (−) | 1-NSO_2CH_2CH_2N^+(imidazole)N−CH_3, H | O, SO |
| (−) | 8-OCH_2CH_2N^+(pyridyl)-NH_2 | O, SO |
| (−) | 1-SCH_2CH_2N^+(pyridyl)-NH_2 | O, SO |
| (−) | 1-SO_2CH_2CH_2N^+(pyridyl)-NH_2 | O, SO |
| (−) | 7-CH_2OCH_2CH_2N^+(pyridyl)-NH_2 | O, SO |
| (−) | 8-CH_2SCH_2CH_2N^+(pyridyl)-NH_2 | O, SO |
| (−) | 7-CH_2S(O)_2CH_2N^+(pyridyl)-NH_2 | O, SO |
| (−) | 8-CH_2CH_2N^+(pyridyl)-NH_2 | O, SO |
| (−) | 7-CCH_2N^+(pyridyl)-NH_2, =O | O, SO |
| (−) | 1-S(O)_2NHCH_2CH_2N^+(pyridyl)-NH_2 | O, SO |
| (−) | 6-S(→O)-CH_2CH_2N^+(imidazole)N−CH_3 | O, SO |
| (−) | 7-C(=O)CH_2-N^+(imidazole)N−CH_3 | O, SO |
| (−) | 1-S(=O)_2CH_2N^+(imidazole)N−CH_3 | O, SO |
| (−) | 7-CH_2S-(pyridinium N^+-NH_2) | O, SO |
| (−) | 7-CH=CH-(pyridinium N^+-CH_3) | O, SO |
| H | 6-N(H)-(2-pyridyl) | O, SO |
| (−) | 1-C(=O)NHCH_2-(pyridinium N^+-CH_3) | O, SO |
| (−) | 1-C(=O)NHCH_2CH_2-(pyridinium N^+-CH_3) | O, SO |
| (−) | 1-S(=O)(=O)N(piperazinium with N^+-CH_3, N-CH_3) | O, SO |

TABLE I-continued

Structure: core bicyclic β-lactam with biphenyl/dibenzofuran-type substituent bearing (R^b)_2 on one ring and R^a on the other, linked via X; carboxylate COOM; hydroxyethyl group.

| M | R^a or R^b | X |
|---|---|---|
| (−) | 1-S(O_2)-CH_2-(N-methylpyridinium) | O, SO |
| (−) | 7-CH_2-(1-methyl-2-amino-pyridinium) | O, SO |
| (−) | 8-CH_2-(pyridinium N-acetamide, N-CH_2-C(O)NH_2) | O, SO |
| K | 1-C(O)NH-CH_2CH_2-(pyridine N-oxide) | O, SO |
| K | 1-SCH_2(O_2)-(pyridine N-oxide) | O, SO |
| (−) | 1-C(O)NH-(N-methyl quinuclidinium) | O, SO |
| (−) | 7-(N-methyl pyrrolidinium) | O, SO |
| (−) | 7-CH_2-(N-methyl morpholinium) | O, SO |
| (−) | 8-CH_2-N(CH_3)_3^+ | O, SO |
| (−) | 7-CH_2-(quinuclidinium) | O, SO |
| K | 8-CH_2-N^+(quinuclidine-1-carboxylate), CO_2^− | O, SO |
| K | 7-CH_2-(morpholine N-oxide) | O, SO |
| (−) | 7-CH_2-N^+(piperazine N-oxide) | O, SO |
| (−) | 1-C(O)NH-CH_2-(1,1-dimethyl piperidinium) | O, SO |
| (−) | 1-(N-methyl pyrrolidinium) | O, SO |
| K | 1-CH_2NH-(2-pyridyl) | O, S, SO, SO_2 |
| K | 6-CH_2NH-(2-pyridyl) | O, S, SO, SO_2 |
| K | 7-CH_2NH-(2-pyridyl) | O, S, SO, SO_2 |
| K | 1-C(O)NHCH_2CH_2-(2-pyridyl) | O, S, SO, SO_2 |
| (−) | 1-C(O)NHCH_2CH_2-(N-methyl pyridinium) | O, SO |

TABLE II

| M | $R^a$ | $R^b$ | X |
|---|---|---|---|
| (—) | CN | 7-CH$_2$N$^+$(=CHCH=CH)NCH$_3$ (imidazolium) | O, S, SO, SO$_2$ |
| (—) | SOCH$_3$ | 7-CH$_2$N$^+$(=CHCH=CH)NCH$_3$ | O, S, SO, SO$_2$ |
| (—) | CO$_2$K | 7-CH$_2$N$^+$(=CHCH=CH)NCH$_3$ | O, S, SO, SO$_2$ |
| (—) | CO$_2$K | 8-CH$_2$N$^+$-pyridinium-NH$_2$ | O, S, SO, SO$_2$ |
| (—) | tetrazole-NK | 7-CH$_2$N$^+$-pyridinium-NH$_2$ | O, S, SO, SO$_2$ |
| (—) | tetrazole-NK | 8-CH$_2$N$^+$-pyridinium, NH$_2$ | O, S, SO, SO$_2$ |
| (—) | SO$_3$K | 8-CH$_2$N$^+$-pyridinium-NH$_2$ | O, S, SO, SO$_2$ |
| (—) | CO$_2$K | 7-N-pyrrolidinium-CH$_3$ | O, S, SO, SO$_2$ |
| (—) | SO$_3$K | 7-N-pyrrolidinium-CH$_3$ | O, S, SO, SO$_2$ |
| (—) | SO$_3$K | 8-CH$_2$-N-pyrrolidinium-CH$_3$ | O, S, SO, SO$_2$ |
| (—) | CHO | 7-CH$_2$N$^+$-pyridinium-NH$_2$ | O, S, SO, SO$_2$ |
| (—) | CONH$_2$ | 7-CH$_2$N$^+$(=CHCH=)N—CH$_3$ | O, S, SO, SO$_2$ |
| (—) | SCH$_3$ | 7-CH$_2$N$^-$(=CHCH=)N—CH$_3$ | O, S, SO, SO$_2$ |

The invention is further defined by reference to the examples below. Unless otherwise indicated, all temperatures are in degrees Celsius.

EXAMPLE 1

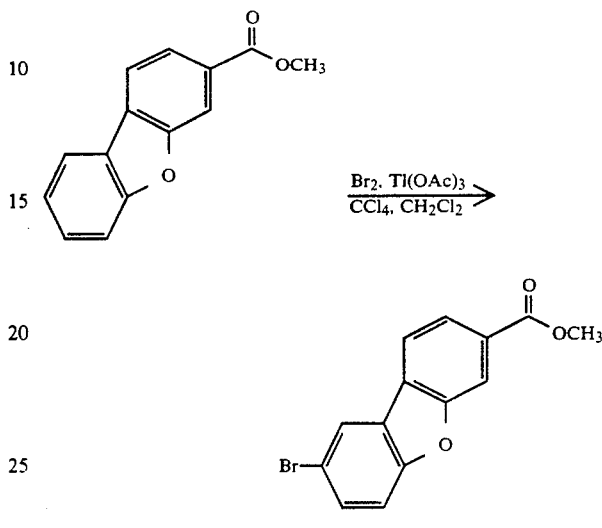

Methyl 3-Bromo-dibenzofuran-7-carboxylate (1)

To a solution of methyl dibenzofuran-2-carboxylate [0.109 g, 0.482 mmol; H. Gilman et. al., J. Amer. Chem. Soc. 61, 2836 (1939)] in carbon tetrachloride (3 ml) and methylene chloride (1.5 ml) at room temperature was added thallium(III) acetate sesquihydrate (58.9 mg, 0.144 mmol). A solution of bromine (76 mg. 0.48 mmol) in 0.5 ml of carbon tetrachloride was added slowly dropwise during 1 hour. After stirring for an additional 2 hours, the mixture was filtered through 30 g of silica gel, eluting with methylene chloride. The filtrate was washed successively with 10% NaHSO$_3$, saturated NaHCO$_3$, H$_2$O, and brine. Drying (MgSO$_4$) and evaporation yielded 102 mg (69%) of the title compound as a yellow solid which was used in the next step without further purification.

$^1$H-NMR (300 MHz, CDCl$_3$): δ3.98 (s, 3H, —OCH$_3$); 7.46 (d, 1H); 7.60 (dd, J=1.96, 8.73, 1H); 7.92 (d, J=8.11, 1H); 8.04–8.10 (m, 2H); 8.22 (s, 1H).

EXAMPLE 2

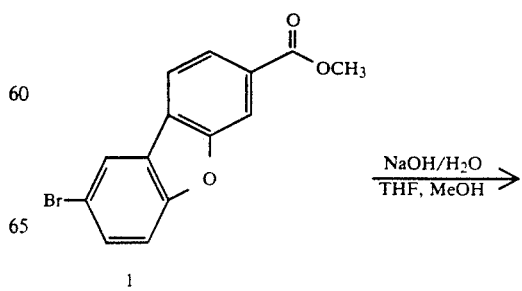

-continued

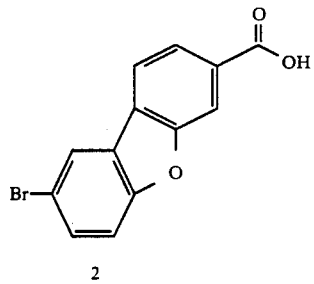

3-Bromo-dibenzofuran-7-carboxylic acid (2)

To a mixture of methyl 3-bromo-dibenzofuran-7-carboxylate (3.2 g, 10.5 mmol) in 2:1 THF:methanol (90 ml) was added 2.5N NaOH (60 ml). After stirring at room temperature for 1 hour, the reaction was complete. Nearly all the THF:methanol was evaporated off and then the mixture was adjusted to pH=1 with concentrated HCl and extracted with ethyl acetate. Drying (MgSO₄) and evaporation yielded 3.1 g (100%) of the title compounds which was used in the next reaction without purification.

$^1$H-NMR (300 MHz, d₆-DMSO): δ7.7–7.76 (m, 2H); 8.01 (dd, J=8.09, 1.34, 1H); 8.20 (bs, 1H); 8.30 (dd, J=8.18, 0.61, 1H); 8.54 (bs, 1H).

EXAMPLE 3

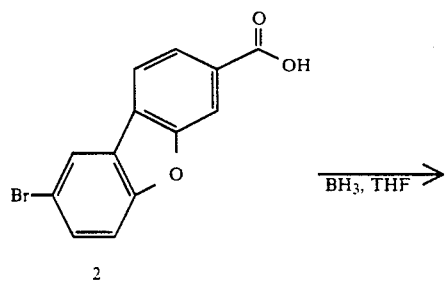

3-Bromo-7-(hydroxymethyl)-dibenzofuran (3)

A cloudy solution of 3-bromo-dibenzofuran-7-carboxylic acid (3.2 g, 10.9 mmol) in 80 ml THF was cooled to 0° C. and a solution of borane in THF (1.0M, 13.0 ml, 13.0 mmol) was added dropwise. The cooling bath was removed and the reaction was stirred at room temperature for 20 hours and was then quenched by the cautious addition of methanol (10 ml). The solution was evaporated to dryness in vacuo and the residue was dissolved in methanol-CH₂Cl₂ (1:1) and again evaporated. After one repetition of this dissolution-evaporated process, 2.74 g (90%) of the title compound was obtained as a brown solid and used in the next reaction without purification.

$^1$H-NMR (300 MHz, CDCl₃): δ4.85 (s, 2H); 7.33 (d, J=6.96, 1H); 7.41 (d, J=8.67, 1H); 7.52 (dd, J=8.76, 2.11, 1H); 7.58 (s, 1H); 7.85 (d, J=8, 1H); 8.03 (d, J=2.02, 1H).

EXAMPLE 4

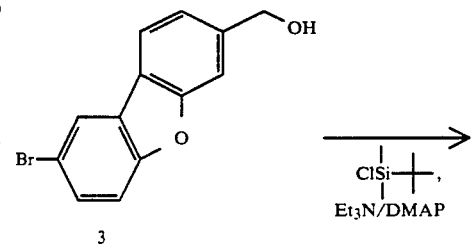

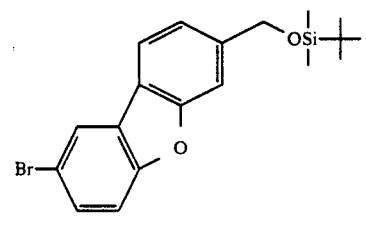

3-Bromo-7-(t-butyldimethylsilyloxymethyl)dibenzofuran (4)

To a solution of 3-bromo-7-hydroxymethyl-dibenzofuran 3 (2.74 g, 9.9 mmol) and t-butyldimethylsilyl chloride (1.93 g, 12.8 mmol) in THF (60 ml) was added triethylamine (1.95 ml, 13.8 mmol) followed by 4-dimethylaminopyridine (120.7 mg, 0.99 mmol). After stirring at room temperature for 20 hours, the solution was poured into ethyl ether (180 ml) and washed successively with saturated NH₄Cl, saturated NaHCO₃, H₂O, and brine. Drying (MgSO₄) and evaporation gave a brown solid which was purified by flash chromatography through 100 g silica gel (10% CH₂Cl₂ hexane) to yield 3.2 g (82%) of the title compound as a pale yellow solid.

$^1$H-NMR (300 MHz, CDCl₃): δ0.11 (s, 6H), 0.953 (s, 9H); 4.88 (s, 2H); 7.26 (d, J=8.60, 1H); 7.41 (d, J=8.67, 1H); 7.5 (dd, J=8.0, 1.89, 1H); 7.56 (s, 1H); 7.82 (d, J=8.0, 1H); 8.02 (d, J=1.96, 1H).

EXAMPLE 5

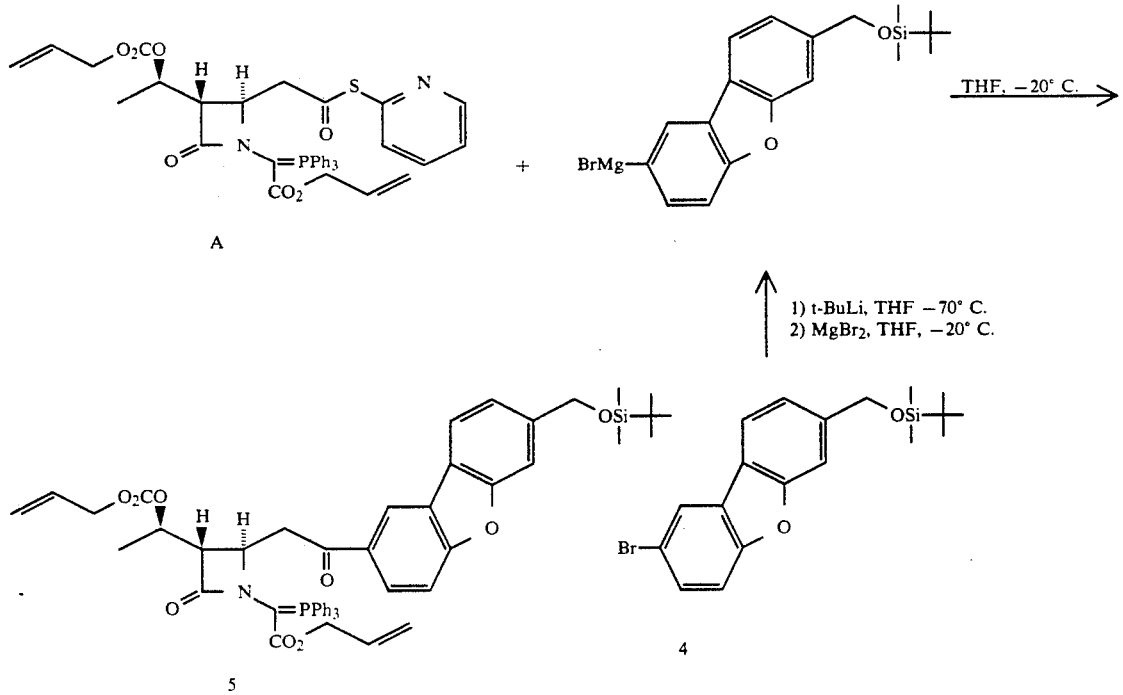

(3S,4R)-1-(allyloxycarbonyltriphenylphosphoranylidene)methyl-3-[1R-(allyloxycarbonyloxy)ethyl]-4-[2-(t-butyldimethylsilyloxymethyl)-6-dibenzofuranylcarbonyl]methyl-azetidin-2-one (5)

A solution of 3-bromo-7-(t-butyldimethylsilyloxymethyl)-dibenzofuran 4 (1.5 g, 3.8 mmol) in THF (12.9 ml) was cooled to −70° C. and a solution of t-butyllithium in pentane (1.7M, 4.47 ml, 7.79 mmol) was added. The solution was warmed to −20° C. over 15 minutes and then a solution of magnesium bromide in THF (0.25M, 16.7 ml) was added generating a reddish color. This Grignard solution was stirred at −20° C. for 20 minutes and was then added dropwise to a −70° C. solution of (3S,4R)-1-(allyloxycarbonyltriphenylphosphoranylidene)methyl-3-[1R-(allyloxycarbonyloxy)ethyl]-4-[(2-pyridylthio)carbonyl]methyl-azetidin-2-one A (2.69 g, 3.80 mmol) in 13 ml in THF and allowed to warm to −20° C. over 20 minutes. The reaction was diluted into ethyl acetate washed successively with saturated NH$_4$Cl, 1N NaOH, H$_2$O, and brine. Drying (MgSO$_4$) and evaporation yielded 3.3 g of a yellow foam which was purified by flash chromatography through 250 g of silica gel (7:3 ethyl acetate:hexane) to yield 1.83 g (50%) of the title compound as a yellow foam.

IR (CHCl$_3$): 1740 ($\beta$-lactam), 1680 (ketone), 1610 cm$^{-1}$ (ylide).

$^1$H-NMR (300 MHz, CDCl$_3$): δ0.13 (s, 6H); 0.96 (s, 9H); 1.15 (d, J=6.22, 3H, CH$_3$).

EXAMPLE 6

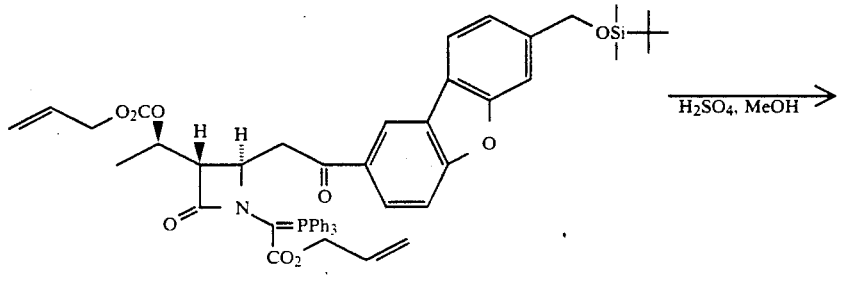

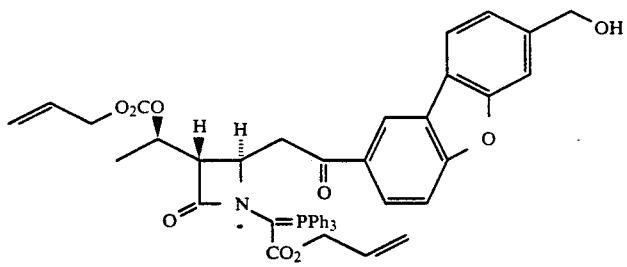

(3S,4R)-1-(allyloxycarbonyltriphenylphosphoranylidene)methyl-3-[1R-(allyloxycarbonyloxy)ethyl]-4-[2-(hydroxymethyl)-6-dibenzofuranylcarbonyl]-methyl-azetidin-2-one (6)

A solution of the silyl ether 6 (1.83 g, 1.9 mmol) in methanol (33 ml) was cooled to 0° C. and 1M H$_2$SO$_4$ (2.85 ml, 2.85 mmol) was added. The reaction was stirred at 0° C. for 1.5 hours, quenched with NaHCO$_3$, diluted into ethyl acetate and washed successively with saturated NaHCO$_3$, water and brine. Drying (MgSO$_4$) and evaporation yielded 1.8 g of a yellow solid which awas pruified by flash chromatography through 200 g silica gel (7:3 ethyl acetate:hexanes) yielding 1.1 g (82%) of the title compound.

IR (CHCl$_3$): 1740 (β-lactam), 1680 (ketone), 1610 cm$^{-1}$ (ylide).

$^1$H-NMR (300 MHz, CDCl$_3$) 1.15 (d, J=6.35, 3H, CH$_3$).

EXAMPLE 7

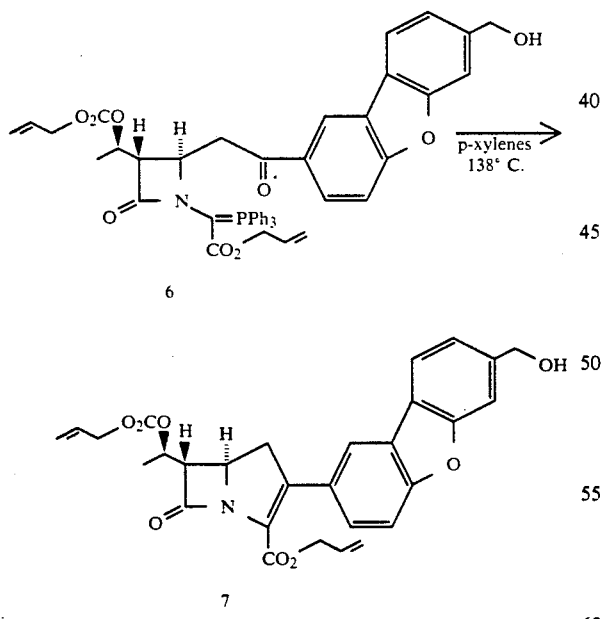

Allyl-(5R,6S)-2-(2-hydroxymethyl-6-dibenzofuranyl)-6-[1R-(allyloxycarbonyloxy)ethyl]carbapen-2-em-3-carboxylate (8)

The phosphorane 6 (0.551 g, 0.693 mmol) was dissolved in p-xylenes (34.6 ml) in the presence of one crystal of hydroquinone and refluxed for 2 hours. Evaporation yielded 540 mg of a yellow solid which was purified by flash chromatography through 50 g silica gel (7:3 ethyl acetate:hexanes) yielding 240 mg (46%) of the title compound as a yellow foam.

IR (CHCl$_3$): 1780 (β-lactam), 1740 (carbonate) 1725 cm$^{-1}$ (ester).

$^1$H-NMR (300 MHz, CDCl$_3$): δ1.48 (d, J=6.41, 3H, -CH$_3$); 3.27-3.33 (m, 2H, Hlab); 3.42 (dd, J=8.39, 2.79, 1H, H6); 4.30 (dt, J=2.74, 9.38, 1H, H5); 4.57-4.75 (m, 4H, —OCH$_2$C=C); 4.82 (s, 2H, —CH$_2$—O); 5.11-5.38 (m, 5H, H8, —C=CH$_2$); 5.77-5.94 (m, 2H, —CH=C); 7.30 (d, J=7.94, 1H); 7.41-7.50 (m, 2H); 7.56 (s, 1H); 7.84 (d, J=8.0, 1H); 7.91 (s, 1H).

EXAMPLE 8

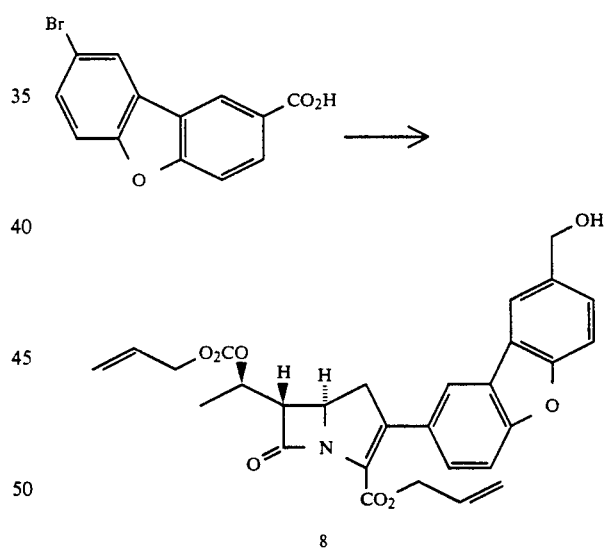

Allyl-(5R,6S)-2-(3-hydroxymethyl-6-dibenzofuranyl)-6-[1R-(allyloxycarbonyloxy)ethyl]carbapen-2-em-3-carboxylate (8)

In an analogous manner to that described in Examples 3-7, but starting with 3-bromo-dibenzofuran-6-carboxylic acid [H. Gilman et. al., J. Amer. Chem. Soc. 61, 2836 (1939)], the title compound was obtained as a yellow foam.

IR (CHCl$_3$): 1780 (β-lactam), 1745 (carbonate), 1720 cm$^{-1}$ (ester)

$^1$H-NMR (300 MHz:CDCl$_3$): δ1.49 (d, J=6.35, 3H, —CH$_3$); 3.31-3.34 (m, 2H, Hla,b); 3.43 (dd, J=8.48, 2.74, 1H, H6); 4.29 (dt, J=2.75, 9.35, 1H, H5); 4.58-4.75 (m, 4H, C=C—CH$_2$O); 4.82 (d, J=5.07, 2H, Ar—CH-

₂O—), 5.13–5.39 (m, 5H, H8, CH₂=C—), 5.79–5.94 (m, 2H, C=CH—); 7.43–7.95 (m, 6H, ArH).

EXAMPLE 9

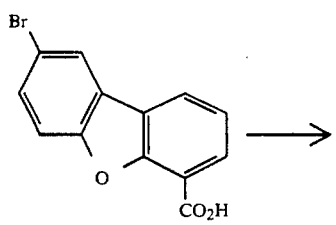

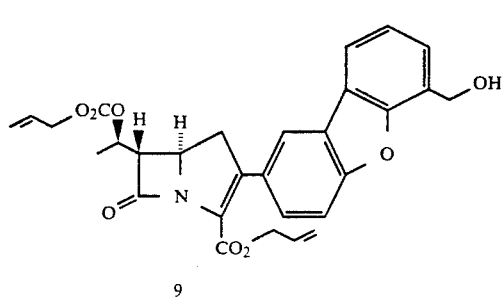

Allyl-(5R,6S)-2-(1-hydroxymethyl-6-dibenzofuranyl)-6-[1R-(allyloxycarbonyloxy)ethyl]carbapen-2-em-3-carboxylate (9)

In an analogous manner to that described in Examples 3–7, but starting with 6-bromo-dibenzofuran-1-carboxylic acid [H. Gilman et. at., J. Amer. Chem. Soc. 61, 643 (1939)], the title compound was obtained as a yellow foam.

IR (CHCl₃): 1780 (β-lactam), 1745 (carbonate), 1720 cm⁻¹ (ester).

¹H-NMR (300 MHz, CDCl₃) δ1.48 (d, J=6.35, 3H, —CH₃); 3.29–3.34 (m, 2H, H1a,b); 3.42 (dd, J=8.36, 2.69, 1H, H6); 4.28 (dt, J=2.44, 9.22, 1H, H5); 4.57–4.70 (m, 4H, C=C—CH₂—); 5.05 (s, 2H, Ar—CH₂O—); 5.12–5.38 (m, 5H, H8, CH₂=C—); 5.77–5.93 (m, 2H, C=CH—); 7.34 (t, J=7.81, 1H); 7.43–7.54 (m, 3H); 7.82 (d, J=7.69, 1H); 7.94 (s, 1H).

EXAMPLE 10

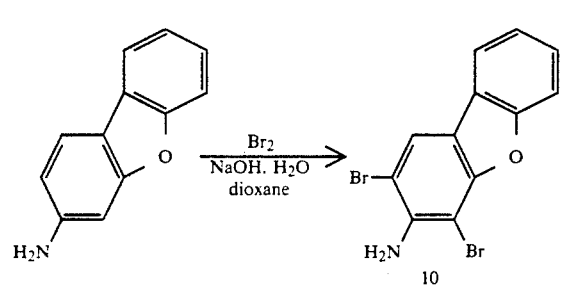

2-Amino-1,3-dibromodibenzofuran (10)

A suspension of 2-aminodibenzofuran [59.3 g, 0.324 mol; H. Gilman and S. Avakian, J. Am. Chem. Soc. 68, 580 (1946)] in 1.3 l of dioxane and 340 ml of 2N sodium hydroxide was cooled to 0° C. Bromine (109 g, 680 mmol) was added dropwise over 1 hour, after which time the reaction mixture had turned very dark and was allowed to stir at room temperature for 1 hour. The solution was then evaporated to a volume of 500 ml and extracted with methylene chloride (2 l). The organic layers were combined, dried over MgSO₄ and filtered through 1 kg of silica gel (methylene chloride), evaporated to dryness and again filtered through 1 kg of silica gel yielding 98 g (89%) of the title compound as a dark solid.

¹H-NMR (300 MHz, CDCl₃): δ4.76 (bs, 2H); 7.21–7.39 (m, 2H); 7.54 (d, J=7.70, 1H); 7.54 (d, J=7.39, 1H); 7.93 (s, 1H).

FAB-MS: M/e=339, 341, 343 (M+).

EXAMPLE 11

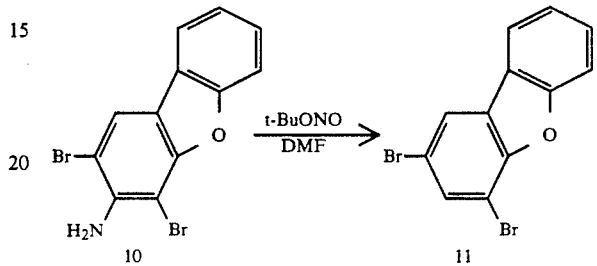

1,3-Dibromodibenzofuran (11)

To a solution of t-butylnitrite (0.89 ml, 7.2 mmol) dissolved in 10 ml of DMF at 50° C. was added dropwise a solution of 2-amino-1,3-dibromodibenzofuran 10 (1.0 g, 2.9 mmol) in 10 ml of DMF with nitrogen evolution. After stirring at 50° C. for 1 hour the reaction was diluted into ether and washed successively with H₂O and saturated NaCl. Drying over MgSO₄ and evaporation gave 1.1 g of a red solid which was purified by flash chromatography through 100 g of silica gel (20% methylene chloride:hexane) yielding 650 mg (68%) of the title compound as a pale orange solid.

¹H-NMR (300 MHz, CDCl₃): δ7.37 (t, J=7.69, 1H); 7.51 (t, J=7.14, 1H); 7.63 (d, J=8.25, 1H), 7.73 (d, J=1.77, 1H); 7.88 (d, J=7.57, 1H); 7.99 (s, 1H).

EI-MS: M/e=324, 326, 328 (M+).

EXAMPLE 12

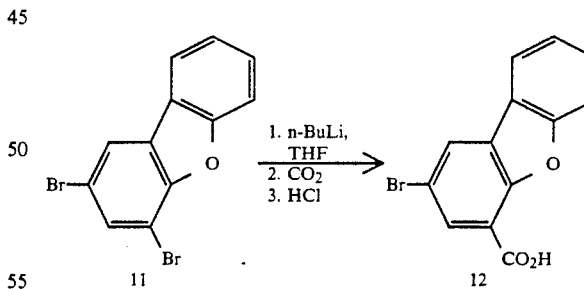

3-Bromodibenzofuran-1-carboxylic acid (12)

A solution of 1,3-dibromodibenzofuran 11 (2.4 g, 7.4 mmol) in 250 ml of THF was cooled to −70° C. and a solution of n-butyllithium in hexane (2.2M, 4.0 ml, 8.8 mmol) was added dropwise generating a red color. The solution was allowed to warm to −50° C. over 30 minutes and then CO₂ gas was bubbled into the reaction mixture for 30 minutes. The cooling bath was removed and after stirring at room temperature for 30 minutes, most of the THF was evaporated off and the reaction mixture was diluted with methylene chloride (1000 ml)

and extracted with sodium hydroxide (1N). The aqueous layer was brought to pH 3 with concentrated hydrochloric acid, and then extracted with methylene chloride (1000 ml). Evaporation of the organic phase gave 2.0 g (91%) of the title compound as a yellow solid which was used without purification.

1H-NMR (300 MHz, d6-Acetone): δ7.49 (t, J=7.4 Hz, 1H); 7.65 (t, J=7.5 Hz, 1H); 7.75 (d, J=8.1 Hz, 1H); 8.19 (d, J=2.1 Hz, 1H); 8.24 (d, J=7.6, 1H); 8.60 (d, J=2.1 Hz, 1H).

FAB-MS: M/e=291, 293 (M+H).

EXAMPLE 13

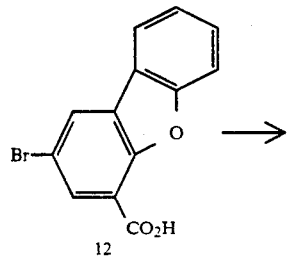

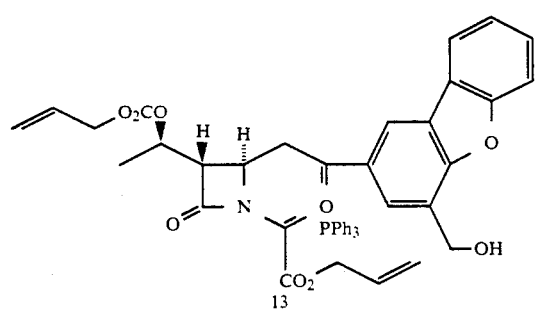

(3S,4R)-1-(allyloxycarbonyltriphenylphosphoranylidene)methyl-3-[1R-(allyloxycarbonyloxy)ethyl]-4-[1-hydroxymethyl-3-dibenzofuranylcarbonyl]-methylazetidin-2-one (13)

In an analogous manner to that described in Examples 3–6, but starting with 3-bromodibenzofuran-1-carboxylic acid 12, the title compound was obtained as a yellow foam.

IR (CHCl$_3$): 1750 (β-lactam); 1665 (ketone); 1620 cm$^{-1}$ (ylide).

EXAMPLE 14

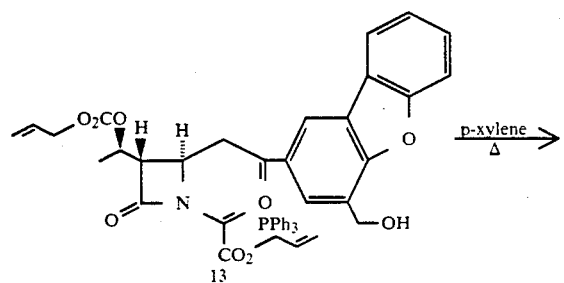

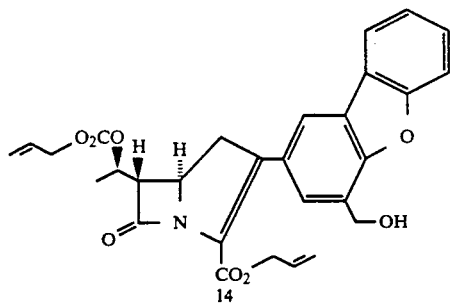

Allyl-(5R,6S)-2-(1-hydroxymethyl-3-dibenzofuranyl)-6-[1R-(allyloxycarbonyloxy)ethyl]-carbapen-2-em-3-carboxylate (14)

In a manner analogous to that described in Example 7, 1.04 g (1.3 mmol) of ylide 13 was cyclized to yield 0.70 g (99%) of the title compound as a yellow oil.

IR (CHCl$_3$): 1780 (β-lactam); 1740 (carbonate); 1720 cm$^{-1}$ (ester).

1H-NMR (300 MHz, CDCl$_3$): δ1.47 (d, J=6.28 Hz, 3H, —CH$_3$); 3.25–3.37 (m, 2H, H1a,b); 3.41 (dd, J=2.7, 8.3, 1H, H6); 4.28 (dt, J=2.7, 9.47, 1H, H5); 4.56–4.73 (m, 4H, C=C—CH$_2$—); 5.01 (d, J=6.05, 2H, Ar—CH$_2$—O); 5.10–5.38 (m, 5H, H8, CH$_2$=C—); 5.77–5.93 (m, 2H, C=CH—); 7.33 (t, J=7.5, 1H); 7.45 (t, J=7.3, 1H); 7.49 (s, 1H); 7.55 (d, J=8.1, 1H); 7.85–7.89 (m, 2H).

EXAMPLE 15

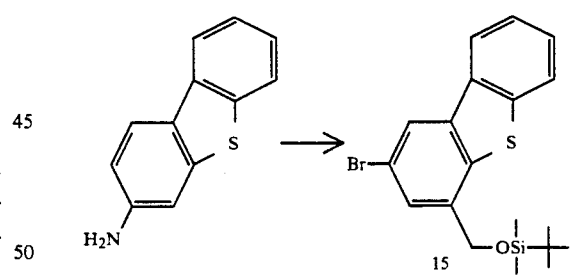

3-Bromo-1-(t-butyldimethylsilyloxymethyl)-dibenzothiophene (15)

In an analogous manner to that described in Examples 10, 11, 12, 3, and 4,2-aminodibenzothiophene [R. K. Brown et al., J. Am. Chem. Soc., 70, 1748 (1948)] was converted to the title compound which was obtained as a yellow solid.

1H-NMR (300 MHz, CDCl$_3$): δ0.19 (s, 6H); 1.01 (s, 9H); 4.91 (s, 2H); 7.4–7.5 (m, 2H); 7.60 (s, 1H); 7.80–7.85 (m, 1H); 8.0–8.1 (m, 1H); 8.13 (d, J=1.8 Hz, 1H).

FAB-MS: M/e=406, 408 (M+).

EXAMPLE 16

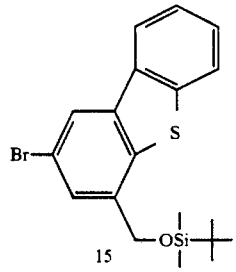 

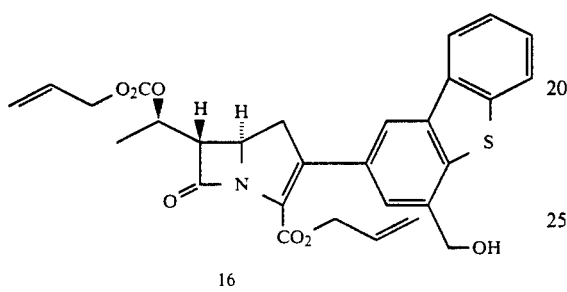

Allyl-(5R,6S)-2-(1-hydroxymethyl-3-dibenzothienyl)-6-[1R-(allyloxycarbonyloxy)ethyl]-carbapen-2-em-3-carboxylate (16)

In an analogous manner to that described in Examples 5–7 but starting with 3-bromo-1-(t-butyldimethylsilyloxymethyl)-dibenzothiophene 15, the title compound was obtained as a yellow foam.

$^1$H-NMR (300 MHz, CDCl$_3$): δ1.48 (d, J=6.41 Hz, CH$_3$); 3.25–3.45 (m, 2H, H1); 3.43 (dd, J=2.8, 8.4 Hz 1H, H6); 4.31 (dt, J=2.8, 9.3 Hz, 1H, H5); 4.55–4.75 (m, 4H, —(CH$_2$C═C); 4.93 (d, J=5.7 Hz, 2H, Ar—CH$_2$—O); 5.1–5.4 (m, 5H, H8, —C═CH$_2$); 5.75–6.0 (m, 2H, —CH═C); 7.4–7.5 (m, 3H); 7.8–7.9 (m, 1H); 8.05–8.15 (m, 2H).

IR (CHCl$_3$): 1780 (β-lactam); 1745 (carbonate); 1720 cm$^{-1}$ (ester).

UV (CH$_3$CN): λ$_{max}$=326 nm (ε=11,600).

EXAMPLE 17

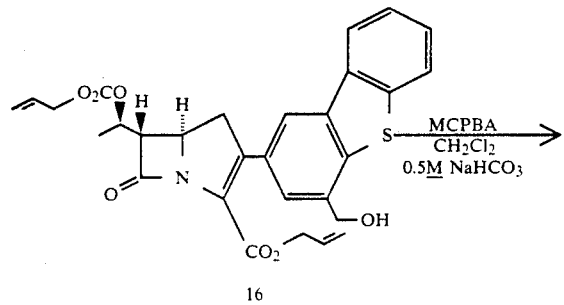

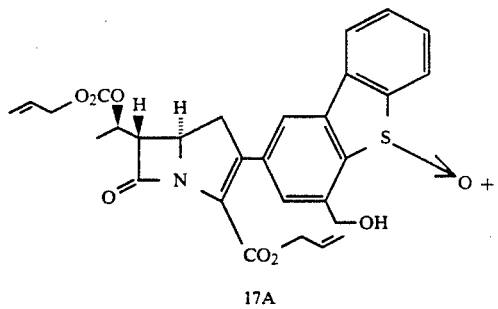

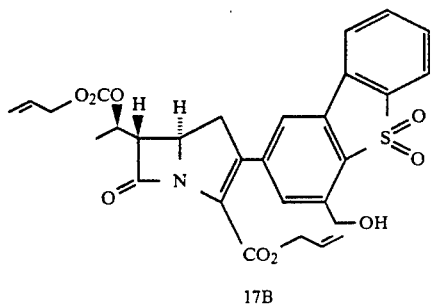

Allyl-(5R,6S)-2-(1-hydroxymethyl-9-oxo-3-dibenzothienyl)-6-[1R-(allyloxycarbonyloxy)ethyl]-carbapen-2-em-3-carboxylate (17A) and allyl-(5R,6S)-2-(1-hydroxymethyl-9,9-dioxo-3-dibenzothienyl)-6-[1R-(allyloxycarbonyloxy)ethyl]-carbapen-2-em-3-carboxylate (17B)

A solution of the carbapenem 16 (272.4 mg, 0.510 mmol) in 5 ml of methylene chloride and 2.5 ml of 0.5M aqueous sodium bicarbonate was cooled to 0° C. and 99% m-chloroperbenzoic acid (115 mg, 0.67 mmol, 1.3 equiv.) was added in one portion. The two-phase reaction mixture was vigorously stirred for 30 minutes and was then quenched with 5% aqueous Na$_2$S$_2$O$_3$ and stirred until a negative starch-iodide test was obtained. The reaction mixture was diluted with ethyl acetate and washed with H$_2$O and brine. Drying over MgSO$_4$ and evaporation gave a yellow oil which was separated by flash chromatography through 30 g of silica gel (EtOAc) to yield 203 mg (72%) of the sulfoxide 17A as a yellow oil and a mixture of the less polar sulfone and unreacted starting material. The latter mixture was further separated by preparative TLC on silica gel (1:1 EtOAc/hexane) to yield 27 mg (9.4%) of the sulfone 17B and 8.5 mg (3.0%) of recovered starting material.

Sulfoxide 17a $^1$H-NMR (300 MHz, CDCl$_3$): δ1.49 (d, J=6.29 Hz, 3H, CH$_3$); 3.20–3.45 (m, 2H, H1); 3.46 (dd, J=2.9, 8.3 Hz, 1H, H6); 4.34 (dt, J=2.9, 9.3 Hz, 1H, H5); 4.55–4.75 (m, 4H, —OCH$_2$C═C); 4.87 (dd, J=9.0, 13.6 Hz, 1H, Ar—CH$_A$—O—); 5.1–5.4 (m, 6H, H8, Ar—CH$_B$—O—, —C═CH$_2$); 5.75–6.0 (m, 2H, —CH═C); 7.37 (d, J=8.2 Hz, 1H); 7.53 (t, J=7.7 Hz, 1H); 7.62 (t, J=7.5 Hz, 1H); 7.7–7.8 (m, 2H); 7.99 (d, J=7.2 Hz, 1H).

Sulfone 7b $^1$H-NMR (300 MHz, CDCl$_3$): δ1.47 (d, J=6.35 Hz, 3H, CH$_3$); 3.25–3.45 (m, 2H, H1); 3.47 (dd, J=2.9, 8.2 Hz, 1H, H6); 4.33 (dt, J32 2.9, 9.4 Hz, 1H, H5);

4.55–4.75 (m, 4H, —OCH$_2$C=C); 5.07 (d, J=6.29, 2H, Ar—CH$_2$O—); 5.1–5.4 (m, 5H, H8, —C=CH$_2$); 5.75–6.0 (m, 2H, —CH=C); 7.52 (bs, 1H); 7.54 (d, J=7.6, 1H); 7.63 (t, J=7 Hz, 1H); 7.70 (s, 1H); 7.73 (d, J=7.6 Hz, 1H); 7.80 (d, J=7.7 Hz, 1H).

EXAMPLE 18

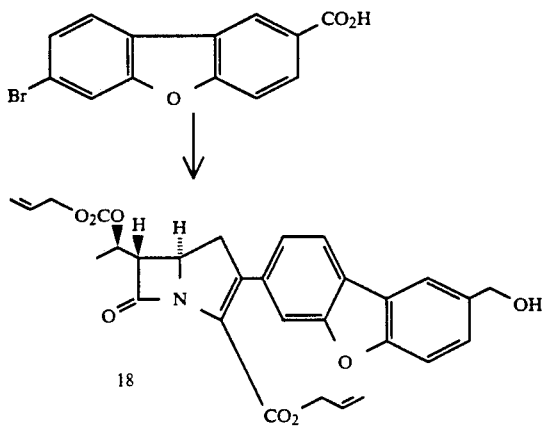

Allyl-(5R,6S)-2-(3-hydroxymethyl-7-dibenzofuranyl)-6-[1R-(allyloxycarbonyloxy)ethyl]-carbapen-2-em-3-carboxylate (18)

In an analogous manner to that described in Examples 2–7, but starting with 7-bromodibenzofuran-3-carboxylic acid, the title compound was obtained as a yellow foam.

$^1$H-NMR (300 MHz, CDCl$_3$): δ1.48 (d, J=6.4 Hz, 3H, CH$_3$), 3.20–3.44 (ABX, 2H, H1), 3.43 (dd, J=2.8, 8.5 Hz, 1H, H6), 4.23 (ddd, J=2.8, 9.2, 9.6, 1H, H5), 4.56–4.78 (m, 4H, —OCH$_2$C=C), 4.82 (s, 2H, ArCH$_2$O—), 5.1–5.4 (m, 5H, H8, —C=CH$_2$), 5.75–6.00 (m, 2H, —CH=C), 7.32 (dd, J=1.5, 8.1 Hz, 1H), 7.45 (dd, J=1.7, 8.5 Hz, 1H), 7.52 (d, J=8.5 Hz, 1H), 7.57 (s, 1H), 7.87 (d, J=8.1 Hz, 1H), 7.93 (s, 1H).

IR (CHCl$_3$): 1775 (β-lactam), 1740 (carbonate), 1725 cm$^{-1}$ (ester).

UV (CH$_3$CN): λmax=320 nm (ε=12,400), 303 nm (ε=13,600).

EXAMPLE 19

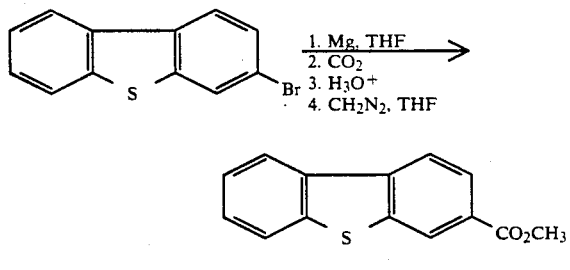

Methyl dibenzothiophene-2-carboxylate (19)

To a mixture of 2-bromodibenzothiophene (6.616 g, 25.14 mmol; H. Gilman and R. K. Ingham, J. Am. Chem. Soc. 75 3843, 1953) and magnesium turnings (0.734 g, 30.2 mmol) in 100 ml of THF was added 1,2-dibromoethane (0.10 ml) and the reaction mixture was sonicated briefly in an ultrasonic bath to initiate the Grignard formation. After stirring at room temperature for 1 hour, the yellow reaction mixture was cooled to $-50°$ C. and carbon dioxide was bubbled through the solution for 20 minutes. During this time the yellow color faded and some precipitate deposited. The reaction mixture was allowed to warm to room temperature and became a nearly colorless solution. The reaction mixture was acidified with 1N HCl, and most of the THF was evaporated in vacuo. The residue was extracted with ethyl acetate, and the resulting organic suspension was washed with water and brine, diluted with toluene, and evaporated in vacuo to give 5.56 g of crude carboxylic acid. The crude product was suspended in 100 ml of THF and excess ethereal diazomethane was added giving a yellow solution. The excess diazomethane was consumed by addition of a small amount of acetic acid, and evaporation in vacuo gave 6.06 g of crude methyl ester. Flash chromatography through 500 g of silica gel (3:2 CH$_2$Cl$_2$/hexane) yielded 4.60 g (76%) of the title compound as a white solid, mp 127°–129° C.

$^1$H-NMR (300 MHz, CDCl$_3$): δ3.96 (s, 3H, OCH$_3$), 7.44–7.54 (m, 2H), 7.83–7.92 (m, 1H), 8.10 (dd, J=1.6, 8.2 Hz, 1H), 8.18 (d, J=8.1 Hz), 8.15–8.22 (m, 1H), 8.55 (d, J=1.6 Hz, 1H). FAB-MS: m/e=243 (M+H).

EXAMPLE 20

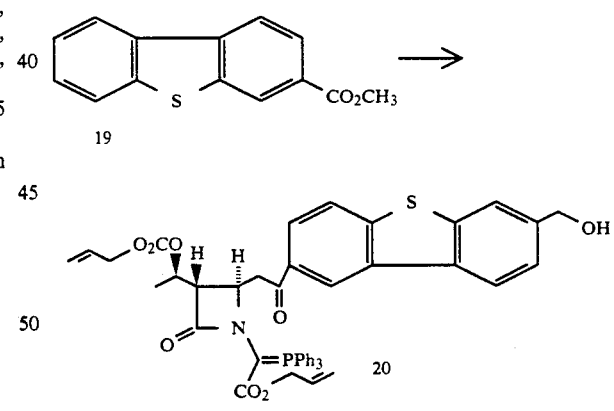

(3S,4R)-1-(allyloxycarbonyltriphenylphosphoranylidene)methyl-3-[1R-(allyloxycarbonyloxy)ethyl]-4-[2-(hydroxymethyl)-6-dibenzothienylcarbonyl]-methylazetidin-2-one (20)

In a manner analogous to that described in Examples 1–6, but starting with methyl dibenzothiophene-2-carboxylate, the title compound was obtained as a yellow foam.

IR (CHCl$_3$): 3450 (hydroxyl), 1745 (ε-lactam), 1680 (ketone), 1610 cm$^{-1}$ (ylide).

EXAMPLE 21

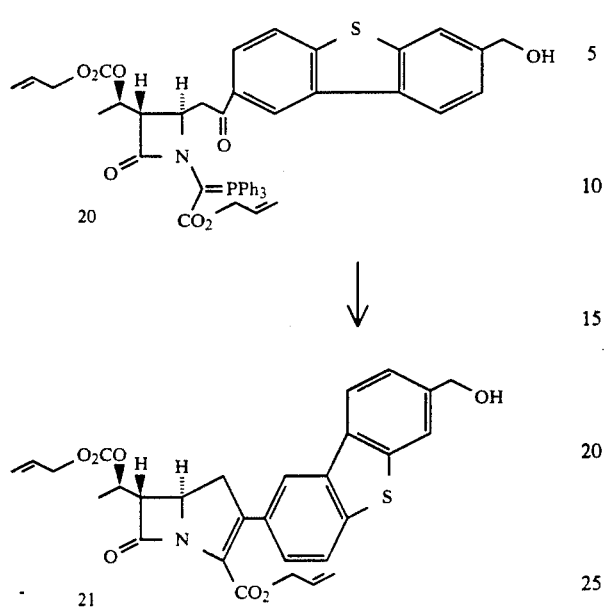

Allyl-(5R,6S)-2-(2-hydroxymethyl-6-dibenzothienyl)-6-[1R-(allyloxycarbonyloxy)ethyl]-carbapen-2-em-3-carboxylate (21)

In a manner analogous to that described in Example 7, 2.396 g (2.952 mmol) of ylide 20 was cyclized to yield 1.337 g (85%) of the title carbapenem as a yellow foam.

$^1$H-NMR (300 MHz, CDCl$_3$): δ1.45 (d, J=6.3 Hz, 3H, CH$_3$), 3.25–3.45 (m, 2H, H1), 3.44 (dd, J=2.8, 8.4 Hz, 1H, H6), 4.32 (ddd, J=2.8, 9.3, 9.5 Hz, 1H, H5), 4.55–4.80 (m, 4H, —OCH$_2$C=C), 4.84 (s, 2H, ArCH$_2$O—), 5.1–5.4 (m, 5H, H8, —C=CH$_2$), 5.75–6.0 (m, 2H, —CH=C), 7.4 (d, J=8.3, 2H), 7.78 (d, J=8.5 Hz, 1H), 7.86 (d, 1H), 8.07 (d, J=8.1 Hz, 1H), 8.13 (d, 1H).

IR (CHCl$_3$): 1780 (β-lactam), 1745 (carbonate), 1725 cm$^{-1}$ (ester).

UV (CH$_3$CN): λmax=316 nm (ε=9,200), 292 nm (ε=12,000), 239 nm (ε=32,000).

EXAMPLE 22

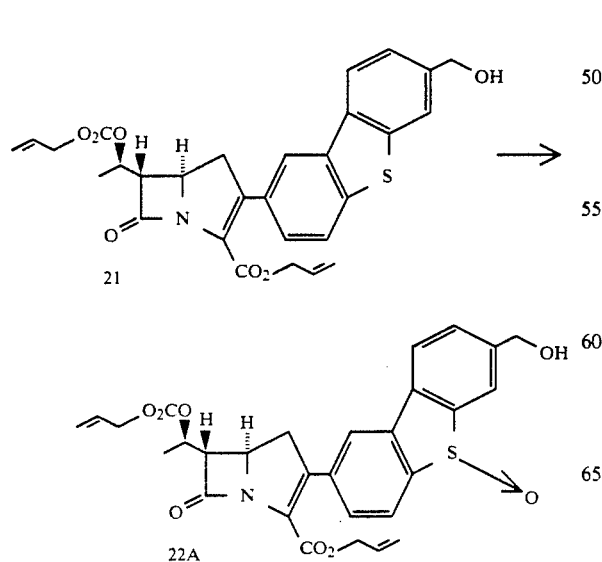

Allyl-(5R,6S)-2-(2-hydroxymethyl-9-oxo-6-dibenzothienyl)-6-[1R-(allyloxycarbonyloxy)ethyl]-carbapen-2-em-3-carboxylate (22A) and
allyl-(5R,6S)-2-(2-hydroxymethyl-9,9-dioxo-6-dibenzothienyl)-6-[1R-(allyloxycarbonyloxy)ethyl]-carbapen-2-em-3-carboxylate (22B)

In a manner analogous to that described in Example 17, but starting with the carbapenem 21 (1.509 g, 2.827 mmol), the sulfoxide 22A (803.4 mg, 52%) and the sulfone 22B (119.2 mg, 7.5%) were prepared.

Sulfoxide 22A $^1$H-NMR (300 MHz, CDCl$_3$): δ1.45 (d, J=6.4 Hz, 3H, CH$_3$), 3.1–3.4 (m, 2H, H1), 3.4–3.5 (m, 1H, H6), 4.29 (br t, J=9.4 Hz, 1H, H5), 4.50–4.75 (m, 6H, —OCH$_2$C=C, —OCH$_2$Ar), 5.1–5.4 (m, 5H, H8, —C=CH$_2$), 5.75–6.00 (m, 2H, —CH=C), 7.3–7.5 (m, 2H,) 7.59 (dd, J=2.4, 7.9 Hz, 1H), 7.71 (s, 1H), 7.75–7.90 (m, 2H).

Sulfone 22B $^1$H-NMR (300 MHz, CDCl$_3$): δ1.47 (d, J=6.2 Hz, 3H, CH$_3$), 3.21 (dd, J=10, 18.2 Hz, 1H, H1), 3.35 (dd, J=9.0, 18.2 Hz, 1H, H1), 3.47 (dd, J=2.8, 8.1 Hz, 1H, H6), 4.32 (ddd, J=2.8, 9.0, 10 Hz, 1H, H5), 4.55–4.75 (m, 4H, —OCH$_2$C=C), 4.73 (bs, 2H, —OCH$_2$Ar), 5.1–5.4 (m, 5H, H8, —C=CH$_2$), 5.75–6.00 (m, 2H, —CH=C), 7.40 (d, J=7.9 Hz, 1H), 7.57 (d, J=8.1 Hz, 1H), 7.67 (d, J=7.9 Hz, 1H), 7.7–7.8 (m, 3H).

EXAMPLE 23

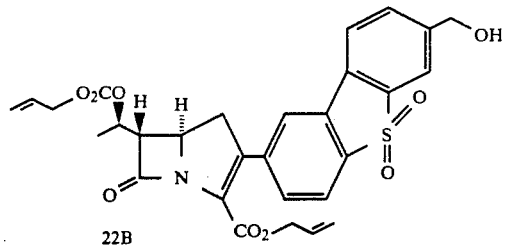

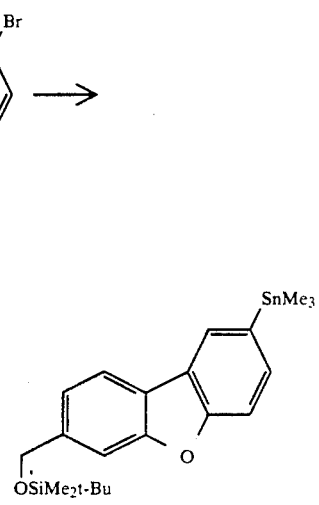

3-(Trimethylstannyl)-7-(t-butyldimethylsilyloxymethyl)dibenzofuran (23)

To a solution of the dibenzofuran 4 (995 mg, 2.5 mmol) in anhydrous THF (25 mL) at −78° C. under a nitrogen atmosphere was added a 1.5M t-butyllithium in pentane solution (3.0 mL, 5.25 mmol). The resulting yellow solution was stirred for 100 min., then trimethyltin chloride (548 mg, 2.75 mmol) was added as a solid. The mixture was allowed to warm to ambient temperature and then stirred for 3 hours. The reaction mixture was then poured into ether and the organic solution was washed with water (3 times) and then with brine. The organic solution was then dried with magnesium sulfate, filtered and concentrated under vacuum. Flash chromatography of the residue (silica gel, 10% methylene chloride in hexanes) provided 815 mg of the stannane 23 (68% yield) as a crystalline solid.

$^1$H-NMR (300 MHz, CDCl$_3$): δ0.22 (s, 6H), 0.35 (s, 9H), 0.95 (s, 9H), 4.88 (s, 2H), 7.24–7.28 (m, 1H), 7.52–7.59 (m, 2H), 7.89 (d, J=7.2 Hz, 1H), 8.02 ppm (s, 1H).

EXAMPLE 24

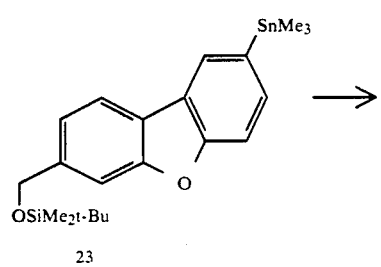

23

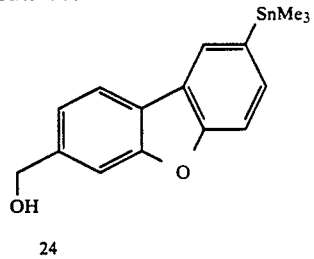

24

3-(Trimethylstannyl)-7-(hydroxymethyl)dibenzofuran (24)

To a solution of the dibenzofuran 23 (339 mg, 0.71 mmol) in anhydrous THF (7 mL) at 0° C. under a nitrogen atmosphere was added dropwise a 1M solution of tetrabutylammonium fluoride in THF (0.92 mL, 0.92 mmol). The reaction solution was stirred for 30 min., then saturated ammonium chloride was added. The mixture was then extracted with EtOAc and the organic solution was washed with brine. The organic solution was then dried with magnesium sulfate and then filtered and concentrated under vacuum. Flash chromatography of the residue (silica gel, 25% EtOAc in hexanes) provided 182 mg of 24 (70% yield) as a white solid.

$^1$H-NMR (300 MHz, CDCl$_3$): δ0.35 (s, 9H), 1.75 (apparent t, J=5.0 Hz, 1H), 4.85 (d, J=5.9 Hz, 2H), 7.34 (d, J=7.8 Hz, 1H), 7.52–7.60 (m, 3H), 7.84 (d, J=7.8 Hz, 1H), 8.05 ppm (s, 1H).

EXAMPLE 25

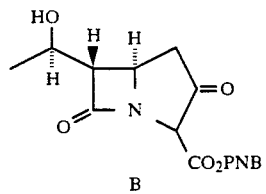

B i) TF$_2$O/DIPA
ii) TMSOTf/TEA iii) Pd$_2$(DBA)$_3$·CHCl$_3$/ZnCl$_2$
1-methyl-2-pyrrolidinone

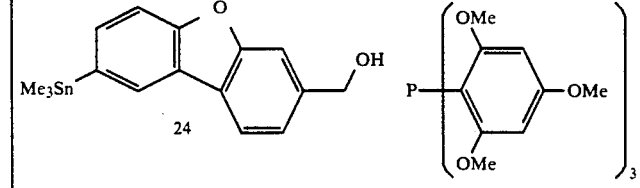

24

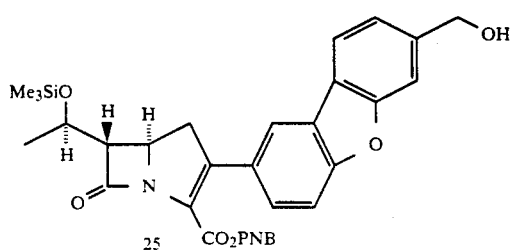

25 p-Nitrobenzyl-(5R,6S)-2-(2-hydroxymethyl-6-dibenzofuranyl)-6-[1R-(trimethylsilyloxy)ethyl]carbapen-2-em-3-carboxylate (25)

A dry 15 mL receiving flask was charged with the bicyclic β-ketoester B (143 mg; 0.41 mmol) and a magnetic stir bar and the system was purged with nitrogen. Anhydrous tetrahydrofuran (2 ml) was added and upon dissolution of B, the reaction vessel was cooled to −78° C. under $N_2$. Diisopropylamine (0.063 mL, 0.45 mmol) was then added and the stirring was continued for 10 minutes. Trifluoromethanesulfonic anhydride (0.075 mL, 0.45 mmol) was added, followed by stirring for an additional 15 min. Triethylamine (0.062 mL, 0.45 mmol) was then added, followed by trimethylsilyl trifluoromethanesulfonate (0.087 mL, 0.45 mmol).

While the above reaction was stirred for 20 min., the organostannane 24 (165 mg, 0.45 mmol), tris(dibenzylideneacetone)dipalladium-chloroform (8.5 mg, 0.0082 mmol) and tris(2,4,6-trimethoxyphenyl)phosphine (17.4 mg, 0.033 mmol) were weighed into a single vial and the vial was purged with nitrogen. When the above reaction time had elapsed, N-methylpyrrolidinone (2 mL) was added to the initial reaction mixture followed by the previously weighed solids. A 0.87M zinc chloride in ether solution (0.52 mL, 0.45 mmol) was then added. The low temperature bath was then removed and the reaction vessel was placed in a luke warm water bath to allow it to quickly reach ambient temperature. After reaching ambient temperature, the mixture was stirred for 20 minutes.

The reaction was then quenched by pouring the contents of the flask into a 125 mL separatory funnel containing diethyl ether, ethyl acetate and water. The organic phase was separated and washed with water and brine. The organic phase was dried over magnesium sulfate. The mixture was then filtered and the solvent removed under vacuum. Flash column chromatography of the residue (silica gel, 60–65% ethyl acetate/hexanes) provided 173 mg (70%) of carbapenem 25 as a slightly yellowish foam.

$^1$H-NMR (300 MHz, CDCl$_3$): δ0.15 (s, 9H), 1.30 (d, J=6.3 Hz, 3H), 1.97 (dd, J$_1$=J$_2$=3.0 Hz, 1H), 3.27 (dd, J=6.4, 2.9 Hz, 1H), 3.31 (complex m, 2H), 4.26 (complex m, 2H), 4.83 (d, J=5.6 Hz, 2H), 5.21 (AB$_q$, J$_{AB}$=13.6 Hz, Δν$_{AB}$=54.3 Hz, 2H), 7.28 (d, J=8.5 Hz, 3H), 7.40 (dd, J=8.6, 1.8 Hz, 1H), 7.49 (d, J=8.4 Hz, 1H), 7.56 (s, 1H), 7.69 (d, J=8.0 Hz, 1H), 7.82 (d, J=1.6 Hz, 1H), 7.91 ppm (d, J=8.7 Hz, 2H);

IR (CHCl$_3$): 3600, 1770, 1720, 1600, 1520 cm$^{-1}$;

U.V. (CH$_3$CN): λ$_{max}$ 290 nm (ε10,500), λ$_{max}$ 253 nm (ε11,300).

EXAMPLE 26

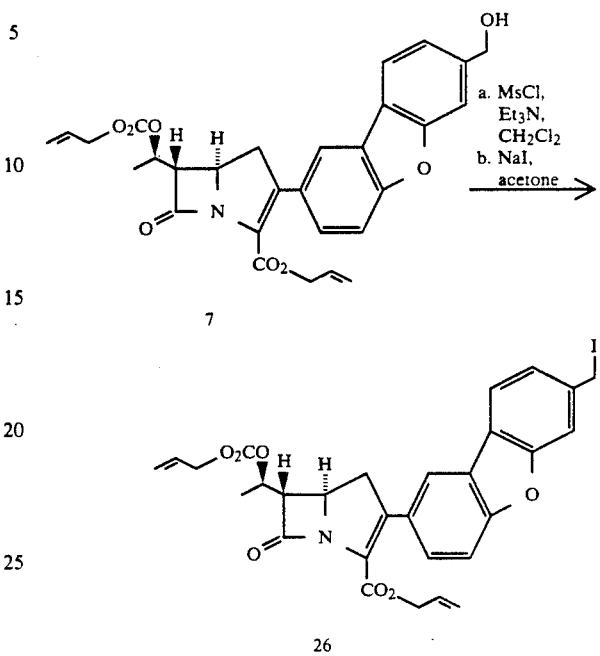

Allyl-(5R,6S)-2-(2-iodomethyl-6-dibenzofuranyl)-6-[1R-(allyloxycarbonyloxy)ethyl]-carbapen-2-em-3-carboxylate (26)

A solution of carbapenem 7 (135 mg, 0.26 mmol) in methylene chloride (3.6 ml) was cooled to −40° C.; triethylamine (0.082 ml, 0.41 mmol) and methanesulfonyl chloride (0.338 mmol, 0.037 ml) were added. The reaction was allowed to warm to −10° C. over 30 minutes, quenched with saturated NH$_4$Cl, diluted with ethyl acetate and washed successively with saturated NH$_4$Cl, NaHCO$_3$, H$_2$O, and brine. Drying (MgSO$_4$) and evaporation gave 133 mg of the mesylate as an oil which was used in the next step without purification.

The above mesylate was dissolved in acetone (3.6 ml) and cooled to 0° C. Sodium iodide (110 mg, 0.52 mmol) was added, and the reaction mixture was stirred at 0° C. in the dark for 15 minutes and then at room temperature for 1 hour. The mixture was diluted with ethyl acetate and was then washed successively with 5% Na$_2$S$_2$O$_3$, water, and brine. Drying (Na$_2$SO$_4$) and evaporation yielded 134 mg (81% overall) of a yellow oil which was used in the next reaction without purification.

$^1$H-NMR (300 MHz, CDCl$_3$): δ1.49 (d, J=6.35, 3H, CH$_3$); 3.29–3.34 (m, 2H, H1a,b); 3.43 (dd, J=8.57, 2.78, 1H, H6); 4.30 (dt, J=2.75, 9.85, 1H, H5); 4.59–4.70 (m, 4H, —OCH$_2$C=C); 4.61 (s, 2H, —CH$_2$—I); 5.12–5.39 (m, 5H, H8, —C=CH$_2$); 5.77–5.97 (m, 2H, —CH=C); 7.36 (d, J=9.4, 1H); 7.46–7.55 (m, 3H); 7.79 (d, J=7.88, 1H); 7.92 (s, 1H).

EXAMPLE 27

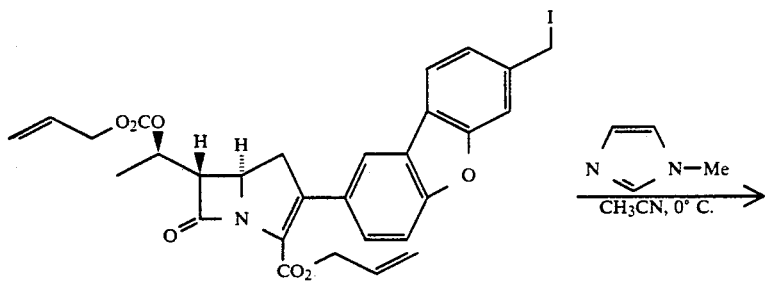

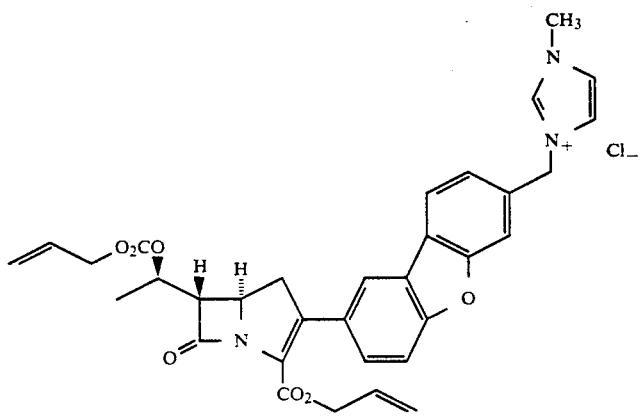

Allyl-(5R,6S)-2-[2-(3-methyl-1-imidazolium)methyl-6-dibenzofuranyl]-6-[1R-(allyloxycarbonyloxy)ethyl]carbapen-2-em-3-carboxylate chloride (27)

The iodide 26 prepared in the preceding example (50 mg, 0.079 mmol) was dissolved in acetonitrile (0.9 ml), cooled to 0° C., and 1-methylimidazole (0.094 ml, 0.12 mmol) was added. The ice bath was removed and the reaction was stirred for 19 hours at room temperature. The solution was diluted into methylene chloride and then washed successively with saturated NH₄Cl and brine. Drying (MgSO₄) and evaporation yielded 46 mg of a yellow solid which was dissolved in methylene chloride (0.6 ml) and added dropwise to ethyl ether (6 ml) forming a precipitate which was collected by centrifugation. After drying under vacuum 37 mg (75%) of the title compound was obtained.

$^1$H-NMR (300 MHz, CDCl₃): $\delta$1.48 (d, J=6.28, 3H); 3.29–3.37 (m, 2H, H1a,b); 3.46 (dd, J=8.21, 2.79, 1H, H6); 4.04 (s, 3H, N—CH₃); 4.30 (dt, J=2.76, 9.51, 1H, H5); 4.58–4.75 (m, 4H, —OCHC=C); 5.13–5.38 (m, 5H, H8, —C=CH₂); 5.73 (s, 2H, —CH₂—N); 5.78–5.99 (m, 2H, —CH=C), 7.20–7.35 (m, 2H); 7.45–7.55 (m, 3H), 7.69 (s, 1H); 7.90 (d, J=7.99, 1H); 7.95 (s, 1H), 10.0 (s, 1H).

EXAMPLE 28

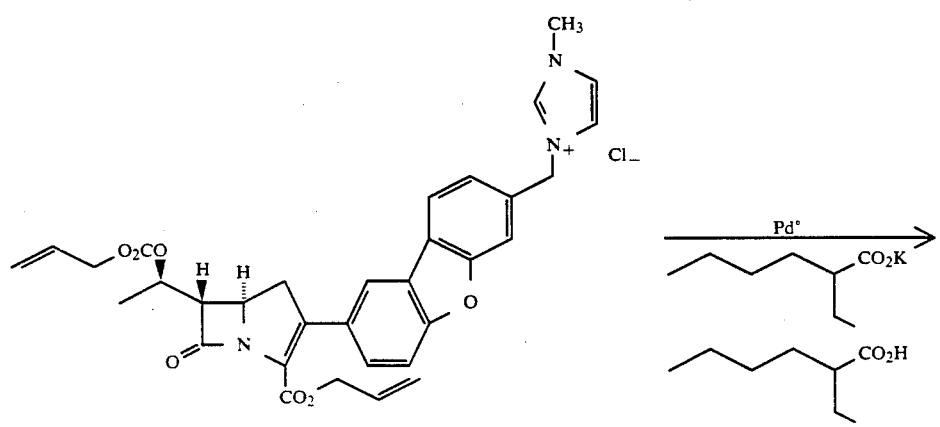

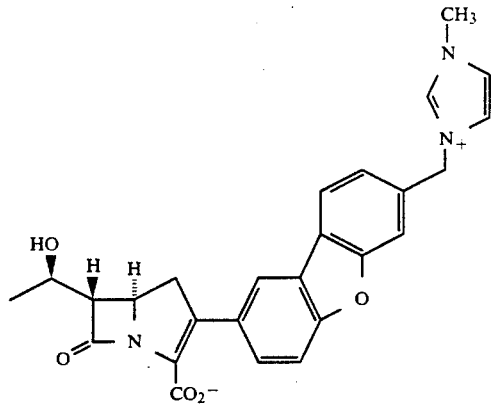

(5R,6S)-2-[2-(3-methyl-1-imidazolium)methyl-6-dibenzofuranyl]-6-(1R-hydroxyethyl)-carbapen-2-em-3-carboxylate (28)

To a solution of the carbapenem 27 (37 g, 0.059 mmol) in ethyl acetate (0.25 ml)-methylene chloride (0.75 ml) were added sequentially potassium 2-ethylhexanoate (0.50M in EtOAc, 0.118 ml, 0.059 mmol), 2-ethylhexanoic acid (1.0M in $CH_2Cl_2$, 0.059 ml, 0.059 mmol), triphenylphosphine (5 mg, 0.02 mmol), and tetrakis(triphenylphosphine)palladium (7 mg, 0.005 mmol). The reaction mixture was stirred at room temperature for 2 hours during which time a yellow precipitate formed. The mixture was added dropwise to 6 ml ice cold ethyl ether and the precipitate was collected by centrifugation, washing with ethyl ether. After drying, 35 mg of a tan solid was obtained which was purified by reverse phase prep tlc (2:1 water:acetonitrile) to yield 5.1 mg (18%) of the title compound as a lyophilized solid.

UV ($H_2O$): $\lambda$max=292 ($\epsilon$=25,000).

IR (KBr): 1750 ($\beta$-lactam), 1690 cm$^{-1}$ (carboxylate).

$^1$H-NMR (300 MHz, 2:1 $D_2O$:$CD_3CN$): $\delta$1.68 (d, J=6.41, 3H, —$CH_3$); 3.52 (dd, J=9.76, 7.14, 1H, H1a); 3.81-3.92 (m, 2H, H1b, H6); 4.23 (s, 3H, N—CH); 4.58-4.71 (m, 2H, H5, H8); 5.88 (s, 2H, —$CH_2$—N); 7.80-7.87 (m, 3H); 7.96 (s, 2H); 8.04 (s, 1H); 8.46 (s, 1H); 8.50 (d, J=7.94, 1H).

EXAMPLE 29

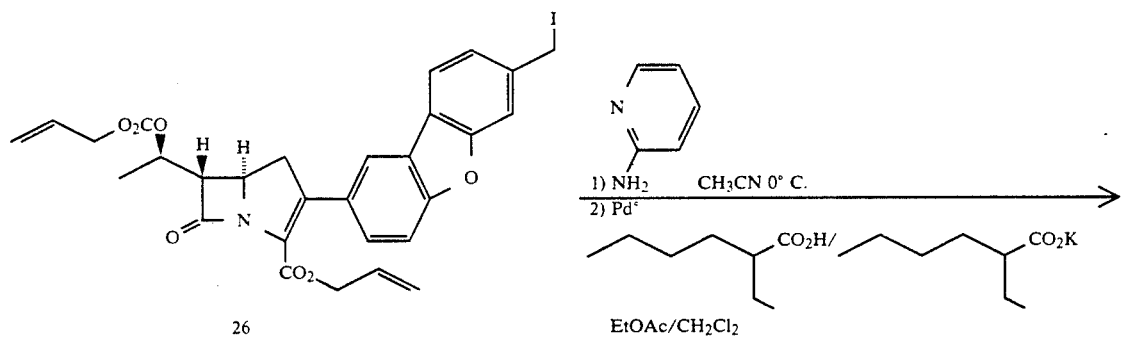

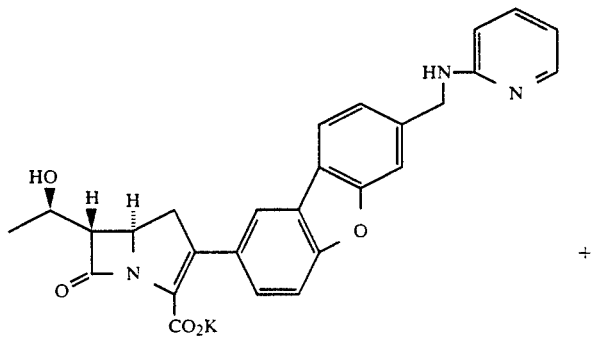

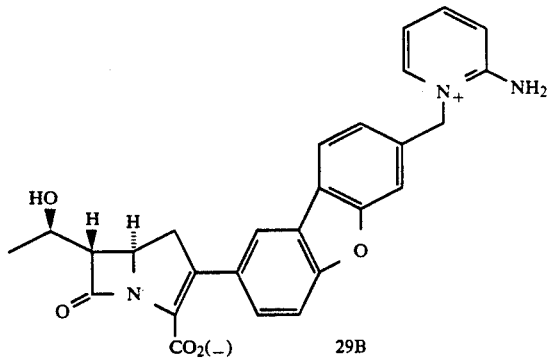

Potassium (5R,6S)-2-{2-[(2-pyridyl)amino]methyl-6-dibenzofuranyl}-6-(1R-hydroxyethyl)-carbapen-2-em-3-carboxylate (29A) and (5R,6S)-2-[2-(2-aminopyridinium)methyl-6-dibenzofuranyl]-6-(1R-hydroxyethyl)carbapen-2-em-3-carboxylate (29B)

To a solution of the iodide 26 (180 mg, 0.287 mmol) in acetonitrile (2 ml) at 0° C. was added 2-aminopyridine (1M in acetonitrile, 0.602 ml, 0.602 mmol), and silver trifluoromethane sulfonate (0.5M in acetonitrile, 0.631 ml, 0.315 mmol). The reaction was stirred in the dark for 6 hours and was then diluted into methylene chloride and washed successively with saturated NH$_4$Cl, saturated NaHCO$_3$, H$_2$O, and brine. Drying (MgSO$_4$) and evaporation yielded 98 mg of a yellow oil which was a mixture of internally and externally alkylated isomers.

IR (CHCl$_3$): 1780 ($\beta$-lactam), 1740 (carbonate), 1725 (ester), 1660 cm$^{-1}$ (iminium).

The above oil was dissolved in methylene chloride (2.2 ml)-ethyl acetate (0.75 ml) and potassium 2-ethylhexanoate (0.5M in ethyl acetate, 0.330 ml, 0.165 mmol), 2-ethylhexanoic acid (1M in methylene chloride, 0.165 ml, 0.165 mmol), tetrakis (triphenylphosphine)palladium (19.0 mg, 0.016 mmol), and triphenylphosphine (13 mg, 0.050 mmol) were added. The reaction mixture was stirred for 3 hours at room temperature during which time a yellow precipitate formed. The reaction was added dropwise to 4 ml of ice cold ethyl ether and the precipitate was collected by centrifugation and washed with ethyl ether to yield 81.1 mg of a pale yellow solid. This solid was purified by reverse phase prep-tlc (2:1 H$_2$O:CH$_3$CN) to yield 8.6 mg (10.2%) of the faster eluting externally alkylated product 29A and 7.9 mg (10.2%) of the more slowly eluted internally alkylated product 29B as lyophilized solids.

29A:

UV (H$_2$O): $\lambda$max=291 ($\epsilon$=19,000).

IR (KBr): 1750 ($\beta$-lactam), 1600 cm$^{-1}$ (carboxylate).

$^1$H-NMR (300 MHz, 2:1 D$_2$O:CD$_3$CN): $\delta$1.62 (d, J=7.04, 3H, —CH$_3$); 3.41-3.49 (m, 1H, H1a); 3.76-3.86 (m, 2H, H1b, H6); 4.53-4.62 (m, 2H, H5, H8); 4.96 (s, 2H, —CH$_2$—N); 6.92-6.99 (m, 2H); 7.72-7.92 (m, 5H); 8.25-8.33 (m, 3H).

29B:

UV (H$_2$O): $\lambda$max=294 ($\epsilon$=25,000).

IR (KBr): 1750 ($\beta$-lactam), 1670 (iminium), 1580 cm$^{-1}$, (carboxylate).

$^1$H-NMR (300 MHz, 2:1 D$_2$O:CD$_3$CN): $\delta$1.66 (d, J=7.17, 3H, —CH$_3$); 3.48-3.54 (m, 1H, H1a); 3.81-3.90 (m, 2H, H1, H6); 4.57-4.70 (m, 2H, H5, H8); 5.90 (s, 2H, —CH$_2$—N); 7.36 (t, 1H); 7.50 (d, J=8.91, 1H); 7.65 (d, J=7.69, 1H); 7.82 (s, 1H); 7.94 (s, 2H); 8.29-8.31 (m, 2H); 8.41-8.48 (m, 2H).

EXAMPLE 30

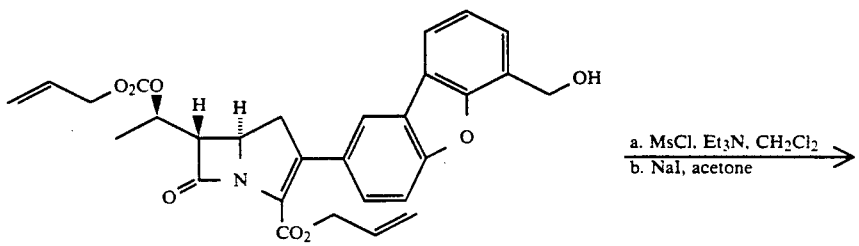

9

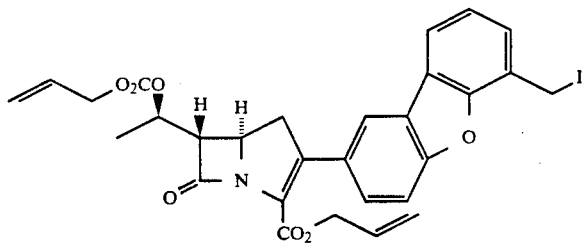

30

Allyl-(5R,6S)-2-(1-iodomethyl-6-dibenzofuranyl)-6-[1R-(allyloxycarbonyloxy)ethyl]carbapen-2-em-3-carboxylate (30)

In a manner analogous to that described in Example 26, but starting with the carbapenem 9 (188 mg, 0.363 mmol), the title compound (217 mg, 95%) was obtained as a yellow oil.

$^1$H-NMR (300 MHz, CDCl$_3$): δ1.49 (d, J=6.4 Hz, 3H, CH$_3$), 3.22-3.42 (m, 2H, H1), 3.44 (dd, J=2.8, 8.4 Hz, 1H, H6), 4.31 (ddd, J=2.8, 9.1, 9.6 Hz, 1H, H5), 4.56-4.66 (m, 4H, —OCH$_2$C=C), 4.75 (s, 2H, —CH$_2$I), 5.1-5.4 (m, 5H, H8, —C=CH$_2$), 5.75-6.00 (m, 2H, —CH=C), 7.27 (t, J=7.7 Hz, 1H), 7.4-7.5 (m, 2H), 7.59 (d, J=8.6 Hz, 1H), 7.81 (d, J=7.7 Hz, 1H), 7.94 (d, J=1.7 Hz, 1H).

EXAMPLE 31

Allyl-(5R,6S)-2-[1-(4-aminopyridinium)methyl-6-dibenzofuranyl]-6-[1R-(allyloxycarbonyloxy)ethyl]carbapen-2-em-3-carboxylate chloride (30)

A solution of the iodide 30 (65 mg, 0.10 mmol) in 1.5 ml of acetonitrile was cooled to 0° C. and a solution of 4-aminopyridine in acetonitrile (0.30M, 0.40 ml, 1.2 equiv.) was added dropwise. After stirring for 4 hours, the reaction mixture was diluted into methylene chloride and washed successively with sat. NH$_4$Cl and brine. Drying (MgSO$_4$) and evaporation gave 40.4 mg (63%) of the title compound.

$^1$H-NMR (300 MHz, CDCl$_3$): δ1.47 (d, J=6.4 Hz, 3H, CH$_3$), 3.2-3.6 (m, 3H, H1, H6), 4.32 (br t, J=9 Hz, 1H, 5H), 4.4-4.8 (m, 4H, —OCH$_2$C=C) 5.1-5.4 (m, 5H, 8H, —C=CH$_2$), 5.5 (bs, 2H, —CH$_2$N), 5.75-6.00 (m, 2H, —CH=C), 7.2-8.0 (m, 10H), 8.28 (bs, 2H).

EXAMPLE 32

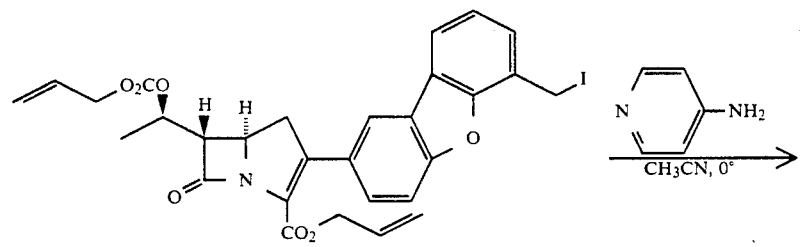

30

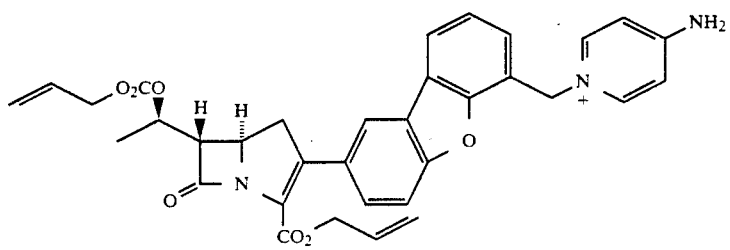

31

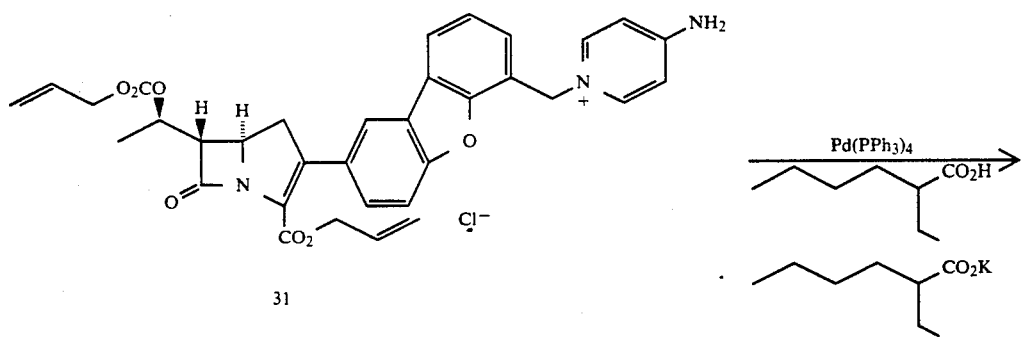

(5R,6S)-2-[1-(4-aminopyridinium)methyl-6-dibenzofuranyl]-6-(1R-hydroxyethyl)carbapen-2-em-3-carboxylate (32)

In an analogous manner to that described in Example 28, the carbapenem 31 (92 mg, 0.149 mmol) was deallylated to yield 11 mg (16%) of the title compound as a lyophilized solid.

$^1$H NMR (300 MHz, 2:1 D$_2$O/CD$_3$CN): δ1.70 (d, J=6.5 Hz, 3H, CH$_3$), 3.51 (dd, J=9.4, 17 Hz, 1H, H1a), 3.80-3.94 (m, 2H, H1b, H6), 4.56-4.76 (m, 2H, H5, H8), 5.98 (s, 2H, —CH$_2$N), 7.22 (d, J=6.3 Hz, 2H), 7.84 (t, J=7.6, 1H), 7.94 (d, J=7.6 Hz, 1H), 7.97 (bs, 2H), 8.42 (s, 1H), 8.50 (d, J=7.8 Hz, 1H), 8.57 (d, J=6.3 Hz, 2H).

IR (KBr): 1750 (β-lactam), 1655 (iminium), 1585 cm$^{-1}$ (carboxylate).

UV (H$_2$O): λmax=263 nm (ε=35,700).

EXAMPLE 33

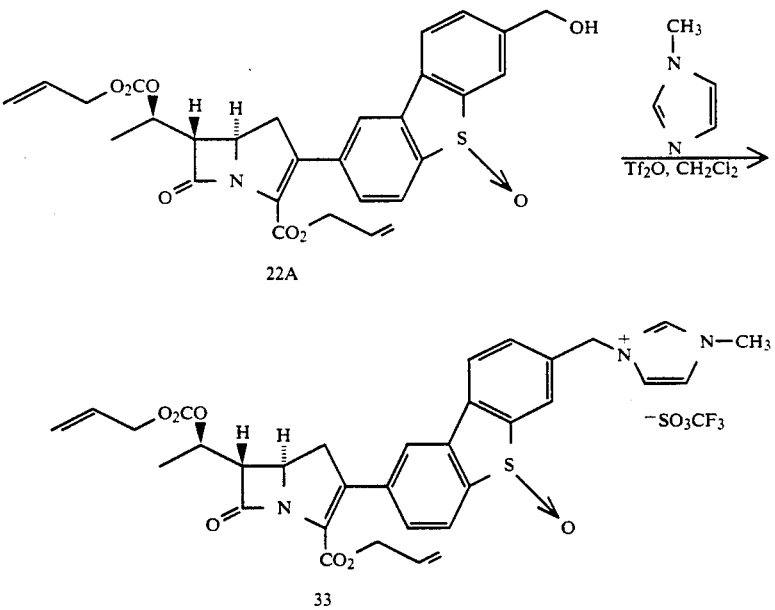

Allyl-(5R,6S)-2-[2-(3-methyl-1-imidazolium)methyl-9-oxo-6-dibenzothienyl]-6-[1R-(allyloxycarbonyloxy)ethyl]carbapen-2-em-3-carboxylate trifluoromethanesulfonate (33)

A solution of the carbapenem 22A (54.0 mg, 0.0983 mmol) and 1-methylimidazole (0.020 ml, 0.25 mmol) in 1 ml of CH$_2$Cl$_2$ was cooled to −70° C. and trifluoromethanesulfonic anhydride (0.020 ml, 0.12 mmol) was added. The yellow solution was allowed to warm to −20° C. during 1 hour and was then diluted with CH₂Cl₂ and washed with water. Drying (Na₂SO₄) and evaporation left 77.5 mg of a yellow oil.

¹H-NMR (300 MHz, CDCl₃): δ1.45 (d, J=6.5 Hz, 3H, CH₃), 3.14–3.52 (m, 2H, H1), 3.5–3.6 (m, 1H, H6), 3.86 (s, 3H, —NCH₃), 4.33, (br t, J=9 Hz, 1H, H5), 4.50–4.75 (m, 4H, —OCH₂C=C), 5.1–5.5 (m, 5H, H8, —C=CH₂) 5.43 (s, 2H, ArCH₂N), 5.75–6.00 (m, 2H, —CH=C), 7.24 (bs, 1H), 7.36 (bs, 1H), 7.4–7.5 (m, 1H), 7.6–7.7 (m, 1H), 7.77 (d, J=8 Hz, 1H), 7.81 (s, 1H), 7.8–7.9 (m, 1H), 7.92 (s, 1H), 9.18 (s, 1H).

EXAMPLE 34

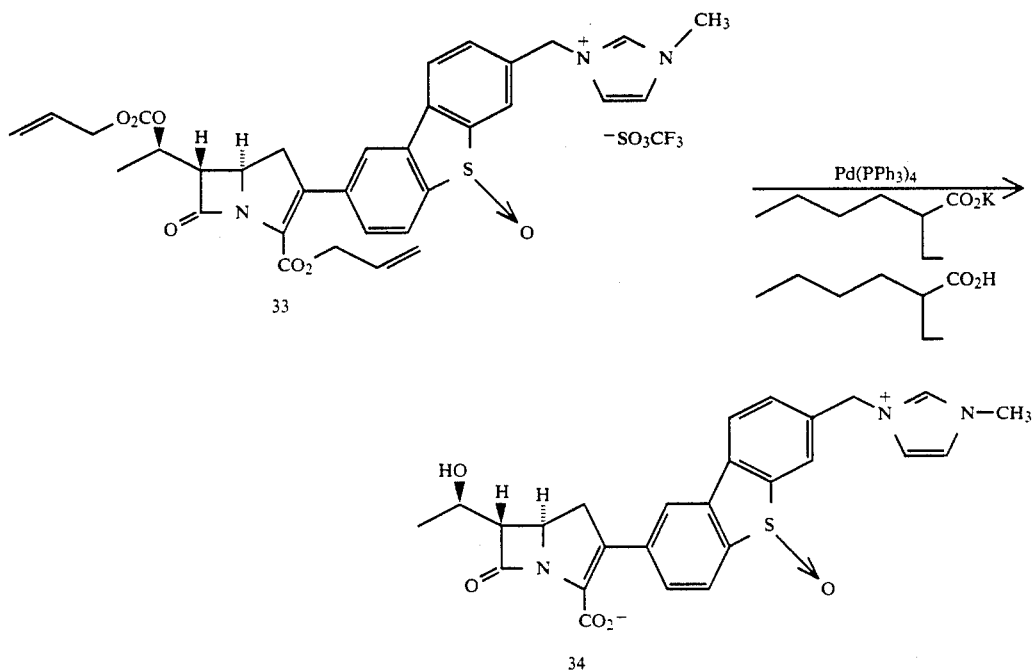

(5R,6S)-2-[2-(3-methyl-1-imidazolium)methyl-9-oxo-6-dibenzothienyl]-6-(1R-hydroxyethyl)-carbapen-2-em-3-carboxylate (34)

In an analogous manner to that described in Example 28, the carbapenem 33 (77.5 mg) prepared in the previous Example was de-allylated to yield 11.4 mg (24%) of the title compound as a yellow lyophilized solid.

¹H-NMR (300 MHz, 2:1 D₂O/CD₃CN): δ1.70 (d, J=6.4 Hz, 3H, CH₃), 3.5 (dd, J=10, 18 Hz, 1H, H1a), 3.84–3.96 (m, 2H, H1b, H6), 4.28 (s, 3H, —NCH₃), 4.58–4.68 (m, 1H, H8), 4.7 (br t, J=9 Hz, 1H, H5), 5.91 (s, 2H, —CH₂—N), 7.88 (s, 1H), 7.93 (s, 1H), 7.98 (d, J=8.7 Hz, 1H), 8.13 (d, J=8.6 Hz, 1H), 8.35–8.50 (m, 4H), 9.22 (s, 1H).

IR (KBr): 1750 (β-lactam), 1590 cm⁻¹ (carboxylate). UV (H₂O): 295 nm (ε=12,800), 251 (ε=24,000).

EXAMPLE 35

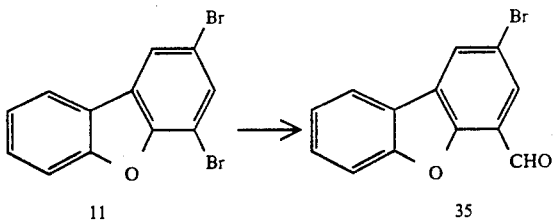

1-Formyl-3-bromodibenzofuran (35)

To a stirred solution of the 1,3-dibromobenzofuran 11 (10 g, 30.9 mmol) in anhydrous THF (250 mL) at −78° C. under nitrogen was added a 2.5M butyllithium in hexane solution (13.6 mL, 33.9 mmol). The resulting red solution was warmed to −50° C. and held there for 10 min. before anhydrous DMF (2.6 mL, 33.9 mmol) was added dropwise. The resulting rust colored solution was stirred an additional 20 min. at −50° to −40° C. before being quenched with saturated ammonium chloride solution (25 mL). The THF was removed under vacuum and the residue was dissolved in ethyl acetate (EtOAc) and washed sequentially with water, saturated aqueous ammonium chloride solution, water and brine. The organic solution was then dried with magnesium sulfate and decolorized with Norite. The mixture was then filtered and concentrated under vacuum. The residue was triturated with ether/hexane to provide 4.0 g of pale yellow flakes of dibenzofuran 35. The mother liquor was then chromatographed (silica gel, 30% EtOAc in hexanes) to provide an additional 2.1 g of dibenzofuran 35 (total yield: 73%).

¹H-NMR (300 MHz, CDCl₃): δ7.42 (t, J=7.5 Hz, 1H), 7.55 (t, J=7.3 Hz, 1H), 7.65 (d, J=7.9 Hz, 1H), 7.92 (d, J=7.7 Hz, 1H), 8.02 (d, J=1.6 Hz, 1H), 8.25 (d, J=1.9 Hz, 1H), 10.51 ppm (s, 1H).

EXAMPLE 36

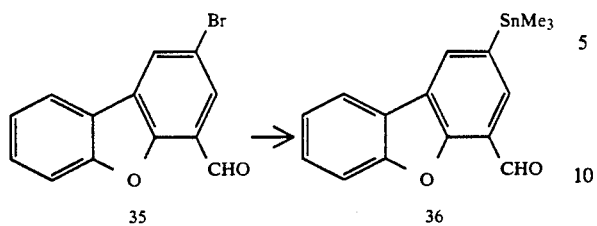

1-Formyl-3-(trimethylstannyl)dibenzofuran (36)

To a stirred solution of the dibenzofuran 35 (5 g, 18.2 mmol) in toluene (91 mL) was added hexamethylditin (3.9 mL, 20 mmol), tetrakis(triphenylphosphine)palladium (0) (1.05 g, 5 mol %) and triphenylphosphine (0.276 g, 5 mol %). Nitrogen was bubbled through the solution for 5 min., and the reaction solution was heated at reflux for 15 min. under a nitrogen atmosphere. The reaction mixture was then poured into ether and the organic solution was washed with water (3 times) and then brine (2 times). The solution was dried with magnesium sulfate, filtered and concentrated under vacuum. The residue was purified by flash chromatography (silica gel, 5% EtOAc in $CH_2Cl_2$) and crystallized to provide 4.3 g (66% yield) of stannane 36 as a white solid.

$^1$H-NMR (300 MHz, $CDCl_3$): δ0.40 (s, 9H), 7.40 (t, J=6.3 Hz, 1H), 7.52 (t, J=6.3 Hz, 1H), 7.68 (d, J=6.1 Hz, 1H), 8.00 (m, 2H), 8.19 (s, 1H), 10.62 ppm (s, 1H).

EXAMPLE 37

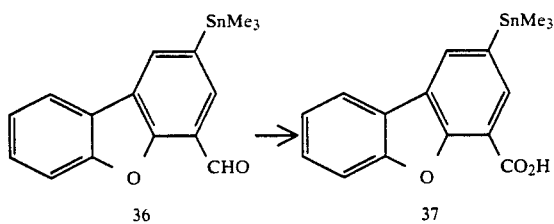

1-Carboxy-3-(trimethylstannyl)dibenzofuran (37)

A solution of tetra-n-butylammonium permanganate (5.1 g, 14.0 mmol) in anhydrous pyridine (35 mL) was transferred via cannula needle into a solution of the stannane 36 (5.0 g, 14.0 mmol) in anhydrous pyridine (35 mL) at 0° C. under a nitrogen atmosphere. The reaction was stirred for 30 min., then saturated aqueous sodium sulfate (50 mL) was added to quench the reaction. The mixture was then poured into ether and the layers separated. The organic layer was washed with 2N aqueous HCl (6 times with 100 mL), water (2 times) and then brine (2 times). The solution was dried with magnesium sulfate, then filtered and concentrated under vacuum to provide 4.8 g (92% yield) of the stannane 37 as a white solid.

$^1$H-NMR (300 MHz, $CDCl_3$): δ0.40 (s, 9H), 7.39 (t, J=8.4 Hz, 1H), 7.52 (t, J=8.4 Hz, 1H), 7.71 (d, J=8.4 Hz, 1H), 8.00 (d, J=7.8 Hz, 1H), 8.27 (s, 1H), 8.29 ppm (s, 1H).

EXAMPLE 38

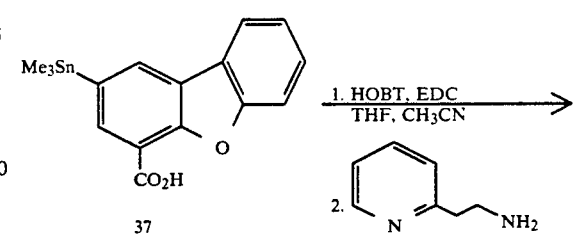

1-[N-2-(2-pyridyl)ethyl]carbamoyl-3-trimethylstannyl-dibenzofuran (38)

To a stirred solution of stannyl acid 37 (300 mg, 0.80 mmol) in dry THF (4.5 ml) under $N_2$ was added 1-(3-dimethylaminopropyl)-3-ethylcarbodiimide hydrochloride (183 mg, 0.96 mmol, 1.2 eq.) and 1-hydroxybenzotriazole hydrate (161 mg, 1.2 mmol, 1.5 eq.). Anhydrous $CH_3CN$ was added to solubilize the resulting suspension and the mixture was stirred for 30 minutes. 2-(2-aminoethyl)pyridine (0.14 ml, 1.2 mmol, 1.5 eq.) was then added. After 30 minutes had elapsed, the reaction mixture was poured into ether and washed with $H_2O$ (2×25 ml) and brine (2×25 ml), then dried ($MgSO_4$), filtered, and concentrated in vacuo. Purification by silica gel flash column chromatography (70% EtOAc/Hex) provided 375 mg (98%) of 38, as a colorless syrup.

$^1$H-NMR (300 MHz, $CDCl_3$): δ0.36 (s, 9H), 3.21 (t, J=6.6 Hz, 2H,) 4.05 (dd, J=6.4 Hz, J=12.6 Hz, 2H) 7.16–7.20 (m, 1H), 7.23 (d, J=7.8 Hz, 1H), 7.35–7.39 (m, 1H), 7.40–7.51 (m, 2H), 7.59–7.65 (m, 1H), 7.97 (d, J=7.6 Hz, 1H), 8.14 (s, 1H), 8.26 (s, 1H), 8.33 (s, 1H), 8.64 (d, J=3.8 Hz, 1H).

IR ($CHCl_3$): 3438, 3065, 3000, 1660 cm$^{-1}$.

EXAMPLE 39

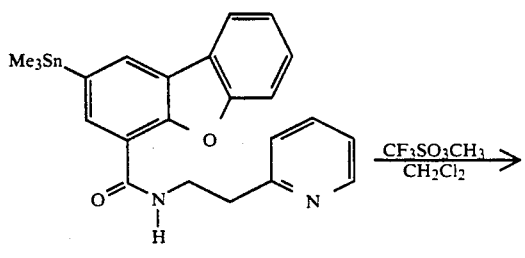

-continued

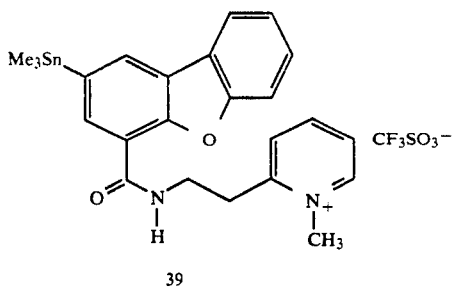

1-[N-2-(N-methyl-2-pyridinium)ethyl]carbamoyl-3-trimethylstannyl-dibenzofuran trifluoromethanesulfonate (39)

To a stirred solution of 38 (365 mg, 0.76 mmol) in anhydrous CH$_2$Cl$_2$ (3.8 ml) cooled to 0° C. under N$_2$ was added methyl trifluoromethanesulfonate (0.094 ml, 0.83 mmol, 1.1 eq.). The reaction mixture was stirred for 30 minutes at room temperature, then evaporated to provide 412 mg (96%) of 39.

$^1$H-NMR (300 MHz, CDCl$_3$): δ0.34 (s, 9H), 3.51 (t, J=6.6 Hz, 2H), 3.92-3.99 (m, 2H), 4.44 (s, 3H), 7.27 (t, J=7.3 Hz, 1H), 7.39 (t, J=7.3 Hz, 1H), 7.66-7.72 (m, 2H), 7.87-7.91 (m, 2H), 8.09-8.14 (m, 3H), 8.30 (apparent t, J=5.6 Hz, 1H), 8.72 (d, J=6.5 Hz, 1H).

IR: (CHCl$_3$) 3430, 3060, 3000, 1652 cm$^{-1}$.

EXAMPLE 40 p-Nitrobenzyl-(5R,6S)-2-{1-[N-2-(N-methyl-2-pyridinium)ethyl]carbamoyl-3-dibenzofuranyl}-6-[1R-(trimethylsilyloxy)ethyl]-carbapen-2-em-3-carboxylate trifluoromethanesulfonate (40)

To a stirred solution of the bicyclic β-keto ester B (75 mg, 0.12 mmol) in dry THF (0.65 ml) was added diisopropylamine (0.019 ml, 0.14 mmol, 1.1 eq.) at −78° C. under N$_2$, and the resultant yellow solution was stirred for 10 minutes. Trifluoromethanesulfonic anhydride (0.023 ml, 0.14 mmol, 1.1 eq.) was added to the reaction mixture, which was then stirred for 15 minutes. Triethylamine (0.019 ml, 0.14 mmol, 1.1 eq.) was added, followed by trimethylsilyltrifluoromethanesulfonate (0.027 ml, 0.14 mmol, 1.1 eq.) and the solution was stirred for 20 minutes.

Anhydrous N-methyl-2-pyrrolidinone (0.65 ml) was added next, followed by addition of bis(acetonitrile)palladium(II) chloride (16 mg, 6.3×10$^{-3}$ mmol, 5 mol %) and aryl stannane 39 (75 mg, 0.12 mmol, 0.91 eq.). Finally, a 0.87M solution of ZnCl$_2$ in ethyl ether (0.16 ml, 0.14 mmol, 1.1 eq) was added. The low temperature bath was removed, and the reaction vessel was placed in a warm water bath to quickly reach ambient temperature. The black mixture was then stirred for 20 minutes.

The reaction was quenched by pouring the mixture into a separatory funnel containing EtOAc (25 ml), Et$_2$O (10 ml), and H$_2$O (10 ml). The organic phase was then washed with H$_2$O (3×10 ml), dried (MgSO$_4$), decolorized briefly with Norite, filtered, and concentrated in vacuo. Purification by silica gel flash column chromatography (8% MeOH/CH$_2$Cl$_2$) provided 36 mg (35%) of 40.

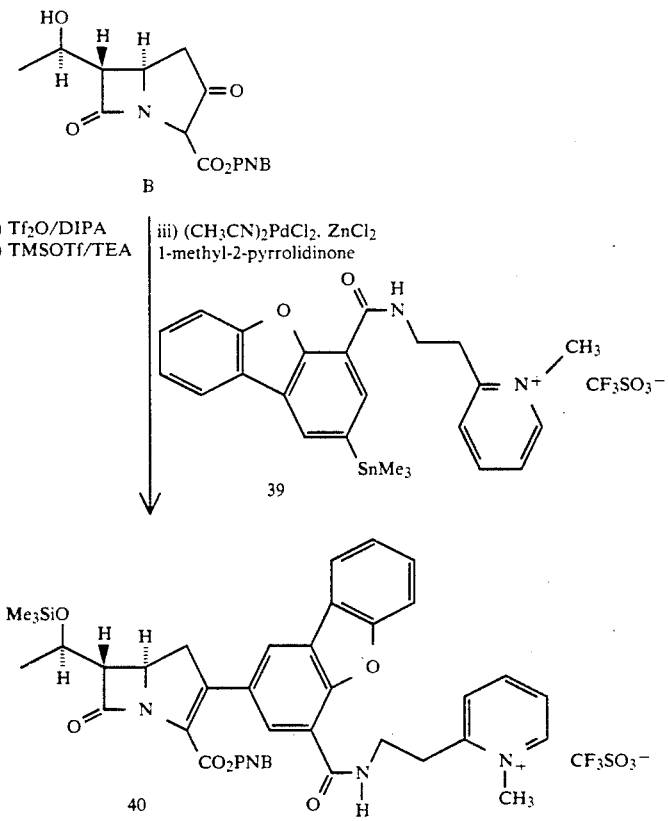

1H-NMR (300 MHz, CDCl3): δ0.12 (s, 9H), 1.26 (d, J=6.2 Hz, 3H), 3.27-3.46 (m, 3H), 3.49-3.62 (m, 2H), 3.96-3.99 (m, 2H), 4.24-4.49 (m, 2H), 4.51 (s, 3H), 5.25 (ABq, J=13.9 Hz, ΔνAB=48.3 Hz, 2H), 7.34 (t, J=7.1 Hz, 1H), 7.43-7.51 (m, 3H), 7.73-7.81 (m, 3H), 7.94 (d, J=7.6 Hz, 1H), 8.00-8.06 (m, 4H), 8.19-8.25 (m, 1H), 8.31-8.35 (m, 1H), 8.64 (d, J=5.6 Hz, 1H),

IR (CHCl3): 3420, 3000, 2960, 1775, 1725, 1660 cm$^{-1}$.

UV (CH3CN): $\lambda_1$=319 nm ($\epsilon_1$=10,000), $\lambda_2$=290 nm ($\epsilon_2$=17,000), $\lambda_3$=259 nm ($\epsilon_3$=24,000).

EXAMPLE 41

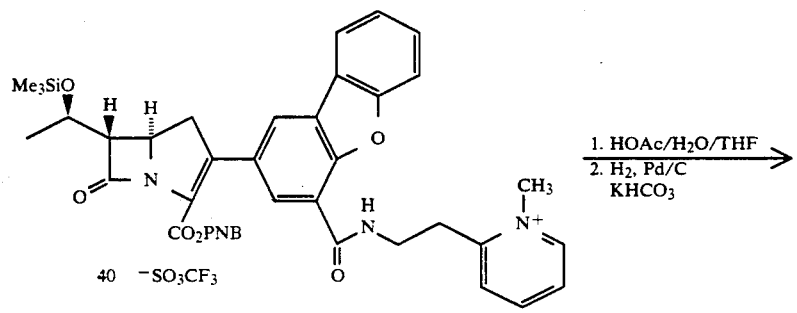

(5R,6S)-2-{1-[N-2-(N-methyl-2-pyridinium)ethyl]carbamoyl-3-dibenzofuranyl}-6-(1R-hydroxyethyl)carbapen-2-em-3-carboxylate (41)

A solution of 40 (33 mg, 3.8×10$^{-2}$ mmol) in 1.3:1.3:2 v/v THF/EtOH/H2O and acetic acid (1.0 μl, 0.19 mmol, 0.3 eq.) was stirred for 2 hours at 35° C. Potassium bicarbonate (7.6 mg, 7.6×10$^{-2}$ mmol, 2.0 eq.) was added, followed by 10% Pd/C (3.3 mg, 10 wt %). The mixture was hydrogenated under a H2 balloon at room temperature for 1 hour then filtered through a pad of Celite using water as the eluant. The THF and EtOH were removed from the filtrate in vacuo, and the remaining water was frozen and lyophilized at 0° C. The crude product was re-dissolved in 4:1 H2O/CH3CN and purified by reverse-phase prep plate chromatography eluting with 1:1 H2O/CH3CN to provide 6.5 mg (33%) of a light yellow solid.

1H-NMR (300 MHz, 2:1 D2O/CD3CN): δ1.74 (d, J=6.4 Hz, 3H), 3.57 (dd, J=9 Hz, J=15 Hz, 1H), 3.89-3.97 (m, 4H), 4.42 (t, J=6.2 Hz, 2H), 4.65-4.75 (m, 2H), 4.83 (s, 3H), 7.93 (t, J=7.7 Hz, 1H), 8.03-8.14 (m, 3H), 8.28-8.35 (m, 2H), 8.40 (d, J=7.7 Hz, 1H), 8.56 (d, J=7.5 Hz, 1H), 8.65 (s, 1H), 8.80 (t, J=7.8 Hz, 1H) 9.18 (d, J=5.6 Hz, 1H).

IR (KBr): 3400, 3060, 2980, 1755, 1648, 1595 cm$^{-1}$.
UV (H2O): λ=298 nm, (ε=7600).

EXAMPLES 42-55

Operating as described in the previous examples, the compounds of Table III were analogously prepared.

TABLE III

| Example No. | $R^a$ or $R^b$ | M | $\lambda_{max(nm)}^{H2O}$ |
|---|---|---|---|
| 42 | 4-amino-1-ethylpyridinium | (−) | 273 |
| 43 | 2-amino-1-ethylpyridinium | (−) | 295 |
| 44 | 2-(N-ethylamino)pyridine | K | 294 |
| 45 | 1-ethyl-3-methylimidazolium | (−) | 293 |

TABLE III-continued

| Example No. | X | M | $\lambda_{max(nm)}^{H_2O}$ |
|---|---|---|---|

(structure: pyrrolidinone-carbapenem with hydroxyethyl and dibenzofuran-$R^b$ substituent, $CO_2M$)

| 46 | 1-ethyl-2-aminopyridinium | (—) | 294 |
| 47 | 1-ethyl-3-methylimidazolium | (—) | 292 |

| Example No. | X | M | $\lambda_{max(nm)}^{H_2O}$ |
|---|---|---|---|

(structure: carbapenem with hydroxyethyl and dibenzofuran with $R^a$)

| 48 | 1-ethyl-4-aminopyridinium | (—) | 278 |
| 49 | 1-ethyl-3-methylimidazolium | (—) | 290 |
| 50 | 1-ethyl-2-aminopyridinium | (—) | 293 |
| 51 | 2-(ethylamino)pyridine | K | 293 |
| 52 | 2-(acetamidomethyl)-1-methylpyridinium | (—) | 293 |
| 53 | N-[2-(pyridin-2-yl)ethyl]acetamide | K | 294 |
| 54 | N-[2-(pyridin-2-yl N-oxide)ethyl]acetamide | K | 294 |

(structure: carbapenem with hydroxyethyl and biphenyl-thioether-$R^b$, $CO_2M$)

| 55 | 1-ethyl-3-methylimidazolium | (—) | 300 |

(structure: carbapenem with hydroxyethyl and dibenzofuran-$R^b$, $CO_2M$)

| 56 | 1-ethyl-3-(2-hydroxyethyl)imidazolium | (—) | 290 |

(structure: carbapenem with hydroxyethyl and biphenyl-sulfone-$R^b$, $CO_2M$)

| 57 | 1-ethyl-3-methylimidazolium | (—) | 288 |

(structure: carbapenem with hydroxyethyl and biphenyl-ether-$R^b$, $CO_2M$)

| 58 | 1-ethyl-3-methylimidazolium | (—) | 326 |
| 59 | 1-ethyl-4-aminopyridinium | (—) | 332 |

TABLE III-continued

| 60 | 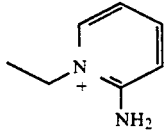 | (—) | 322 |
|---|---|---|---|

What is claimed:
1. A compound of the formula:

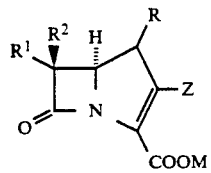   (I.)

where Z is;

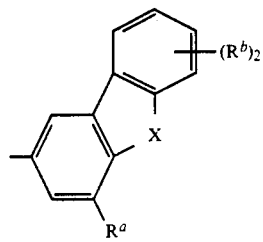   (A.)

or

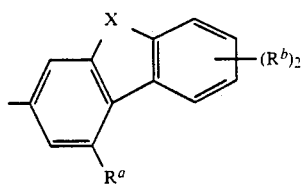   (B.)

wherein:
X is O or $S(O)_{0-2}$;
R is H or $CH_3$;
$R^1$ and $R^2$ are independently H, $CH_3$—, $CH_3CH_2$—, $(CH_3)_2CH$—, $HOCH_2$—, $CH_2CH(OH)$—, $(CH_3)_2C(OH)$—, $FCH_2CH(OH)$—, $F_2CHCH(OH)$—, $F_3CCH(OH)$—, $CH_3CH(F)$—, $CH_3CF_2$—, or $(CH_3)_2C(F)$—;
$R^a$ and $R^b$ are independently selected from the group consisting of hydrogen and the radicals set out below provided that one but not more than one of $R^a$ or $R^b$ is selected from Type I substituents and in total not more than three $R^a$ and $R^b$ radicals are other than hydrogen:

I.
b)

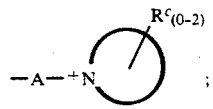

where
A is $(CH_2)_m$—Q—$(CH_2)_n$, where m is 0 to 6 and n is 1 to 6 and Q is a covalent bond, O, S, SO, $SO_2$, NH, —$SO_2NH$—, —$NHSO_2$—, —CONH—, —NH-CO—, —$SO_2N(C_1-C_4alkyl)$—, —$N(C_1-C_4alkyl)$-$SO_2$—, —$CON(C_1-C_4alkyl)$—, —$N(C_1-C_4alkyl)$-CO—, —CH=CH—, —CO—, —OC(O)—, —C(O)Q— or $N(C_1-C_4alkyl)$ and $(CH_2)_m$ is attached to the dibenzofuranyl or dibenzothienyl moiety;

is a 5- or 6-membered monocyclic heterocycle or an 8-, 9- or 10-membered bicyclic heterocycle, the heterocycle containing a first nitrogen in an aromatic 5- or 6-membered first ring, with attachment of the heterocycle to A by way of said first nitrogen and said first nitrogen is quaternary by virtue of the attachment in addition to the ring bonds thereto, with the first ring containing 0 or 1 of either O or S, with the first ring containing 0 to 3 additional nitrogen atoms, with the first ring optionally fused to a 3- or 4-membered moiety to form the optional second ring, with the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

$R^c$ is $R^a$ as defined under II below, hydrogen, or —$NR^yR^z$ (where $R^y$ and $R^z$ are defined in II below), but independently selected from $R^a$ and from each other if more than one $R^c$ is present, and is attached to a carbon ring atom or a nitrogen heteroatom the valency of which is not satisfied by the ring bonds;

b)

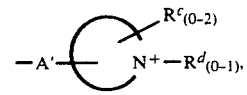

where

is a 5- or 6-membered monocyclic heterocycle or an 8-, 9- or 10-membered bicyclic heterocycle, the heterocycle containing a first nitrogen in an aromatic 5- or 6-membered first ring, with said first nitrogen either quaternary by virtue of a substituent $R^d$ in addition to the ring bonds thereto or neutral in the absence of a substituent $R^d$, with attachment of the heterocycle to A' by way of a carbon atom of a ring, with the first ring containing 0 or 1 of either O or S, with the first ring containing 0 to 2 additional nitrogen atoms, with the first ring optionally fused to a 3- or 4-membered moiety to form the optional second ring, with the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

$R^c$ is defined above;

$R^d$ is hydrogen, $NH_2$, $O^-$ or $C_1$-$C_4$alkyl (where the alkyl group is optionally mono-substituted with $R^q$ as defined under IIc below) with the proviso that $R^d$ is present and is not H when either 1) m and n in A' below are both zero and Q is $-OC=O$, S, SO, $SO_2$, $-NHSO_2$, $-N(C_1$-$C_4$ alkyl)$SO_2$, or $-CO$, or 2) m+n in A' below is equal to or less than 2 and Q is $CH=CH$ and

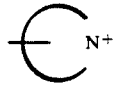

is pyridinium, quinolinium, or, isoquinolinium;

A' is $(CH_2)_m$—Q—$(CH_2)_n$, where m is 0 to 6 and n is 0 to 6, Q is as given above, except that when m and n are both 0 then Q is not a covalent bond, and $(CH_2)_m$ is attached to the dibenzofuranyl or dibenzothienyl moiety;

c) $-A_p-N^+R^y(R^w)_{(0-1)}(R^z)$ where $R^y$ and $R^z$ are as defined under II below, $R^y$ and $R^z$ may further be together a $C_2$-$C_4$ alkylidene radical to form a ring (optionally mono-substituted with $R^q$ as defined below) interrupted by $N(O)R^e$ or $N^+(R^e)_2$ (where $R^e$ is hydrogen, $C_1$-$C_4$ alkyl, or $C_1$-$C_4$ alkyl mono-substituted with $R^q$ as defined below), $R^w$ is hydrogen, $C_{1-4}$ alkyl, $O^-$, $NH_2$, or absent in which case the nitrogen is neutral, $R^w$, $R^y$ and $R^z$ may further together form a $C_5$-$C_{10}$ tertiary alkylidene radical which with $N^+$ forms a bicyclic ring, where the tertiary alkylidene radical is optionally mono-substituted with $R^q$ as defined below and where the tertiary carbon of the tertiary alkylidene radical is optionally replaced with nitrogen, $N^+R^e$ (where $R^e$ is defined above), or $N^+-O^-$, p is 0 or 1, and A is as defined above;

d)

where

is a 5- or 6-membered monocyclic heterocycle or an 8-, 9- or 10-membered bicyclic heterocycle, the heterocycle containing a first nitrogen in a first ring, with the first ring saturated or unsaturated and non-aromatic, with the first nitrogen either quaternary by virtue of one or two substituents $R^d$ in addition to the ring bonds thereto or neutral by virtue of 0 or 1 substituent $R^d$ in addition to the ring bonds thereto, with attachment of the heterocycle to A' by way of a carbon atom or non-quaternary nitrogen atom of a ring, with the first ring containing in addition to carbon and the first nitrogen 0 to 1 of a member selected from the group consisting of the non-quaternary nitrogen of attachment, O, S, S(O), $S(O)_2$ and $NR^e$ where $R^e$ is defined above, with the first ring optionally fused to a 2-, 3- or 4-membered moiety to form the optional second ring, with the moiety optionally containing in addition to carbon the non-quaternary nitrogen of attachment, and with the moiety saturated or unsaturated and the second ring non-aromatic;

$R^d$ is as defined above except without the proviso and where more than one $R^d$ is present on a nitrogen, at least one $R^d$ is hydrogen or $C_1$-$C_4$alkyl;

A' is defined above;

p is defined above; and $R^q$ is defined below;

II.

a) a trifluoromethyl group: $-CF_3$;

b) a halogen atom: $-Br$, $-Cl$, $-F$, or $-I$;

c) $C_1$-$C_4$ alkoxy radical: $-OC_{1-4}$alkyl, wherein the alkyl is optionally mono-substituted by $R^q$, where $R^q$ is a member selected from the group consisting of $-OH$, $-OCH_3$, $-CN$, $-C(O)NH_2$, $-OC(O)NH_2$, $CHO$, $-OC(O)N(CH_3)_2$, $-SO_2NH_2$, $-SO_2N(CH_3)_2$, $-SOCH_3$, $-SO_2CH_3$, $-F$, $-CF_3$, $-COOM^a$ (where $M^a$ is hydrogen, alkali metal, methyl or phenyl), tetrazolyl (where the point of attachment is the carbon atom of the tetrazole ring and one of the nitrogen atoms is monosubstituted by $M^a$ as defined above), and $-SO_3M^b$ (where $M^b$ is hydrogen or an alkali metal);

d) a hydroxy group: $-OH$;

e) a carbonyloxy radical: $-OC(O)R^s$, where $R^s$ is $C_{1-4}$ alkyl, phenyl, or heteroaryl, each of which is optionally mono-substituted by $R^q$ as defined above, and where heteroaryl is a monocyclic aromatic hydrocarbon group having 5 or 6 ring atoms, in which a carbon is the point of attachment, one of the carbon atoms has been replaced by a nitrogen atom, one additional carbon atom is optionally replaced by a heteroatom selected from O and S, and from 1 to 3 additional carbon atoms are optionally replaced by a nitrogen heteroatom;

f) a carbamoyloxy radical: $-O(O)CN(R^y)R^z$, where $R^y$ and $R^z$ are independently H, $C_{1-4}$ alkyl, together a 3- or 5-membered alkylidene radical to form a ring, or together a 2- to 4-membered alkylidene radical, interrupted by $-O-$, $-S-$, $-S(O)-$ or $-S(O)_2-$, to form a ring, and where $R^y$ or $R^z$ or both are defined as alkyl, including where joined together to form a ring, the alkyl is optionally monosubstituted by $R^q$, as defined above;

g) a sulfur radical: $-S(O)_n-R^s$ where n=0-2, and $R^s$ is as defined above;

h) a sulfamoyl group: $-SO_2N(R^y)R^z$ where $R^y$ and $R^z$ are as defined above;

i) azido: $N_3$ j) a formylamino group: $-N(R^f)-C(O)H$, where $R^f$ is H or $C_{1-4}$ alkyl, and the alkyl thereof is optionally mono-substituted by $R^q$ as defined above;

k) $(C_1$-$C_4$ alkyl)carbonylamino radical: $-N(R^f)-C(O)C_{1-4}$ alkyl, where $R^f$ is as defined above, and the alkyl group is also optionally mono-substituted by $R^q$ as defined above;

l) a ($C_1$-$C_4$ alkoxy) carbonylamino radical: —N(R'^)—C(O)O$C_{1-4}$ alkyl, where R' is as defined above, and the alkyl group is also optionally mono-substituted by $R^q$ as defined above;

m) a ureido group: —N(R$^t$)—C(O)N(R$^y$)R$^z$ where R$^t$, R$^y$ and R$^z$ are as defined above;

n) a sulfonamido group: —N(R$^t$)SO$_2$R$^s$, where R$^s$ and R$^t$ are as defined above;

o) a cyano group: —CN;

p) a formyl or acetalized formyl radical: —C(O)H or —C(OCH$_3$)$_2$;

q) ($C_1$-$C_4$ alkyl)carbonyl radical wherein the carbonyl is acetalized: —C(OCH$_3$)$_2$$C_{1-4}$ alkyl, where the alkyl is optionally mono-substituted by $R^q$ as defined above;

r) carbonyl radical: —C(O)—R$^s$, where R$^s$ is as defined above;

s) a hydroximinomethyl radical in which the oxygen or carbon atom is optionally substituted by a $C_1$-$C_4$ alkyl group: —(C=NOR$^z$)R$^y$ where R$^z$ are as defined above, except they may not be joined together to form a ring;

t) a ($C_1$-$C_4$ alkoxy)carbonyl radical: —C(O)O$C_{1-4}$ alkyl, where the alkyl is optionally mono-substituted by $R^q$ as defined above;

u) a carbamoyl radical: —C(O)N(R$^y$)R$^z$ where R$^y$ and R$^z$ are as defined above;

v) an N-hydroxycarbamoyl or N($C_1$-$C_4$ alkoxy)-carbamoyl radical in which the nitrogen atom may be additionally substituted by a $C_1$-$C_4$ alkyl group: —C(O)—N(OR$^y$)R$^z$ where R$^y$ and R$^z$ are as defined above, except that they may not be joined together to form a ring;

w) a thiocarbamoyl group: —C(S)N(R$^y$)R$^z$ where R$^y$ and R$^z$ are as defined above;

x) carboxyl: —COOM$^b$, where M$^b$ is as defined above;

y) thiocyanate: —SCN;

z) trifluoromethylthio: —SCF$_3$;

aa) tetrazolyl, where the point of attachment is the carbon atom of the tetrazole ring and one of the nitrogen atoms is mono-substituted by hydrogen, an alkaly metal or a $C_1$-$C_4$ alkyl optionally substituted by $R^q$ as defined above;

ab) an anionic function selected from the group consisting of: phosphono [P=O(OM$^b$)$_2$]; alkylphosphono {P=O(OM$^b$)—[O($C_1$-$C_4$ alkyl)]}; alkylphosphinyl [P=O(OM$^b$)—($C_1$-$C_4$alkyl)]; phosphoramido [P=O(OM$^b$)N(R$^y$)R$^z$ and P=O-(OM$^b$)NHR$^s$]; sulfino (SO$_2$M$^b$); sulfo (SO$_3$M$^b$); acylsulfonamides selected from the structures CONM$^b$SO$_2$R$^s$, CONM$^b$SO$_2$N(R$^y$)R$^z$, SO$_2$NM$^b$CON(R$^y$)R$^z$; and SO$_2$NM$^b$CN, where R$^s$, M$^b$, R$^y$, and R$^z$ are as defined above;

ac) $C_5$-$C_7$ cycloalkyl group in which one of the carbon atoms in the ring is replaced by a heteroatom selected from O, S, NH or N($C_1$-$C_4$ alkyl) and in which one additional carbon atom may be replaced by NH or N($C_1$-$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) $C_2$-$C_4$ alkenyl radical, optionally mono-substituted by one of the substituents a) to ac) above, or pyridyl, phenyl, quinoline, or isoquinoline each of which is optionally substituted by $R^q$ as defined above;

ae) $C_2$-$C_4$ alkynyl radical, optionally mono-substituted by one of the substituents a) to ac) above;

af) $C_1$-$C_4$ alkyl radical;

ag) $C_1$-$C_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected form S and NRt (where Rt is as defined above) and one of the saturated carbon atoms of the oxazolidinone ring is optionally mono-substituted by one of the substitutents a) to ag) above;

M is selected from:
i) hydrogen;
ii) a pharmaceutically acceptable esterifying group or removable carboxyl protecting group;
iii) an alkali metal or other pharmaceutically acceptable cation; or
iv) a negative charge which is balanced by a positively charged group.

2. A compound of claim 1 wherein R$^2$ is H and R$^1$ is (R)—CH$_3$CH(OH)— or (R)—CH$_3$CH(F)—.

3. A compound of claim 2 wherein Z is in the (A.) configuration.

4. A compound of claim 1 wherein R$^2$ is H, R$^1$ is (R)—CH$_3$CH(OH)—, one of R$^a$ or R$^b$ is a Type I substituent and one or two R$^a$ and R$^b$ substituents are independently selected from the group consisting of: —CH$_3$, —CH$_2$CH$_3$, —(CH$_2$)$_3$CH$_3$, —OCH$_3$, —SCH$_3$, tetrazolyl, —COOH, —CH$_2$CONH$_2$, —CH$_2$CH$_2$SO$_3$H, —CONH$_2$, —SO$_2$NH$_2$, —SO$_3$H, —CON(CH$_3$)$_2$, —CN, —CH$_2$CN, —CH$_2$SCH$_3$, —CH$_2$SO$_3$H, —CH$_2$SOCH$_3$, —SO$_2$CH$_3$, —SOCH$_3$, —CH$_2$OCH$_3$, —N$_3$, —OCONH$_2$, —OH, —CHO, —CH$_2$P(O)(OCH$_3$)OH, —CF$_3$, —CH$_2$OC(O)NH$_2$, —CH$_2$SO$_2$NH$_2$, —SCH$_2$CH$_2$CN, Br, Cl, F, —SCF$_3$, —CH$_2$SCF$_3$, —SCH$_2$CF$_3$, —COCH$_3$, —CH=NOH, —CONHOH, —C(S)NH$_2$, —OCOCH$_3$, —NHCOCH$_3$, —NHCO$_2$CH$_3$, —NHCONH$_2$, —NHSO$_2$CH$_3$, —SCN, —CH=CHCHO, —SCH$_2$CH$_2$OH, —CH$_2$OH, —CH=NOCH$_2$CO$_2$H, —CO$_2$CH$_2$CH$_2$OH, and —SO$_2$NHCH$_2$CONH$_2$.

5. A compound of claim 2 wherein the Type I. a) substituents are selected from the group consisting of:

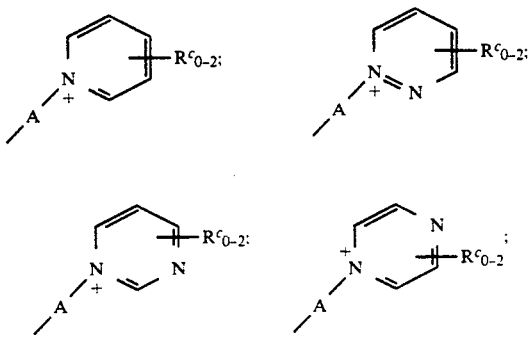

-continued
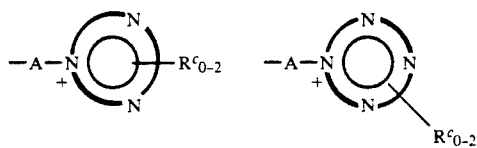
where the ring contains three carbon atoms;   where the ring contains two carbon atoms;
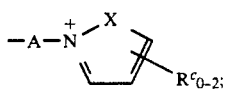
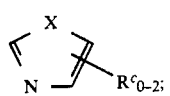
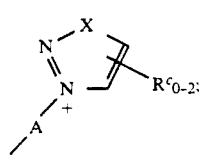
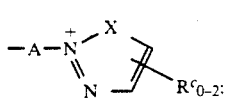
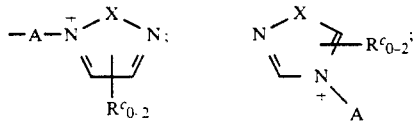
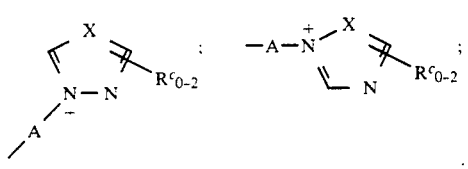
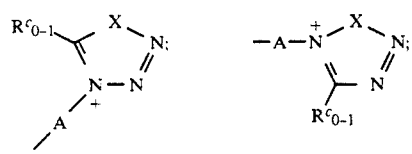
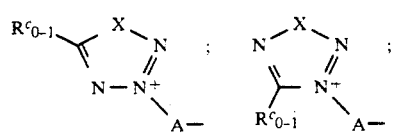
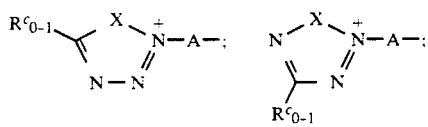
-continued
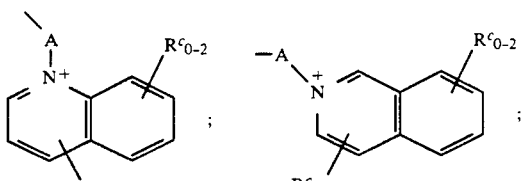
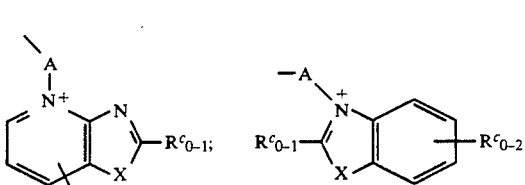
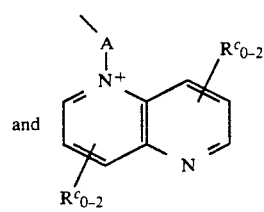
and
where X=O, S, or NR$^c$.
6. A compound of claim 2 wherein the Type I. b) substituents are selected from the group consisting of:
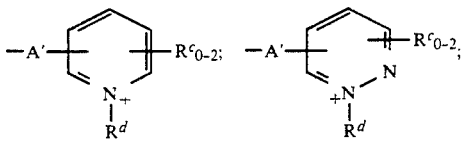
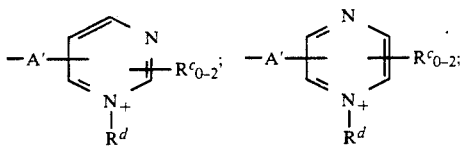
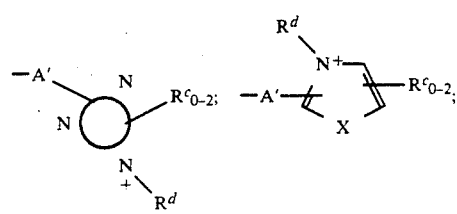
where the ring contains three carbon atoms
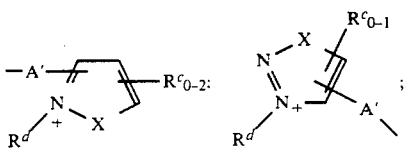

-continued

where X=O, S, or NR$^c$ and X'=O or S.

7. A compound of claim 2 wherein the Type I. c) substituents are selected from the group consisting of:

—A$_p$—$^+$N(CH$_3$)$_3$, —A$_p$—$^+$N(CH$_2$CH$_3$)$_3$,

-continued

—A$_p$—$^+$N(CH$_3$)$_2$CH$_2$R$^q$, —A$_p$—$^+$N(CH$_2$CH$_3$)$_2$CH$_2$CH$_2$R$^q$,

where W is O, S, NR$^e$, N(O)R$^e$, SO, SO$_2$ or N$^+$(R$^e$)$_2$ and W' is N$^+$R$^e$ or NO.

8. A compound of claim 2 wherein the Type I. d) substituents are selected from the group consisting of:

9. A compound of claim 2 wherein R$^c$, where attached to a ring carbon atom, is selected from the group consisting of —NH$_2$, —SCH$_3$, —SOCH$_3$, —CH$_2$OH, —(CH$_2$)$_2$OH, —OCH$_3$, —COOM$^b$, —CH$_2$COOM$^b$, —CH$_2$CH$_2$COOM$^b$, —CH$_2$SOCH$_3$, —CH$_2$SCH$_3$, —SO$_3$M$^b$, —CH$_2$SO$_3$M$^b$, —CH$_2$CH$_2$SO$_3$M$^b$, —Br, —Cl, —F, —I, —CH$_3$, CH$_2$CH$_3$, CH$_2$CONH$_2$ and CH$_2$CON(C$_1$-C$_4$alkyl) where M$^b$ is defined above.

10. A compound of claim 2 wherein R$^c$, where attached to a neutral ring nitrogen atom, is selected from the group consisting of —CH$_2$OH, —(CH$_2$)$_2$OH, —CH$_2$COOM$^b$, —CH$_2$CH$_2$COOM$^b$, —CH$_2$SOCH$_3$, —CH$_2$SCH$_3$, —CH$_2$SO$_3$M$^b$, —CH$_2$CH$_2$SO$_3$M$^b$, —CH$_3$, CH$_2$CH$_3$, CH$_2$CONH$_2$ and CH$_2$CON(C$_1$-C$_4$alkyl) where M$^b$ is defined above.

11. A compound of claim 2 wherein R$^d$ is selected from the group consisting of hydrogen, —CH$_3$, —CH₂CH₃, —CH₂CH₂CH₃, —CH₂COOM$^b$, —CH₂SO₃M$^b$, —NH₂ and O$^{(-)}$, where M$^b$ is defined above.

12. A compound of claim 2 wherein A is selected from the group consisting of —CH₂—, —CH₂CH₂—, —CH₂CH₂CH₂—, —CH₂CH₂CH₂CH₂—, —OCH₂CH₂—, —SOCH₂—, —SO₂CH₂—, —SCH₂CH₂—, —SOCH₂CH₂—, —SO₂CH₂CH₂—, —NHCH₂CH₂—, —N(CH₃)CH₂CH₂—, —CH₂N(CH₃)CH₂CH₂—, —CONHCH₂CH₂—, —SO₂NHCH₂CH₂—, —COCH₂—, —CH=CHCH₂— and —CH₂OCH₂CH₂—.

13. A compound of claim 2 wherein A' is selected from the group consisting of —CH₂—, —CH₂CH₂—, —CH₂CH₂CH₂—, —CH₂CH₂CH₂CH₂—, —OCH₂CH₂—, —SOCH₂—, —SO₂CH₂—, —SCH₂CH₂—, —SOCH₂CH₂—, —SO₂CH₂CH₂—, —NHCH₂CH₂—, —N(CH₃)CH₂CH₂—, —CH₂N(CH₃)CH₂CH₂—, —CONHCH₂CH₂—, —SO₂NHCH₂CH₂—, —COCH₂—, —CH=CHCH₂— and —CH₂OCH₂CH₂—, —O—, —S—, —NH—, —SO₂—, —SO₂NH—, —CONH—, —CH=CH—, —CH₂S—, —CH₂NH—, —CONHCH₂— and —SO₂NHCH₂—.

14. A compound

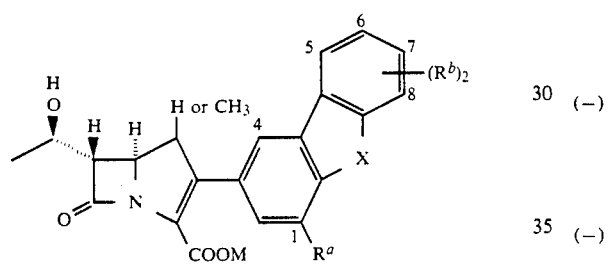

wherein two of R$^a$ or R$^b$ are H and the third is as shown:

| M | R$^a$ or R$^b$ | X |
|---|---|---|
| (−) | 1-CH₂N⁺—pyridine—NH₂ | O, SO |
| (−) | 5-CH₂N⁺—pyridine—NH₂ | O, SO |
| (−) | 6-CH₂N⁺—pyridine—NH₂ | O, SO |
| (−) | 7-CH₂N⁺—pyridine—NH₂ | O, SO |
| (−) | 8-CH₂N⁺—pyridine—NH₂ | O, SO |
| (−) | 1-CH₂N⁺—pyridine—NH₂ | O, SO |
| (−) | 6-CH₂N⁺—pyridine—NH₂ | O, SO |
| (−) | 7-CH₂N⁺—pyridine—NH₂ | O, SO |
| (−) | 8-CH₂N⁺—pyridine—NH₂ | O, SO |
| (−) | 5-CH₂N⁺—pyridine—NH₂ | O, SO |
| (−) | 1-CH₂N⁺—imidazole—N—CH₃ | O, S, SO, SO₂ |
| (−) | 6-CH₂N⁺—imidazole—N—CH₃ | O, S, SO, SO₂ |
| (−) | 7-CH₂N⁺—imidazole—N—CH₃ | O, S, SO, SO₂ |
| (−) | 8-CH₂N⁺—imidazole—N—CH₃ | O, S, SO, SO₂ |
| (−) | 5-CH₂N⁺—imidazole—N—CH₃ | O, S, SO, SO₂ |
| (−) | 7-CH₂N⁺—triazole—N—CH₃ | O, S, SO, SO₂ |
| (−) | 7-CH₂N⁺—triazole—N—CH₃ | O, S, SO, SO₂ |
| (−) | 7-CH₂N⁺—ring—NCH₂CONH₂ | O, S, SO, SO₂ |

-continued

| M | $R^a$ or $R^b$ | X |
|---|---|---|
| (−) | 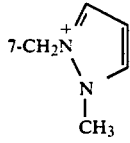 7-CH$_2$N$^+$ (pyrazole, N-CH$_3$) | O, S, SO, SO$_2$ |
| (−) | 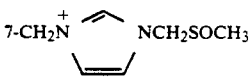 7-CH$_2$N$^+$—NCH$_2$SOCH$_3$ | O, S, SO, SO$_2$ |
| K | 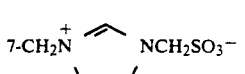 7-CH$_2$N$^+$—NCH$_2$SO$_3^-$ | O, S, SO, SO$_2$ |
| K | 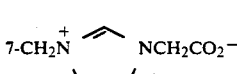 7-CH$_2$N$^+$—NCH$_2$CO$_2^-$ | O, S, SO, SO$_2$ |
| K | 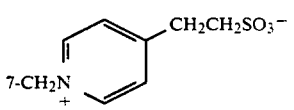 7-CH$_2$N$^+$ (pyridine-CH$_2$CH$_2$SO$_3^-$) | O, S, SO, SO$_2$ |
| K | 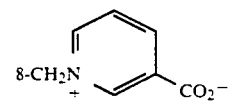 8-CH$_2$N$^+$ (pyridine-CO$_2^-$) | O, S, SO, SO$_2$ |
| (−) | 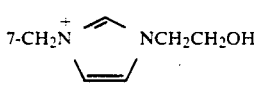 7-CH$_2$N$^+$—NCH$_2$CH$_2$OH | O, S, SO, SO$_2$ |
| (−) | 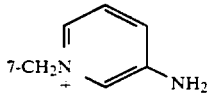 7-CH$_2$N$^+$ (pyridine-NH$_2$) | O, SO |
| (−) |  7-CH$_2$N$^+$ (pyridine-CH$_2$SCH$_3$=O, NH$_2$) | O, SO |
| (−) | 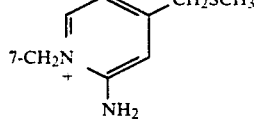 8-CH$_2$N$^+$ (pyridine-CH$_2$OH) | O, SO |
| (−) | 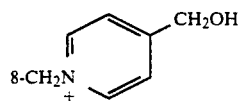 7-CH$_2$N$^+$ (pyridine-CH$_2$OH, NH$_2$) | O, SO |
| (−) | 6-CH$_2$N$^+$H(CH$_3$)$_2$ | O, SO |
| (−) | 1-CO$_2$CH$_2$CH$_2$N$^+$H(CH$_3$)$_2$ | O, SO |
| (−) | 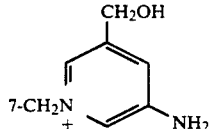 1-NSO$_2$CH$_2$CH$_2$N$^+$—N—CH$_3$ (H) | O, SO |

-continued

| M | $R^a$ or $R^b$ | X |
|---|---|---|
| (−) |  8-OCH$_2$CH$_2$N$^+$ (pyridine-NH$_2$) | O, SO |
| (−) |  1-SCH$_2$CH$_2$N$^+$ (pyridine-NH$_2$) | O, SO |
| (−) | 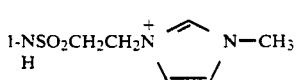 1-SO$_2$CH$_2$CH$_2$N$^+$ (pyridine-NH$_2$) | O, SO |
| (−) | 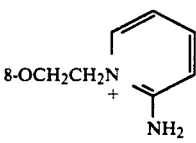 7-CH$_2$OCH$_2$CH$_2$N$^+$ (pyridine-NH$_2$) | O, SO |
| (−) | 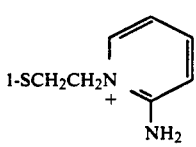 8-CH$_2$SCH$_2$CH$_2$N$^+$ (pyridine-NH$_2$) | O, SO |
| (−) | 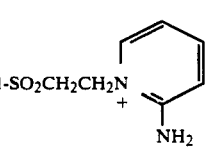 7-CH$_2$S(O)$_2$N$^+$ (pyridine-NH$_2$) | O, SO |
| (−) | 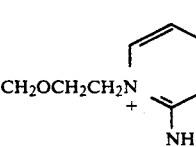 8-CH$_2$CH$_2$N$^+$ (pyridine-NH$_2$) | O, SO |
| (−) | 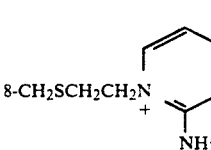 7-CCH$_2$N$^+$ (=O) (pyridine-NH$_2$) | O, SO |
| (−) | 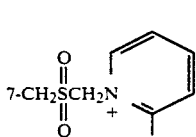 1-S(=O)$_2$NCH$_2$CH$_2$N$^+$ (pyridine-NH$_2$) (H) | O, SO |
| (−) | 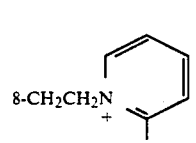 6-S(=O)—CH$_2$CH$_2$N$^+$—N—CH$_3$ | O, SO |

-continued
| M | R$^a$ or R$^b$ | X |
|---|---|---|
| (−) | 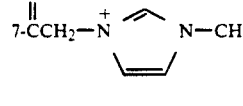 | O, SO |
| (−) | 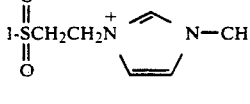 | O, SO |
| (−) | 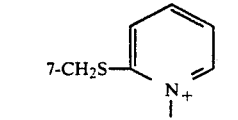 | O, SO |
| (−) | 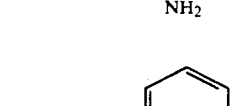 | O, SO |
| H | 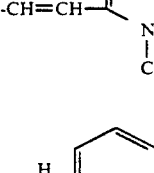 | O, SO |
| (−) | 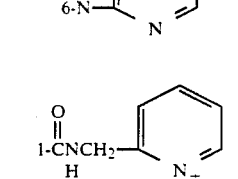 | O, SO |
| (−) |  | O, SO |
| (−) | 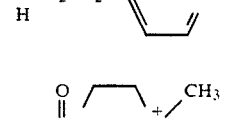 | O, SO |
| (−) | 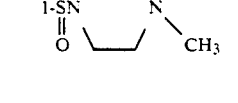 | O, SO |
| (−) | 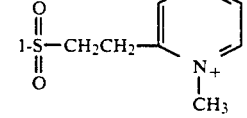 | O, SO |
| (−) | 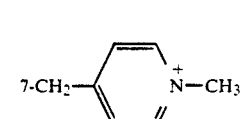 | O, SO |
| K | 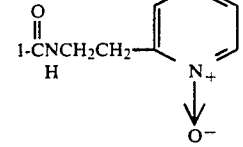 | O, SO |
| K | 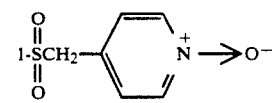 | O, SO |
| (−) | 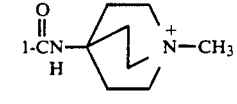 | O, SO |
| (−) | 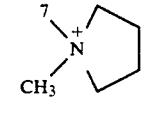 | O, SO |
| (−) | 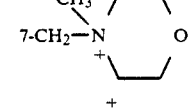 | O, SO |
| (−) | 8-CH$_2$—N$^+$(CH$_3$)$_3$ | O, SO |
| (−) | 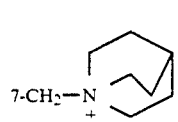 | O, SO |
| K |  | O, SO |
| K | 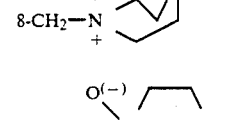 | O, SO |
| (−) | 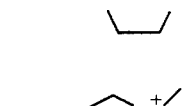 | O, SO |
| (−) | 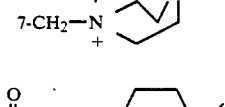 | O, SO |
| (−) | 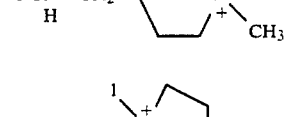 | O, SO |
| K | 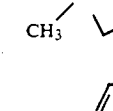 | O, S, SO, SO$_2$ |

-continued

| M | Rᵃ or Rᵇ | X |
|---|---|---|
| K | 6-CH₂NH-(2-pyridyl) | O, S, SO, SO₂ |
| K | 7-CH₂NH-(2-pyridyl) | O, S, SO, SO₂ |
| K | 1-C(O)NH-CH₂CH₂-(2-pyridyl) | O, S, SO, SO₂ |
| (—) | 1-C(O)NH-CH₂CH₂-(N-methylpyridinium-2-yl) | O, SO |

15. A compound

[carbapenem structure with substituents: HO-CH(CH₃)- at C-6, H or CH₃ at C-4, biphenyl system at C-3 with methyl, Rᵃ and X substituents on the distal ring, COOM at C-2]

| M | Rᵃ | Rᵇ | X |
|---|---|---|---|
| (—) | CN | 7-CH₂N⁺(pyrrolidinyl)-NCH₃ | O, S, SO, SO₂ |
| (—) | SOCH₃ | 7-CH₂N⁺(pyrrolidinyl)-NCH₃ | O, S, SO, SO₂ |
| (—) | CO₂K | 7-CH₂N⁺(pyrrolidinyl)-NCH₃ | O, S, SO, SO₂ |
| (—) | CO₂K | 8-CH₂N⁺(pyridinium)-NH₂ | O, S, SO, SO₂ |
| (—) | tetrazolyl-NK | 7-CH₂N⁺(pyridinium)-NH₂ | O, S, SO, SO₂ |
| (—) | tetrazolyl-NK | 8-CH₂N⁺(pyridinium)-NH₂ | O, S, SO, SO₂ |
| (—) | SO₃K | 8-CH₂N⁺(pyridinium)-NH₂ | O, S, SO, SO₂ |
| (—) | CO₂K | 7-N⁺-methylpyrrolidinium | O, S, SO, SO₂ |
| (—) | SO₃K | 7-N⁺-methylpyrrolidinium | O, S, SO, SO₂ |
| (—) | SO₃K | 8-CH₂-N⁺(CH₃)-piperidinium | O, S, SO, SO₂ |
| (—) | CHO | 7-CH₂N⁺(pyridinium)-NH₂ | O, S, SO, SO₂ |
| (—) | CONH₂ | 7-CH₂N⁺(imidazolium)-N-CH₃ | O, S, SO, SO₂ |
| (—) | SCH₃ | 7-CH₂N⁺(imidazolium)-N-CH₃ | O, S, SO, SO₂ |

16. A pharmaceutical composition for antibacterial use comprising an antibacterially effective amount of a compound of claim 1 and a pharmaceutically acceptable carrier therefor.

17. A method of treating bacterial infections in human or animal subjects in need of such treatment comprising administering to such subject an antibacterially effective amount of a compound of claim 1.

18. The combination of a compound of claim 1 and a DHP inhibitor.

19. The combination of a compound of claim 14 and the DHP inhibitor 7-(L-2-amino-2-carboxyethylthio)-2-(2,2-dimethylcyclopropanecarboxamide)-2-heptenoic acid.

20. The combination of a compound of claim 15 and the DHP inhibitor 7-(L-2-amino-2-carboxyethylthio)-2-(2,2-dimethylcyclopropanecarboxamide)-2-heptenoic acid.

21. A pharmaceutical composition for antibacterial use comprising an antibacterially effective amount of a compound of claim 1, an inhibitorily effective amount of a DHP inhibitor, and, optionally, a pharmaceutically acceptable carrier therefor.

22. A pharmaceutical composition according to claim 21 wherein the DHP inhibitor is 7-(L-2-amino-2-carboxyethylthio)-2-(2,2-dimethylcyclopropanecarboxyamide)-2-heptenoic acid.

23. A method of treating bacterial infections in human or animal subjects in need of such treatment comprising coadministering to such subject an antibacterially effective amount of a compound of claim 1 and an inhibitorily effective amount of a DHP inhibitor.

24. A method according to claim 23 wherein the DHP inhibitor is 7-(L-2-amino-2-carboxyethylthio)-2-(2,2-dimethylcyclopropanecarboxamide)-2-heptenoic acid.

* * * * *